United States Patent
Charles et al.

(10) Patent No.: US 6,723,106 B1
(45) Date of Patent: Apr. 20, 2004

(54) SURGICAL MANIPULATOR

(75) Inventors: Steve T. Charles, Germantown, TN (US); Robert Stoughton, Albuquerque, NM (US); J. Michael Stuart, Corrales, NM (US); Larry Bronisz, Los Alamos, NM (US)

(73) Assignee: MicroDexterity Systems, Inc., Memphis, TN (US)

( * ) Notice: Subject to any disclaimer, the term of this patent is extended or adjusted under 35 U.S.C. 154(b) by 0 days.

(21) Appl. No.: 09/856,453

(22) PCT Filed: Nov. 22, 1999

(86) PCT No.: PCT/US99/27560
§ 371 (c)(1), (2), (4) Date: Aug. 24, 2001

(87) PCT Pub. No.: WO00/30557
PCT Pub. Date: Jun. 2, 2000

Related U.S. Application Data
(60) Provisional application No. 60/109,608, filed on Nov. 23, 1998.

(51) Int. Cl.[7] ............................................. A61B 19/00
(52) U.S. Cl. ...................................................... 606/130
(58) Field of Search ......................... 606/1, 130; 415/5; 74/490.5, 490.6; 901/28, 29

(56) References Cited

U.S. PATENT DOCUMENTS

| | | |
|---|---|---|
| 3,923,166 A | 12/1975 | Fletcher et al. |
| 3,949,747 A | 4/1976 | Hevesy |
| 4,401,433 A | 8/1983 | Luther |
| 4,573,452 A | 3/1986 | Greenburg |

(List continued on next page.)

FOREIGN PATENT DOCUMENTS

| | | |
|---|---|---|
| EP | 0009447 A1 | 4/1980 |
| EP | 0 649 217 A1 | 4/1995 |
| EP | 0 654 244 A1 | 5/1995 |
| WO | WO 98/09580 A1 | 3/1998 |
| WO | WO/9910137 A1 | 3/1999 |
| WO | WO/0028882 A2 | 5/2000 |

OTHER PUBLICATIONS

Supplementary Partial European Search Report (Jun. 2002).
International Search Report (Feb. 28, 2000).
SHAI–SYG Motion & Innovations Ltd.; Robolite; copy of internet home page. Applicants first became aware of this material in Jun. 1998.
MicroE Inc.; copies of internet brochure pages of Rotary Micro Encoder and Linear Micro Encoder. Applicants first became aware of this material in Aug. 1998.
Computer Optical Products, Inc.; copies of internet home page and application notes relating to Hathaway Motion Control. Applicants first became aware of this material in Aug. 1998.
Renishaw; copies of internet home page and product page for Encoder System. Applicants first became aware of this material in Aug. 1998.

(List continued on next page.)

Primary Examiner—Kevin Shaver
Assistant Examiner—Michael B. Priddy
(74) Attorney, Agent, or Firm—Leydig, Voit & Mayer, Ltd.

(57) ABSTRACT

A surgical manipulator (10) can manipulate a medical tool (12) with one or more degrees of freedom. In preferred embodiments, the manipulator (10) is a parallel mechanism including a plurality of arms (21, 22) pivotally supporting a medical tool (12), with the orientation of the medical tool (12) being adjusted by varying the position of joints (23, 24) mounted on the arms (21, 22). The motions of the joints (23, 24) can be controlled such that the tool (12) is pivoted about a virtual pivot point located within the body wall of a patient (30). The manipulator (10) can enhance the dexterity of an operator and enable the operator to perform medical procedures more easily than by hand.

46 Claims, 31 Drawing Sheets

U.S. PATENT DOCUMENTS

| | | |
|---|---|---|
| 4,653,509 A | 3/1987 | Oloff et al. |
| 4,688,983 A | 8/1987 | Lindbom |
| 5,053,687 A | 10/1991 | Merlet |
| 5,078,140 A | 1/1992 | Kwoh |
| 5,081,381 A | 1/1992 | Narasaki |
| 5,086,401 A | 2/1992 | Glassman et al. |
| 5,142,930 A | 9/1992 | Allen et al. |
| 5,161,542 A | 11/1992 | Palestrant |
| 5,184,601 A | 2/1993 | Putman |
| 5,186,174 A | 2/1993 | Schlondorff et al. |
| 5,234,000 A | 8/1993 | Hakky et al. |
| 5,240,011 A | 8/1993 | Assa |
| 5,243,266 A | 9/1993 | Kasagami et al. |
| 5,251,127 A | 10/1993 | Raab |
| 5,273,039 A | 12/1993 | Fujiwara et al. |
| 5,279,309 A | 1/1994 | Taylor et al. |
| 5,280,427 A | 1/1994 | Magnusson et al. |
| 5,299,288 A | 3/1994 | Glassman et al. |
| 5,305,203 A | 4/1994 | Raab |
| 5,343,385 A | 8/1994 | Joskowicz et al. |
| 5,354,158 A | 10/1994 | Sheldon et al. |
| 5,383,454 A | 1/1995 | Bucholz |
| 5,386,741 A | 2/1995 | Rennex |
| 5,389,101 A | 2/1995 | Heilbrun et al. |
| 5,397,323 A | 3/1995 | Taylor et al. |
| 5,402,801 A | 4/1995 | Taylor |
| 5,408,409 A | 4/1995 | Glassman et al. |
| 5,415,182 A | 5/1995 | Chin et al. |
| 5,417,210 A | 5/1995 | Funda et al. |
| 5,425,616 A | 6/1995 | Arai et al. |
| 5,445,166 A | 8/1995 | Taylor |
| 5,464,013 A | 11/1995 | Lemelson |
| 5,494,034 A | 2/1996 | Schlondorff et al. |
| 5,564,436 A | 10/1996 | Hakky et al. |
| 5,568,593 A | 10/1996 | Demarest et al. |
| 5,572,999 A | 11/1996 | Funda et al. |
| 5,584,292 A | 12/1996 | Cheung |
| 5,628,327 A | 5/1997 | Unger et al. |
| 5,630,431 A | 5/1997 | Taylor |
| 5,643,286 A | 7/1997 | Warner et al. |
| 5,647,373 A | 7/1997 | Patielti |
| 5,695,500 A | 12/1997 | Taylor et al. |
| 5,748,767 A | 5/1998 | Raab |
| 5,749,362 A | 5/1998 | Funda et al. |
| 5,776,153 A | 7/1998 | Rees |
| 5,782,764 A | 7/1998 | Werne |
| 5,784,542 A | 7/1998 | Ohm et al. |
| 5,795,291 A | 8/1998 | Koros et al. |
| 5,797,900 A * | 8/1998 | Madhani et al. ............... 606/1 |
| 5,800,423 A | 9/1998 | Jensen |
| 5,803,912 A | 9/1998 | Siczek et al. |
| 5,806,518 A | 9/1998 | Mittelstadt |
| 5,828,197 A | 10/1998 | Martin et al. |
| 5,833,656 A | 11/1998 | Smith et al. |
| 5,851,183 A | 12/1998 | Bucholz |
| 5,865,744 A | 2/1999 | Lemelson |
| 5,887,121 A | 3/1999 | Funda et al. |
| 5,943,914 A | 8/1999 | Morimoto et al. |
| 5,950,629 A | 9/1999 | Taylor et al. |
| 5,951,475 A | 9/1999 | Gueziec et al. |
| 5,976,156 A | 11/1999 | Taylor et al. |
| 6,000,297 A | 12/1999 | Morimoto et al. |
| 6,021,342 A | 2/2000 | Brabrand |
| 6,024,695 A | 2/2000 | Taylor et al. |
| 6,106,511 A * | 8/2000 | Jensen ......................... 606/1 |

OTHER PUBLICATIONS

Del–Tron Precision Inc.; copies of internet brochure order form for Ball Slide Assemblies, Crossed Roller Slide Assemblies and Ball Slide Positioning Stages. Applicants first became aware of this material in Aug. 1998.

Encoder Products Company; copies of internet product guide for Model 770 C and Model 775. Applicants first became aware of this material in Aug. 1998.

Stoianovici et al., "A Modular Surgical Robotic System for Guided Percutaneous Procedures." Applicants first became aware of this article in Apr. 2000.

* cited by examiner

SURGICAL MANIPULATOR

REFERENCE TO RELATED APPLICATIONS

This application claims the benefit of U.S. Provisional Application No. 60/109,608 filed on Nov. 23, 1998, which is incorporated by reference.

BACKGROUND OF THE INVENTION

1. Field of the Invention

This invention relates to a manipulator, and particularly to a manipulator suitable for use in medical procedures, including minimally invasive surgical operations.

2. Description of the Related Art

In conventional open surgery on the interior of the human body, a surgeon must make an incision large enough to permit access to a region of interest as well as to allow a direct line of sight to the region. However, with the development of endoscopes, surgical tools which can be manipulated from outside a patient's body, and various imaging techniques such as ultrasonic imaging, computer tomography, and magnetic resonance imaging, it has become possible to perform surgery through very small incisions or body orifices of a size through which traditional open surgery would be impossible. Such surgery is generally referred to as minimally invasive surgery.

A typical surgical device for use in minimally invasive surgery includes an elongated tube having a first end which is inserted into a patient's body through an incision or orifice and a second end which extends to the outside of the patient's body and which is grasped by the surgeon. The first end is equipped with a surgical tool, such as a stapler, forceps, scissors, a needle holder, or a scalpel, while the second end is equipped with a handle or other member which is grasped by the surgeon and which is mechanically connected to the tool through the center of the tube. By manipulating the handle, the surgeon can operate the tool, and he can change the position of the tool by adjusting the orientation of the tube with respect to the patient's body.

Minimally invasive surgery, when feasible, is highly advantageous to the patient because it involves less trauma than does open surgery. It also frequently results in lower medical costs and shorter hospital stays. However, conventional minimally invasive surgical devices have a number of drawbacks. One drawback is that the surgeon can easily become fatigued by the need to manually support the minimally invasive surgical device during its use. Another drawback is that conventional minimally invasive surgical devices require the surgeon to assume an awkward position of his hands. Furthermore, conventional minimally invasive surgical devices can produce angular magnification of errors. As a result, a surgeon has considerably less dexterity and precision when performing an operation with minimally invasive surgical devices than when performing an operation by traditional techniques in which the surgeon grasps a tool directly. Therefore, minimally invasive surgery is used only for surgery which requires a low level of dexterity on the part of the surgeon.

SUMMARY OF THE INVENTION

The present invention provides a manipulator which is suitable for surgery and particularly minimally invasive surgery.

The present invention also provides a manipulator which can be used for diagnostic or therapeutic medical procedures.

The present invention further provides a manipulator which can decrease the fatigue of a surgeon during a surgical operation while increasing dexterity and precision.

The present invention also provides a manipulator having a high mechanical bandwidth.

The present invention additionally provides a manipulator having a small diameter so that it can be inserted into a small incision or body orifice of a patient.

The present invention yet further provides a method of performing various medical procedures, including surgical, diagnostic, and therapeutic procedures, with such a manipulator.

According to one form of the present invention, a manipulator includes first and second independently movable arms and a medical tool pivotably supported by both arms. The arms can be moved to manipulate the tool with one or more degrees of freedom. For example, in one preferred embodiment, the arms can manipulate the tool with five degrees of freedom.

The arms may manipulate the tool by various types of motions of the arms, such as by rotation of the arms as a whole about corresponding axes, or by translation or pivoting of parts of each arm with respect to each other to produce elongation or contraction of the arms or a change in the shape of the arms.

The manipulator may include a wrist capable of manipulating the tool with respect to the arms to provide the tool with additional degrees of freedom. In a preferred embodiment, the wrist and the tool can be detached from other portions of the manipulator to permit easy sterilization and replacement of the tool.

A manipulator according to the present invention can be operated in a variety of modes, including a master-slave mode in which its motions are controlled by a master controller, a robotic mode, or a semi-robotic mode in which some operations are robotic and other operations are controlled by a master controller.

A manipulator according to the present invention has numerous advantages over conventional minimally invasive surgical devices. For one, the surgeon does not need to support any portion of the manipulator during its operation, so the manipulator is less fatiguing for a surgeon to use, particularly during long operations. The manipulator can also support a medical device at an attitude which would be difficult to achieve by hand. In conventional minimally invasive surgery, the body wall through which an minimally invasive surgical tool is inserted typically must be substantially level and facing upward. In contrast, a manipulator according to the present invention imposes no restrictions on the orientation of the body wall through minimally invasive surgery is performed. For example, the body wall could be vertical or facing downward if the patient can be placed on a table having an opening through which the manipulator can pass to access the body wall. Thus, a patient can be positioned in a manner which is comfortable for the patient and the surgeon and advantageous with respect to patient safety and recovery.

Another significant advantage of a manipulator according to the present invention is that it can enhance the dexterity of the user. Whereas a conventional minimally invasive surgical device invariably reduces the dexterity of the surgeon compared to his dexterity when operating by hand, a manipulator according to the present invention can provide the surgeon with dexterity comparable or even superior to that achievable by the unaided hand.

A manipulator according to the present invention is particularly suitable for minimally invasive surgical operations or other medical procedures performed through small incisions in the body wall of a patient. However, a manipulator according to the present invention can be used in medical procedures other than minimally invasive surgery, such as for external surgery or traditional open surgery entailing large incisions in the body wall. It can also be used in non-medical applications. For example, it can be employed as a general purpose manipulator for use in manufacturing, repair, installation, or support of various objects.

DESCRIPTION OF PREFERRED EMBODIMENTS

Figure 1:
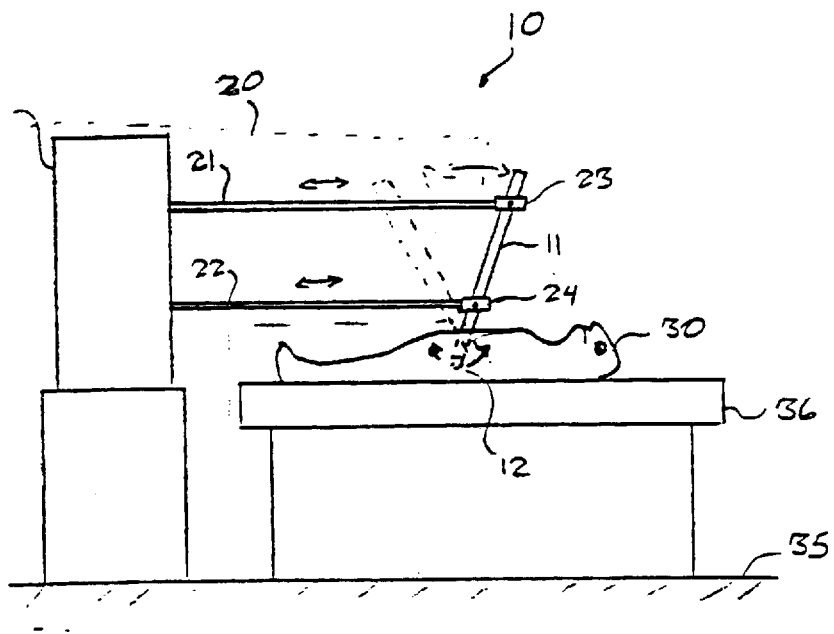
FIG. 1 is a schematic side elevation illustrating the concept of a surgical manipulator according to the present invention.

A number of preferred embodiments of a manipulator according to the present invention will now be described with reference to the accompanying drawings. The present invention is not restricted to the structures shown in the drawings, and features of one embodiment may be freely combined with features of one or more other embodiments to obtain numerous arrangements in addition to the illustrated ones, all falling within the scope of the present invention.

FIG. 1 is a schematic elevation conceptually illustrating the overall structure of a manipulator 10 according to the present invention. The manipulator 10 is shown being used to perform a minimally invasive surgical operation on a human patient 30, but as stated above, it can employed for medical procedures other than minimally invasive surgery. Furthermore, it is not restricted to use with human patients and can be used in veterinary medicine, for example.

The illustrated manipulator 10 includes a tool support shaft 11 having a medical device 12, such as a surgical tool, mounted at one end (the lower end in the figure). In the following description, the medical device 12, whatever its character, will be referred to simply as a tool. There are no restrictions on the type of the tool 12. For example, the tool 12 can be a cutting device, a needle holder, staples, forceps, a clamp, a probe, an imaging device, a laser, a needle or other biopsy device, a device for administering medication or other substances, or other device for surgical, therapeutic, or diagnostic purposes. The tool support shaft 11 is supported and manipulated by a shaft support structure 20 including two or more independently movable arms 21 and 22, each arm pivotably supporting the tool support shaft 11 at a different location through one or more joints. In this example, arm 21 is equipped with one pivotable joint 23 and arm 22 is equipped with another pivotable joint 24. Each arm 21, 22 can move the corresponding joint 23, 24 in space to adjust the position of the tool support shaft 11 in space to achieve a desired position and/or motion of the lower end of the tool support shaft 11 to move the tool 12 to a desired location with respect to the patient. In the present embodiment, a single joint 23 or 24 provides the desired number of rotational degrees of freedom of the tool support shaft 11 with respect to each arm 21 or 22, but a single joint providing multiple rotational degrees of freedom may be replaced by its functional equivalent in the form of a plurality of joints each providing fewer rotational degrees of freedom than the single joint but together providing the same number of degrees of freedom as the single joint. The joints 23, 24 are typically passive joints rather than active joints, meaning that a change of orientation of the tool support shaft 11 with respect to the arms 21 and 22 is produced simply by changing the position of one or both joints 23, 24 rather than by exerting a torque on the tool support shaft 11 with actuators associated with the joints 23, 24.

The shaft support structure 20 defines a parallel mechanism, i.e., a mechanism in which the weight of the tool support shaft 11 is transmitted to a base or other support member along a plurality of parallel paths defined by the arms 21 and 22, in contrast to a serial mechanism in which a load being supported is transmitted to a base along a single path. A parallel mechanism is inherently stiffer, quicker, more accurate, and capable of carrying a higher load than a serial mechanism, features which are all particularly advantageous for a surgical manipulator.

The arms 21 and 22 can move the joints 23 and 24 by many different types of actions, such as by elongation or contraction of the arms, or by translation or pivoting of the entire arms or of portions of the arms.

The tool support shaft 11 is not restricted to any particular shape. Frequently, its lower end will be straight to facilitate insertion into a patient's body, and for ease of manufacture, it may be convenient if the tool support shaft 11 is straight over its entire length. However, it may have a wide variety of other shapes, such as angulated or curved. The tool support shaft 11 is shown as having a constant transverse cross-sectional shape over its length, but the cross-sectional shape is also not critical and may vary over its length. The illustrated tool support shaft 11 is an elongated member with a length which is large compared to its diameter, but the ratio of the length of the tool support shaft 11 to its diameter is not important. Thus, the tool support shaft 11 may be any member capable of supporting the tool 12 and being manipulated in a desired manner.

The weight of the tool support shaft 11 can be distributed between the joints 23, 24 in any desired manner. In some orientations of the tool support shaft 11, its weight may be supported primarily or entirely by only one of the joints 23, 24, whereas in other orientations, the weight may be supported by both of the joints. The locations of the joints 23, 24 in space can be varied, but the orientation of a line connecting the centers of rotation of the joints with each other remains constant with respect to the tool support shaft 11. Two passive joints are sufficient to define the orientation of the tool support shaft 11 in space, but a larger number of joints and arms can be employed if it is desired to distribute the weight of the tool support shaft 11 among a larger number of members.

In some configurations of the shaft support structure 20, the arms 21, 22 may be coplanar with each other, in which case the shaft support structure 20 will define a two-dimensional linkage. However, the shaft support structure 20 may assume configurations in which the arms 21, 22 are nonplanar, in which case the shaft support structure 20 can define a so-called space mechanism or three-dimensional linkage. The ability of the shaft support structure 20 to function as a space mechanism increases the freedom of movement of the tool support shaft 11 and permits movements which are not possible with a two-dimensional linkage.

In FIG. 1, the centers of rotation of the joints 23, 24 are schematically illustrated as coinciding with the longitudinal axis of the tool support shaft 11, but the locations of the centers of rotation of the joints with respect to the tool support shaft 11 are arbitrary. For example, the joints may support the tool support shaft 11 through an intermediate member, such as a frame, and so may be spaced from the tool support shaft 11.

Figure 2:
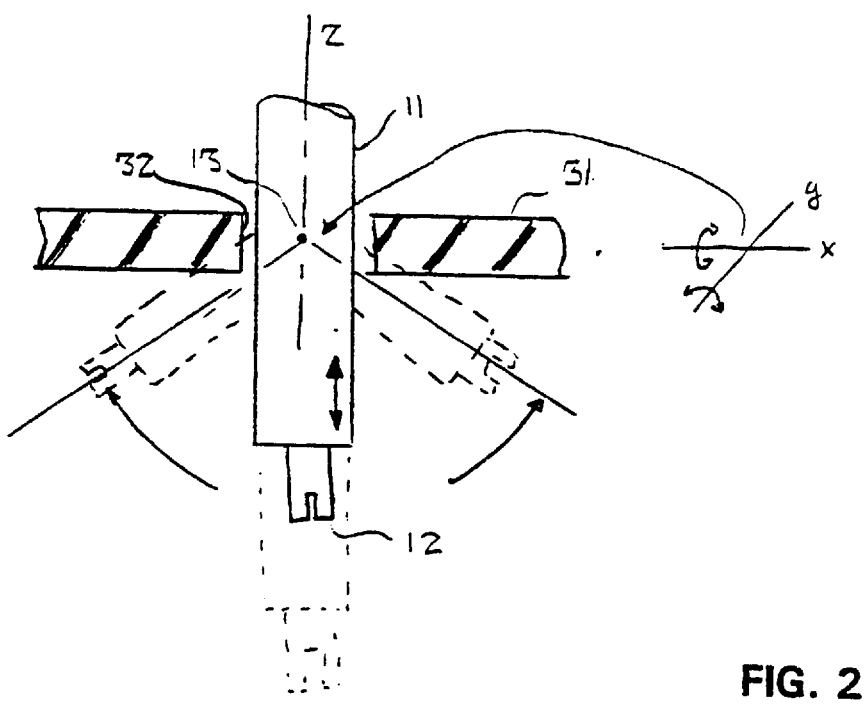
FIG. 2 is a schematic side elevation of the lower end of the tool support shaft of FIG. 1, illustrating how the tool support shaft can be manipulated within a cone angle.

The shaft support structure 20 may be designed to manipulate the tool support shaft 11 with any desired number of degrees of freedom in translation and/or rotation. For some simple medical procedures, a single degree of freedom may be sufficient, but it is frequently convenient if the tool support shaft 11 can be manipulated with multiple degrees of freedom. For example, when the tool support shaft 11 is being maneuvered with the tool 12 on the exterior of the patient's body, it may be desirable for the shaft support structure 20 to be capable of manipulating the tool support shaft 11 with up to six degrees of freedom. However, when the lower end of the tool support shaft 11 is inserted into an incision or other opening in a patient's body, it is generally desirable to limit the number of degrees of freedom of the tool support shaft 11 so as to minimize the size of the incision required to accommodate the motions of the tool support shaft 11. More specifically, as schematically shown in FIG. 2, the motions of the tool support shaft 11 when inserted through an incision 32 in the body wall 31 of a patient 30 into the patient's body are preferably limited to those which maintain the longitudinal axis of the lower end of the tool support shaft 11 within an imaginary cone centered at a virtual pivot point 13 located in the incision 32. A virtual pivot point refers to a point in space about which the tool support shaft 11 can be rotated with one or more degrees of freedom without the need for any support structure at the virtual pivot point. The tool support shaft 11 is capable of being pivoted as if there were actually a rotational joint located at the virtual pivot point 13 but without the structural limitations that such a joint might impose. In FIG. 2, the tool support shaft 11 can be rotated about an x axis and a y axis perpendicular to the x axis, both axes passing through the virtual pivot point 13. Furthermore, the tool support shaft 11 can be translated along a z axis corresponding to the longitudinal axis of the tool support shaft 11. The size of the cone (measured as an angle) in which the tool support shaft 11 is capable of moving can be selected based on factors such as the size of the incision 32 and the extent to which the body wall 31 can withstand stretching if contacted by the outer surface of the tool support shaft 11. Within this cone, the tool support shaft 11 may be made to perform any combination of rotation about the x and/or y axes and translation along the z axis with the longitudinal axis of the tool support shaft 11 remaining aligned with the virtual pivot point 13. The tool support shaft 11 can also be made to rotate about the z axis, if desired. In order to minimize the size of the incision 32 required to accommodate a given cone angle, the virtual pivot point 13 is preferably located roughly halfway through the thickness of the body wall 31 of the patient 30 where the incision 32 or other opening is formed. This thickness can vary widely from patient to patient. It may be less than half an inch for an infant and 4 to 5 inches for an obese adult.

By appropriately coordinating the motions of the arms 21, 22, the virtual pivot point 13 about which the tool support shaft 11 is pivoted can be located at any desired point in space. For example, it can be located anywhere along the length of the tool support shaft 11. The ability of the location of the virtual pivot point 13 to be varied along the length of the tool support shaft 11 is useful since it enables the amount by which the tool support shaft 11 extends into the body of the patient to be adjusted to a desired value. Thus, when the portion of the patient's body which is to be accessed by the tool 12 is close to the body wall 31, the virtual pivot point 13 may be close to the lower end of the tool support shaft 11, while if the portion to be accessed is deeper within the patient's body or further from the incision 32, the virtual pivot point 13 may be farther from the lower end of the tool support shaft 11 to permit a greater length of the tool support shaft 11 to be inserted into the patient's body.

The shaft support structure 20 can be supported in any suitable manner. In FIG. 1, it is shown mounted on a floor 35 adjoining a table 36 on which a patient 30 is lying during surgery, but it may instead be mounted on the table 36, a wall, on a ceiling, on an imaging gantry above the patient 30, or on any other suitable structure. The shaft support structure 20 may be installed in a fixed location, or it may be equipped with rollers or other mechanisms to give it mobility.

Many different configurations can be employed which enable the shaft support structure to manipulate the tool support shaft 11 in the manner shown in FIG. 2. For example, (a) both of the joints 23, 24 can be moved in two-dimensional space (in separate planes), and the tool support shaft 11 can be translated with respect to the joints 23, 24 in a direction transverse to the planes of movement of the joints 23, 24;

(b) both of the joints 23, 24 can be moved in two-dimensional space relative to a base, and the planes of movement of the joints 23, 24 can be moved as a single unit in a direction transverse to the planes while maintaining a constant positional relationship to each other to produce translation of the tool support shaft 11 in the z-axis direction;

(c) one of the joints 23, 24 can be moved in two-dimensional space while the other joint can be moved in three-dimensional space;

(d) both of the joints 23, 24 can be moved in three-dimensional space.

Any combination of (a)–(d) can also be employed, and the joints may be moved in still other manners.

Figure 3:
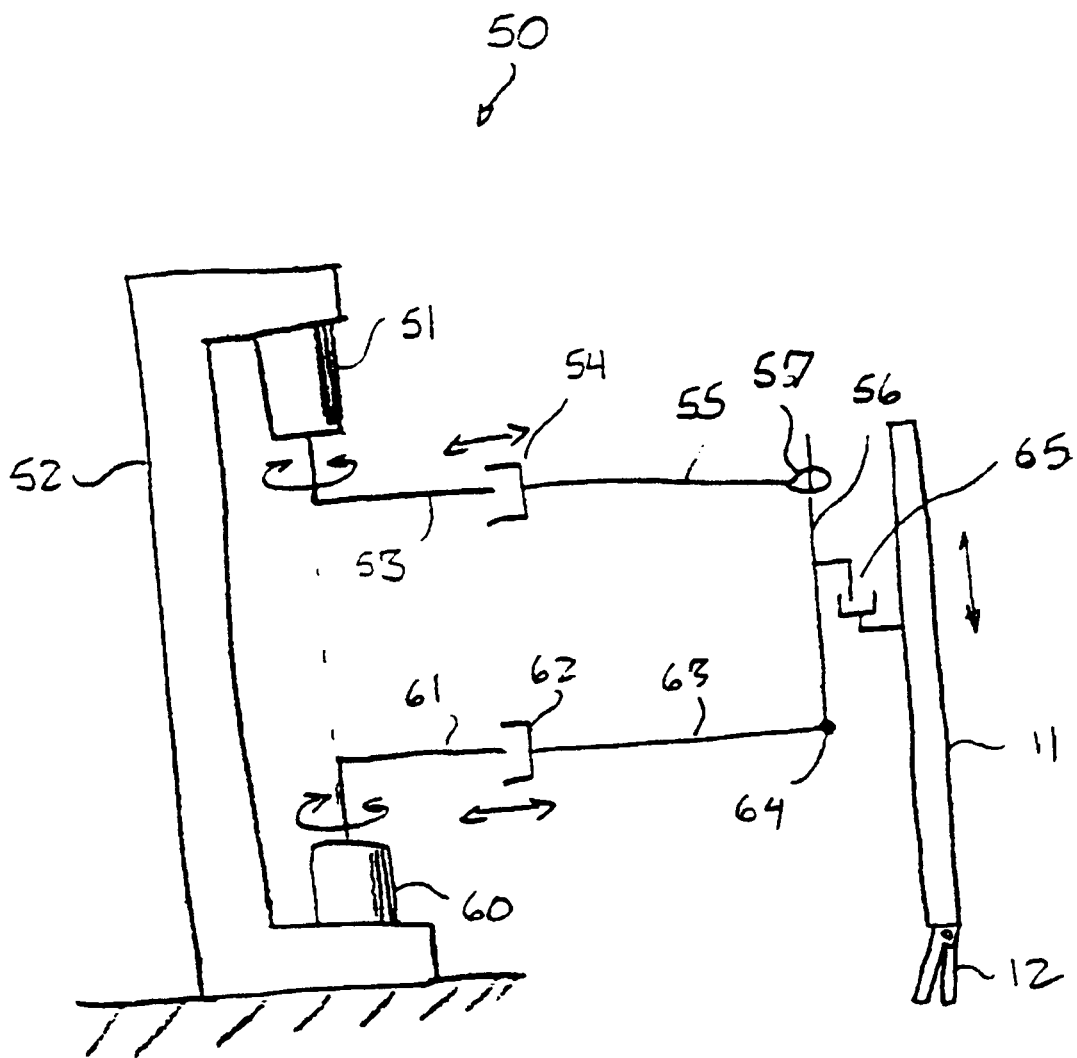
FIG. 3 is a schematic representation of one form of a manipulator according to the present invention employing rotary actuators in combination with linear actuators.

FIG. 3 schematically illustrates the geometry of a shaft support structure 50 having the configuration described in paragraph (a) above in which two joints are each moved in two-dimensional space by two corresponding arms. As shown in this figure, the shaft support structure 50 includes a first arm including a first rotary actuator 51 supported by a stationary support 52, such as a stationary frame. A first link 53 is secured to the first rotary actuator 51 for rotation about a first axis. The first link 53 supports a first linear actuator 54 which can act along a straight path perpendicular to the rotational axis of the first rotary actuator 51. A second link 55 has one end secured to the first linear actuator 54 and another end connected to a third link 56, which supports a tool support shaft 11, at a first support point by a first pivotable joint 57. The second arm includes a second rotary actuator 60 supported by a stationary support, such as the same frame 52 which supports the first rotary actuator 51. A fourth link 61 is secured to the second rotary actuator 60 for rotation about a second axis. For simplicity of kinematics, the rotational axes of the first and second rotary actuators 51, 60 are aligned with each other in FIG. 3, but the two axes need not be either aligned or parallel. The fourth link 61 supports a second linear actuator 62 which can act along a straight path perpendicular to the rotational axis of the second rotary actuator 60. A fifth link 63 has one end secured to the second linear actuator 62 and another end connected to the third link 56 at a second support point by a second pivotable joint 64. Each of the first and second joints 57, 64 permits at least two rotational degrees of freedom of the third link 56 with respect to second and fifth links 55, 63 so that the third link 56 can pitch and yaw with respect to the second and fifth links 55, 63. The third link 56 and the joints 57, 64 are also arranged such that the angle between links 55, 63 measured about the axis of the third link 56 can vary. For example, one of the joints 57, 64 may provide three rotational degrees of freedom so that the third link 56 can perform a rolling motion about its axis with respect to one of the second and fifth links 55, 63 in addition to a pitching and yawing motion. In this case, one of the joints 57, 64 can be a gimbals joint or its equivalent while the other joint is a spherical joint or its equivalent. Alternatively, each of joints 57, 64 may have only two rotational degrees of freedom, and the third link 56 may be formed of two sections connected by a roll joint having a rotational axis aligned with the axis of the third link 56 and permitting the two sections of the link 56 to rotate with respect to each other about the axis of the third link 56. The joints 57, 64 are arranged so that the distance between them can vary as they move in parallel planes in space. For example, in this embodiment, one of the joints (such as the first joint 57 in FIG. 3) is fixed against translation with respect to the third link 56 in the lengthwise direction of the third link, while the other joint (the second joint 64 in this example) is capable of translating with respect to the third link 56 in the lengthwise direction thereof. The distance between the joints 57, 64 can be allowed to vary in other ways, such as by fixing each joint 57, 64 against translation with respect to the portion of the third link 65 to which the joint is attached and forming the third link 56 as a telescoping member.

The third link 56 supports the tool support shaft 11 through a third linear actuator 65 (a shaft insertion actuator) which can translate the tool support shaft 11 in a direction transverse to the planes of movement of the first and second joints 57, 64 and which can be used to insert or withdraw the tool support shaft 11 with respect to a patient's body without changing the orientation of the tool support shaft 11. In the present embodiment, the third linear actuator 65 acts in a direction parallel to a line connecting the first and second joints 57, 64, but it may instead act in a different direction. The line of action of the third linear actuator 65 is shown as being offset from a line connecting the first and second joints 57, 64 but may also be aligned with it.

The first through fifth links are shown as being formed from linear sections. For example, the first and fourth links 53, 61 are shown as comprising two sections at right angles to each other, and the remaining links 55, 56, and 63 are shown as being straight members. However, as long as the first and second joints 57, 64 can be moved in planes, the shape of the links is arbitrary. Thus, for example, the links could be angulated, curved, or have a combination of straight and curved sections.

Figure 4:
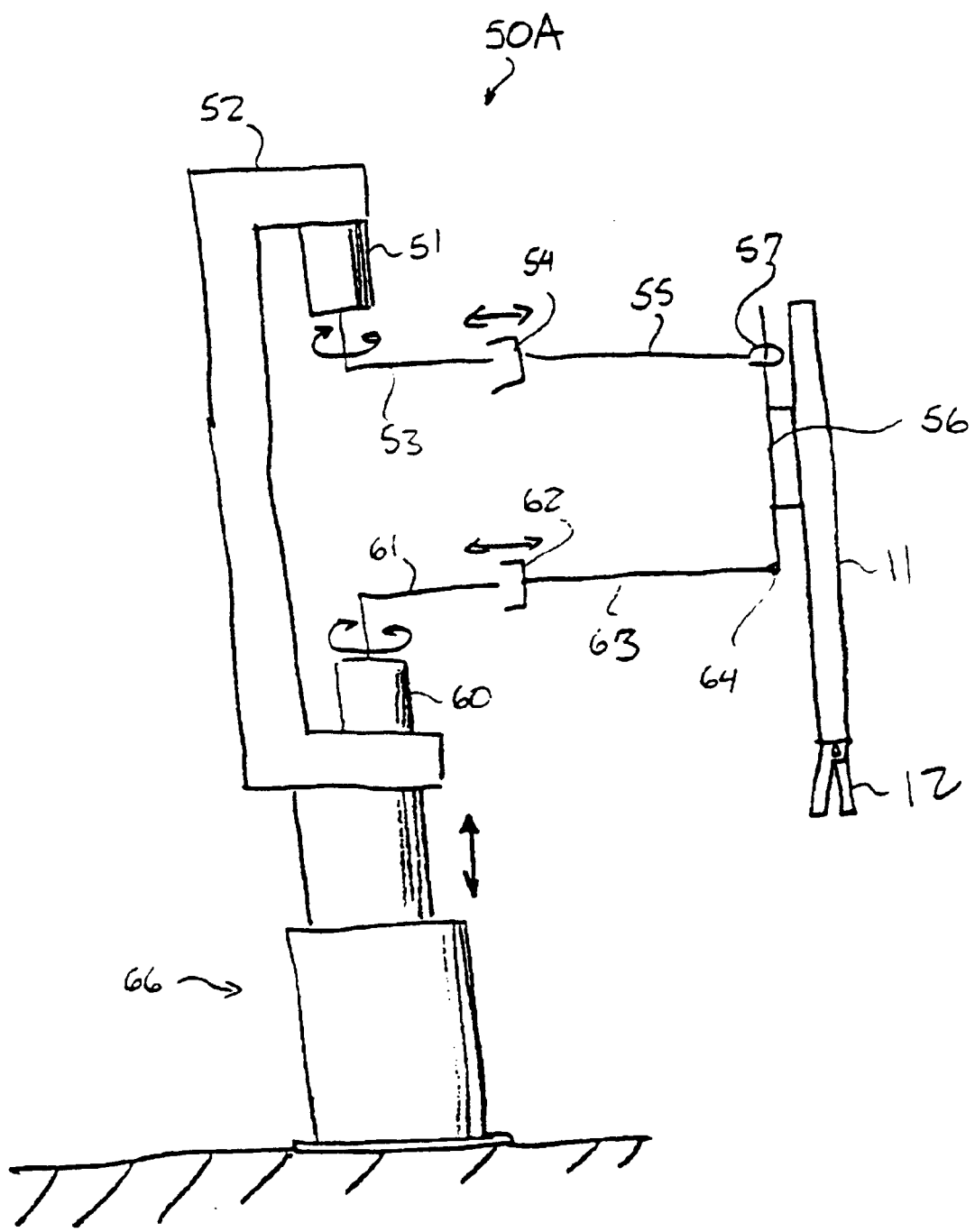
FIG. 4 is a schematic representation of a modification of the arrangement shown in FIG. 3.

FIG. 4 schematically illustrates the geometry of another shaft support structure 50A which can be employed in the present invention. This example has the configuration described in paragraph (b) above in which two joints are moved in two-dimensional space by two arms, and the joints can be moved as a unit in a direction transverse to the planes of movement of the joints. The overall geometry of FIG. 4 is similar to that of the geometry of FIG. 3, except that the third linear actuator 65 (the shaft insertion actuator) has been omitted, and movement of the tool support shaft 11 in the z-axis direction is achieved by translating the rotary actuators 51, 60 as a single unit. The tool support shaft 11 is rigidly connected to the fifth link 56. The rotary actuators 51, 60 are connected to a frame 52 which can be raised and lowered by a base 66 equipped with an elevating mechanism for the frame 52. The geometry of FIG. 4 can produce the same rotational and translational movement of the tool support shaft 11 as can the geometry of FIG. 3. Because a shaft insertion actuator 65 is not necessary, the size of the manipulator 50A in the vicinity of the upper end of the tool support shaft 11 can be reduced, making it easier to operate the manipulator in crowded spaces. However, for greater operational flexibility, it is possible to further equip the arrangement of FIG. 4 with a third linear actuator, corresponding to the third linear actuator 65 of FIG. 3, for translating the tool support shaft 11 in the z-axis direction to insert or withdraw the tool support shaft with respect to a patient's body.

Figure 5:
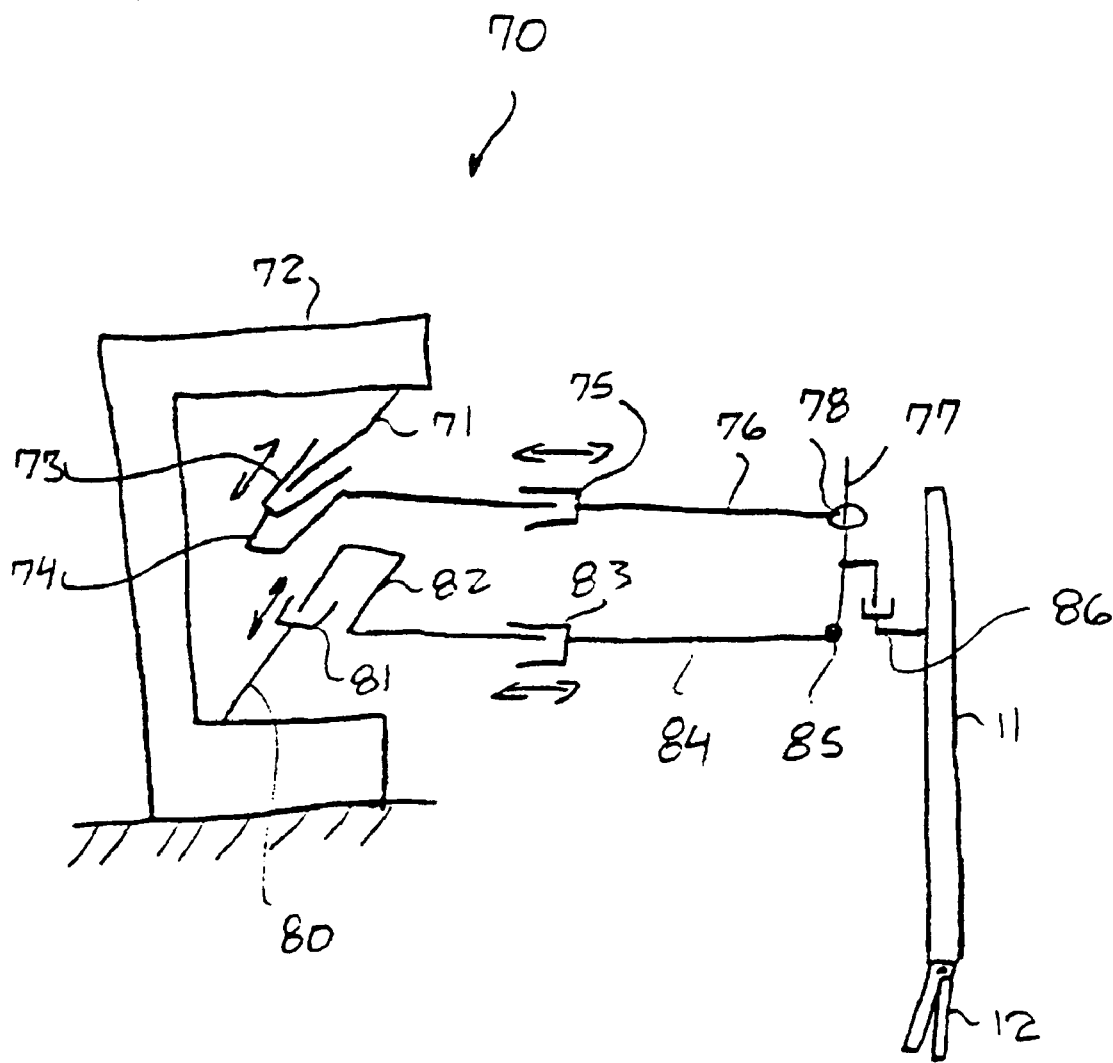
FIG. 5 is a schematic representation of another form of a manipulator according to the present invention employing only linear actuators.

FIG. 5 schematically illustrates the geometry of another shaft support structure 70 according to the present invention. As in the geometries of FIGS. 3 and 4, two joints for a tool support shaft are both moved in two-dimensional space by first and second arms. In contrast to those geometries, this geometry employs only linear actuators to maneuver the joints.

A first arm includes a first link 71 having one end connected to a stationary support, such as a base, and a second end connected to a first linear actuator 73 which can move in a straight line in an x-axis direction. A second link 74 has one end connected to the first linear actuator 73 and a second end connected to a second linear actuator 75 which can move in a straight line in a y-axis direction transverse to (such as perpendicular to) the x-axis direction. In the present embodiment, the x and y axes are perpendicular to each other but need not be. A third link 76 has a first end connected to the second linear actuator 75 and a second end connected to a fourth link 77 at a first support point for the tool support shaft by a first pivotable joint 78. The second arm includes a fifth link 80 having one end connected to a stationary support, such as the same member 72 to which the first link 71 is connected, and a second end connected to a third linear actuator 81 which can act in a straight line in the x-axis direction. A sixth link 82 has one end connected to the third linear actuator 81 and another end connected to a fourth linear actuator 83 which can move in a straight line in the y-axis direction. Thus, the third linear actuator 82 moves in a path parallel to the first linear actuator 73, and the fourth linear actuator 73 moves in a path parallel to the second linear actuator 75 and perpendicular to that of the third linear actuator 81. Furthermore, the paths of movement of the first and second linear actuators define a plane parallel to that defined by the paths of movement and the third and fourth linear actuators. However, the paths of movement of the third and fourth linear actuators can be at any angle with respect to each other such that they are not parallel, the paths of movement of the third and fourth linear actuators 81, 83 need not be parallel to those of the first and second linear actuators 73, 75, respectively, and the plane defined by the paths of movement of the first and second linear actuators. A seventh link 84 has one end connected to the fourth linear actuator 83 and another end connected to the fourth link 77 at a second support point by a second pivotable joint 85. A fifth linear actuator 86 (a shaft insertion actuator) which can move in a z-axis direction transverse to the planes of movement of the first and second joints 78, 85 is mounted on the fourth link 77 and supports the tool support shaft 11. In FIG. 5, the z axis is parallel to a straight line connecting the first and second joints 78, 85, but it may extend in a different direction.

Each of the first and second joints 78, 85 can permit two rotational degrees of freedom of the fourth link 77 with respect to the third and seventh links 76, 84 so as to allow the fourth link 77 to pitch and yaw with respect to the third and seventh links 76, 84. One of the joints 78, 85 may provide three rotational degrees of freedom to enable the fourth link 77 to perform a rolling motion in addition to a pitching and yawing motion, but since links 76 and 84 maintain a constant orientation in space, a third rotational degree of freedom is not needed. The joints 78, 85 are arranged so that the distance between them can vary as they move in parallel planes in space. For example, one of the joints (the second joint 85 in FIG. 5) may be fixed against translation with respect to the fourth link 77 in the lengthwise direction of the fourth link 77, while the other joint (the first joint 78 in this example) may be capable of translating with respect to the fourth link 77 in the lengthwise direction of the link 77. Alternatively, both joints 78, 85 may be fixed against translation with respect to the fourth link 77, and the fourth link 77 may have a telescoping structure which allows the distance between the joints 78, 85 to vary.

Instead of manipulating both of the joints 78, 85 solely with linear actuators, it is possible to manipulate one (either the first or the second) of the joints of FIG. 5 with the combination of a rotary actuator and a linear actuator in the same manner as in the arrangement of FIG. 3. For example, components 71, 73, and 74 of FIG. 5 for manipulating joint 78 could be replaced by a rotary actuator and a link corresponding to components 51 and 53 of FIG. 3. This would result in a hybrid of the arrangements of FIGS. 3 and 5.

Figure 6:
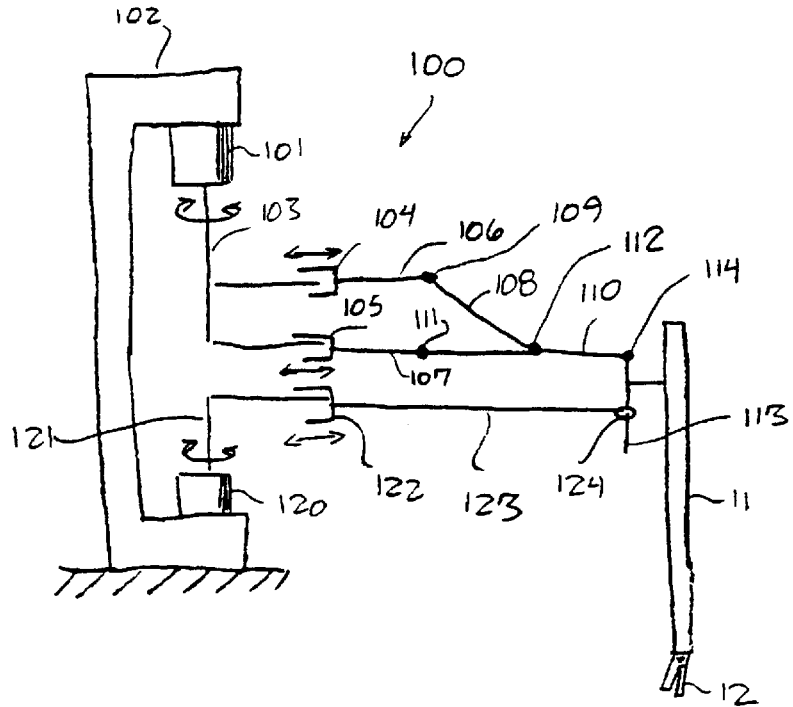
FIGS. 6 and 7 are schematic representations of two other forms of a manipulator according to the present invention employing rotary actuators in combination with linear actuators.

FIG. 6 illustrates the geometry of a shaft support structure 100 according to the present invention in which one joint for a tool support shaft 11 can be moved in two-dimensional space by a corresponding arm, while a second joint can be moved in three-dimensional space by another arm. First and second rotary actuators 101, 120 of a first and second arm, respectively, are each secured to a stationary support, such as a frame 102. The first rotary actuator 101 can rotate a first link 103 about an axis. The first link 103 is connected to first and second linear actuators 104, 105 which can act in straight lines perpendicular to the rotational axis of the first rotary actuator 101 and parallel to each other. A second link 106 and a third link 107 each have one end connected to the first linear actuator 104 and the second linear actuator 105, respectively. A fourth link 108 has a first end pivotably connected to an end of the second link 106 by a joint 109, and a fifth link 110 has a first end pivotably connected to an end of the third link 107 by a joint 111. The second end of the fifth link 110 is pivotably connected by a joint 114 at a first support point to a sixth link 113 to which the tool support shaft 11 is secured. The second end of the fourth link 108 is pivotably connected to the fifth link 110 by a joint 112 located between the two ends of the fifth link 110. Each of joints 109, 111, and 112 provides one rotational degree of freedom about an axis perpendicular to the rotational axis of the first rotary actuator 101, with the axes of rotation of all three joints being parallel to each other and perpendicular to the paths of movement of linear actuators 104 and 105. The second rotary actuator 120 rotates a seventh link 121 about a rotational axis. For simplicity of kinematics, this rotational axis is preferably aligned with the rotational axis of the first rotary actuator 101, but the two axes need not be either aligned or parallel. The seventh link 121 is secured to a third linear actuator 122 which acts along a straight line perpendicular to the rotational axis of the second rotary actuator 120. An eighth link 123 has one end connected to the third linear actuator 122 and another end connected to the sixth link 113 at a second support point by a joint 124. Joints 114 and 124 each permit the sixth link 113 to pivot with at least two rotational degrees of freedom with respect to the fifth or eighth links 110 and 123. The sixth link 113 and joints 114, 124 are also arranged such that the angle between links 110 and 123 measured about the axis of the sixth link 113 can vary, such as by giving one of joints 114 and 124 three rotational degrees of freedom or by building a roll joint into the sixth link 113 so that two sections of the sixth link 113 can rotate with respect to each other about the longitudinal axis of the sixth link 113. Joint 114 is fixed against translation with respect to the sixth link 113 in the lengthwise direction of the sixth link 113, and joint 124 is capable of translation with respect to the sixth link 113 in the lengthwise direction of the sixth link 113 to enable the distance between joints 114 and 124 to vary. Alternatively, both joints 114 and 124 may be fixed against translation with respect to the sixth link 113, and the sixth link 113 may have a telescoping structure which allows the distance between joints 114 and 124 to vary.

In this geometry, joint 124 and joints 109 and 111 each move in two-dimensional space, i.e., in a plane. In contrast, joint 114 can be moved in three-dimensional space. For example, joint 114 can be moved upwards in FIG. 6 by controlling the first and second linear actuators 104, 105 to move joint 109 toward the rotational axis of the first rotary actuator 101 while maintaining joint 111 stationary, while joint 114 can be moved downward in FIG. 6 by controlling the first and second linear actuators 104, 105 to move joint 109 away from the rotational axis of the first rotary actuator 101 while maintaining joint 111 stationary. Therefore, the tool support shaft 11 can be moved in the z-axis direction by varying the distance of the joint 114 from the plane of movement of joint 124 without the need for a separate shaft insertion actuator. As a result, the size of the support shaft support structure 100 near the upper end of the tool support shaft 11 can be reduced, making it easier to manipulate the tool support shaft 11 in crowded spaces.

Figure 7:
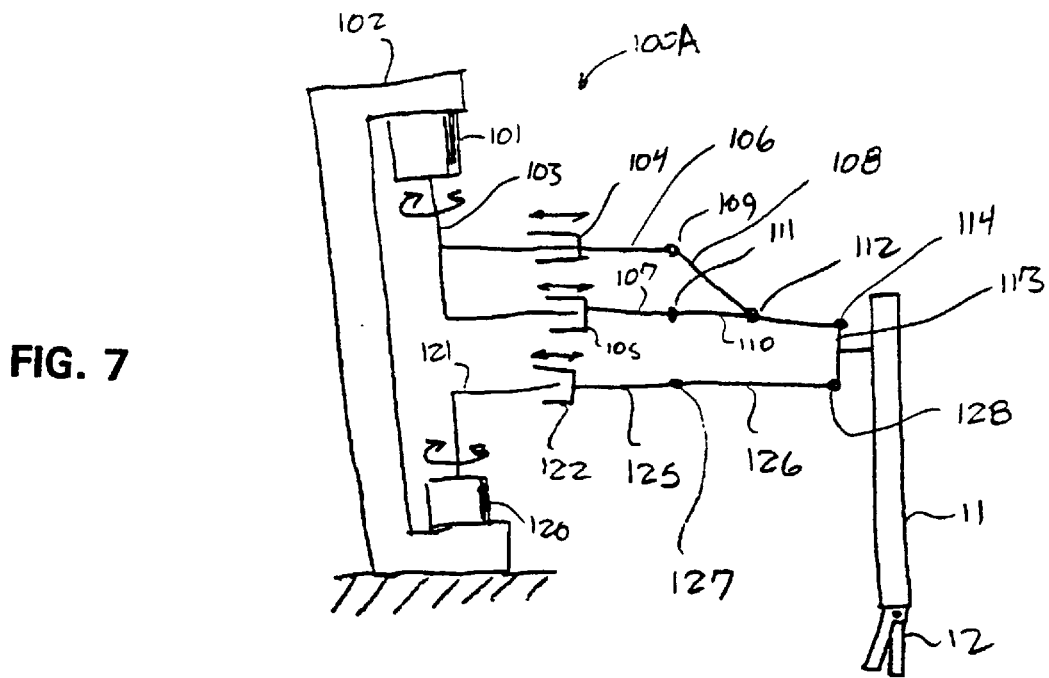

FIG. 7 illustrates another possible geometry of a shaft support structure 100A of a manipulator according to the present invention. This geometry is similar to the geometry in FIG. 6, but it is capable of manipulating two joints in three-dimensional space. However, the eighth link 123 of FIG. 6 has been replaced by an eighth link 125 and a ninth link 126 pivotably connected together by a joint 127 providing one rotational degree of freedom about an axis parallel to the axes of rotation of joints 109, 111, and 112. One end of the eighth link 125 is secured to the third linear actuator 122, and one end of the ninth link 126 is pivotably connected to the sixth link 113 by a joint 128 which provides at least two rotational degrees of freedom of the sixth link 113 with respect to the ninth link 126. As in the embodiment of FIG. 6, the sixth link 113 and joints 114, 128 are arranged such that the angle between links 110 and 126 measured about the axis of the sixth link 113 can vary using any suitable structure. In contrast to joint 124 of FIG. 6, joint 128 in FIG. 7 is fixed against translation with respect to the sixth link 113 in the lengthwise direction of the sixth link 113. Joint 127 between the eighth and ninth links 125, 126 is moved in two-dimensional space, while joint 128 is capable of being moved in three-dimensional space. In essence, the translational freedom of joint 124 in FIG. 6 has been replaced by rotational joint 127 and link 126.

In this geometry, each of joints 109, 111, and 127 can be moved in two-dimensional space, whereas joints 114 and 128 can each be moved in 3-dimensional space. Therefore, as in the geometry of FIG. 6, the tool support shaft 11 can be moved in the z-axis direction without employing a separate shaft insertion actuator.

The geometry of FIG. 7 can employ a simpler structure for joint 128 than for joint 124 in the geometry of FIG. 6, and friction associated with translational movement of joint 124 of FIG. 6 with respect to the sixth link 113 can be eliminated. Therefore, the geometry of FIG. 7 may be capable of producing more delicate movements of the tool support shaft 11 than can the geometry of FIG. 6.

The arrangements of FIGS. 6 and 7 can be modified to replace the rotary actuators 101, 120 with linear actuators which can translate the first link 103 in a direction transverse (such as perpendicular) to the paths of movement of the first and second linear actuators 104, 105 and can translate the seventh link 121 in a direction transverse (such as perpendicular) to the path of movement of the third linear actuator 122.

Figure 8:
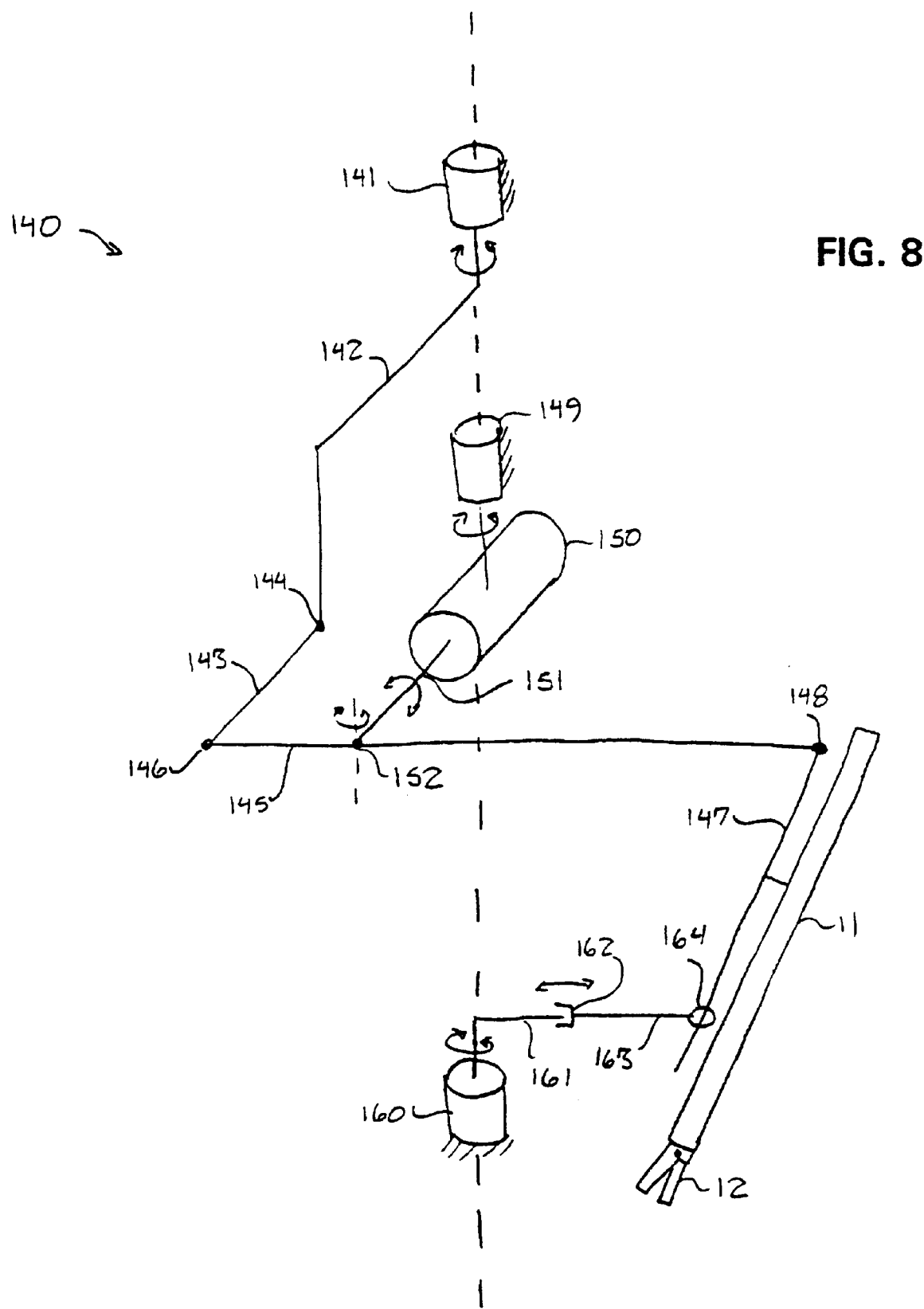
FIG. 8 is a schematic representation of still another form of a manipulator according to the present invention.

FIG. 8 schematically illustrates the geometry of another shaft support structure 140 of a manipulator according to the present invention. This shaft support structure 140 can manipulate one joint for supporting a tool support shaft 11 in three-dimensional space and another joint in two-dimensional space. A first rotary actuator 141 having a rotational axis is mounted on a stationary support, such as a frame or base. A first link 142 has one end connected to the first rotary actuator 141 and a second end connected to the first end of a second link 143 by a joint 144 spaced from the rotational axis of the first rotary actuator 141. The second end of the second link 143 is connected to the first end of a third link 145 by a joint 146. The second end of the third link 145 is pivotably connected to one end of a fourth link 147 by a joint 148 for the tool support shaft 11. The tool support shaft 11 is secured to the fourth link 147. A second rotary actuator 149 rotates a third rotary actuator 150 about a rotational axis. For simplicity of kinematics, the rotational axes of the first and second rotary actuators 141, 149 are aligned, but they need not be either aligned or parallel. The third rotary actuator 150 rotates a fifth link 151 about a rotational axis which is transverse (such as perpendicular) to the rotational axis of the second rotary actuator 149. The fifth link 151 is connected to the third link 145 by a joint 152 which has one rotational degree of freedom about an axis which is transverse (such as perpendicular) to the rotational axis of the third rotary actuator 150 and perpendicular to the axis of link 145. A fourth rotary actuator 160 having a rotational axis is mounted on a stationary support. In FIG. 8, the rotational axis of the fourth rotary actuator 160 is aligned with those of the first and second rotary actuators 141, 149, but the axes need not be aligned or parallel. A sixth link 161 has one end secured to the fourth rotary actuator 160 and a second end secured to a linear actuator 162 which acts in a straight line. In the present example, the path of movement of the linear actuator 162 is perpendicular to the rotational axis of the fourth rotary actuator 160 so that any point on link 163 will move in a plane, but it is instead possible for the path of movement to be non-perpendicular to the rotational axis of the fourth rotary actuator 160. A seventh link 163 has one end secured to the linear actuator 162 and another end secured to a second joint 164 pivotably connected to the fourth link 147. Joint 148 is fixed against translation with respect to the fourth link 147 in the lengthwise direction thereof. Furthermore, joints 148 and 164 are arranged so that the distance between them can vary. For example, joint 164 may be capable of translating with respect to the fourth link 147 in the lengthwise direction thereof, or joint 164 may be fixed against translation with respect to the fourth link 147, and the fourth link 147 may have a telescoping structure. Each of joints 148, 164 permits the fourth link 147 to pivot with respect to the third or seventh link 145, 163 with at least two rotational degrees of freedom. The fourth link 147 and the joints 148, 164 are further arranged such that the angle between links 145 and 163 measured about the axis of the fourth link 147 can vary. For example, one of the joints 148, 164 may provide three rotational degrees of freedom, or the joints 148, 164 may have two rotational degrees of freedom and an additional rotational joint (a roll joint) may be incorporated into the fourth link 147 to divide the fourth link 147 into two sections which can rotate with respect to each other about the longitudinal axis of the fourth link 147.

Many different structures can be employed for joints 144 and 146. For example, both joints may have three rotational degrees of freedom (e.g., two spherical joints or their equivalents), one joint may have two rotational degrees of freedom (e.g., a gimbals joint or its equivalent) while the other joint has three rotational degrees of freedom (e.g., a spherical joint or its equivalent), or both joints may have two rotational degrees of freedom (e.g., two spherical joints or their equivalents) and another joint (a roll joint) may be built into the second link 143 to permit two sections of the second link 143 to rotate with respect to each other about the longitudinal axis of the second link 143.

Of the five actuators employed in this arrangement, three are stationary, and the third rotary actuator 150 and the linear actuator 162 can be disposed so that their centers of gravity are as close as possible to the rotational axes of the second and fourth rotary actuators 149, 160, respectively, so their moments of inertia about these axes can be minimized. Therefore, the shaft support structure 140 as a whole can have a low inertia which is desirable from the standpoint of increasing the dexterity of the manipulator.

The first, second, and third rotary actuators 141, 149, 150 can together move joint 148 to an arbitrary position in three-dimensional space, while the fourth rotary actuator 160 and the linear actuator 162 can together move joint 164 to an arbitrary position in two-dimensional space. By appropriate control of the locations of joints 148 and 164, the tool support shaft 11 can be kept aligned with a virtual pivot point, and the tool support shaft 11 can be moved in the z-axis direction without the need for a shaft insertion actuator.

In a manner similar to the way the embodiment of FIG. 6 can be modified to obtain the embodiment of FIG. 7, the embodiment of FIG. 8 can be modified to replace link 163 with two links pivotably connected to each other (corresponding to links 125 and 126 of FIG. 7) and to replace the second joint 164 with a joint corresponding to joint 128 of FIG. 7 which is fixed against translation with respect to link 147.

A shaft support structure according to the present invention is not restricted to the orientations shown in FIGS. 3–8 and may assume any desired orientation with respect to the vertical. For example, in the arrangement of FIG. 6, the orientation could be reversed by 180 degrees so that the first rotary actuator 101 and the first and second linear actuators 104, 105 are below the second rotary actuator 130 and the third linear actuator 122.

The linear and rotary actuators employed in the arrangements of FIGS. 3–8 are not restricted to any particular type. Examples of linear actuators which can employed include linear electric motors, rotary motors connected to motion converting mechanisms (such as ball screws or racks and pinions) for converting rotary to linear motion, and hydraulic or pneumatic cylinders. When the tool support shaft only needs to assume a small number of orientations, linear actuators having only a small number of discrete states, such as a solenoid, can be used, but when it is desired to manipulate the tool support shaft over a continuous range of angles with respect to the vertical, the linear actuators preferably permit substantially continuous position and force control. Among various types of linear actuators, linear electric motors are particularly suitable, especially for applications in which precise control of the tool support shaft angle is desired. Linear motors produce a linear output force, so they can be used to directly drive portions of the shaft support structure without the need for ball screws, cables, or other motion converting mechanisms (which produce backlash, increased inertia, and increased friction, all of which are detrimental to precise control of the tool support shaft). Thus, linear motors enable the tool support shaft to be manipulated with high precision. In addition, the moving mass of a linear motor is essentially independent of the range of movement of the moving portion of the motor. In contrast, for most other types of linear actuators, including hydraulic cylinders or motors connected to ball screws, an actuator with a long range of movement will tend to have a greater moving mass undergoing rotation and/or translation than an actuator with a short range of movement. Therefore, linear motors employed as linear actuators can have a long range of movement while still having a low moving mass and low inertia. Still another advantage of linear motors is that they have very low friction, which, together with low moving mass and low inertia, is highly advantageous from the standpoint of achieving accurate force control and/or position control as well as smooth movement. This low friction results in linear motors being backdrivable, i.e., they can be driven by an external force exerted in the direction opposite to the direction of the force exerted by the motor. Backdrivability is useful in a surgical manipulator because it enables the manipulator to be compliant. Thus, if a patient moves during surgery due to an involuntary muscle motion, for example, and exerts a force on some portion of the manipulator, the actuators can be backdriven to enable the manipulator to move under the force applied by the patient rather than acting as a rigid object. Therefore, backdrivability increases the safety of a manipulator. A particularly preferred example of a linear actuator is a permanent magnet DC linear motor such as those manufactured by Trilogy Systems of Webster, Tex., and Northern Magnetics of Santa Clarita, Calif., although many other varieties and brands of linear motors can be employed, such as AC vector drive linear motors. In the illustrated embodiments, linear motors employed in the present invention have a stationary magnet track and a moving coil unit movable along the magnet track, but it is also possible to employ motors having a moving magnet and a stationary coil unit.

The rotary actuators are also not restricted to a specific type. Brushless slotless DC motors are particularly suitable to avoid or minimize torque ripple and cogging, but other types, such as stepper motors, can also be used. When a motor is used as a rotary actuator, the motor is preferably directly connected to a link which is to be rotated in order to reduce backlash, friction, and inertia and improve the ability to directly control the torque applied by the motor, but it is also possible to dispose a reduction gear between the motor and the link.

The various actuators may be equipped with sensors for sensing the positions of the moving portions of the actuators or the members moved by the actuators and thereby enable a determination of the locations of the joints for the tool support shaft. A wide variety of conventional sensors can be used to sense the positions mechanically, magnetically, optically, or in another manner. A few examples of suitable sensors are potentiometers, linearly variably differential transformers, optical encoders, and Hall effect sensors. When fine positional control of a linear actuator is desired, a holographic interferometric linear encoder is particularly suitable for use as a position sensor because it can sense position with a resolution of as fine as 10 nanometers. An example of a holographic interferometric linear position sensor which may be employed is one manufactured by MicroE, Inc. of Natick, Mass. Such a linear position sensor includes an elongated position scale and a position reader having a slot in which the position scale can be movably disposed. Either the position scale or the position reader can be mounted on a moving portion of the linear actuator, and the other of the two can be mounted on a stationary member. The position reader generates an electrical output signal which indicates the location of the position scale relative to the position reader. An example of a suitable position sensor for use with the rotary actuators is a holographic interferometric optical rotary encoder manufactured by MicroE. Inc.

Similarly, the various actuators can be equipped with sensors for sensing the forces or torques applied by the actuators and thereby enable a determination of the forces and torques applied to the tool support shaft. This sensory information can be used in a feedback control loop to control the forces and torques applied to the tool support shaft, and/or, when used in conjunction with an input control device capable of generating forces, to provide feedback of these forces and torques to the surgeon or operator who is controlling the shaft support structure.

Any known method for measuring forces and/or torques can be employed to sense the forces or torques applied by the actuators. One example of a suitable method is to apply strain gages to structural members.

Figure 9:
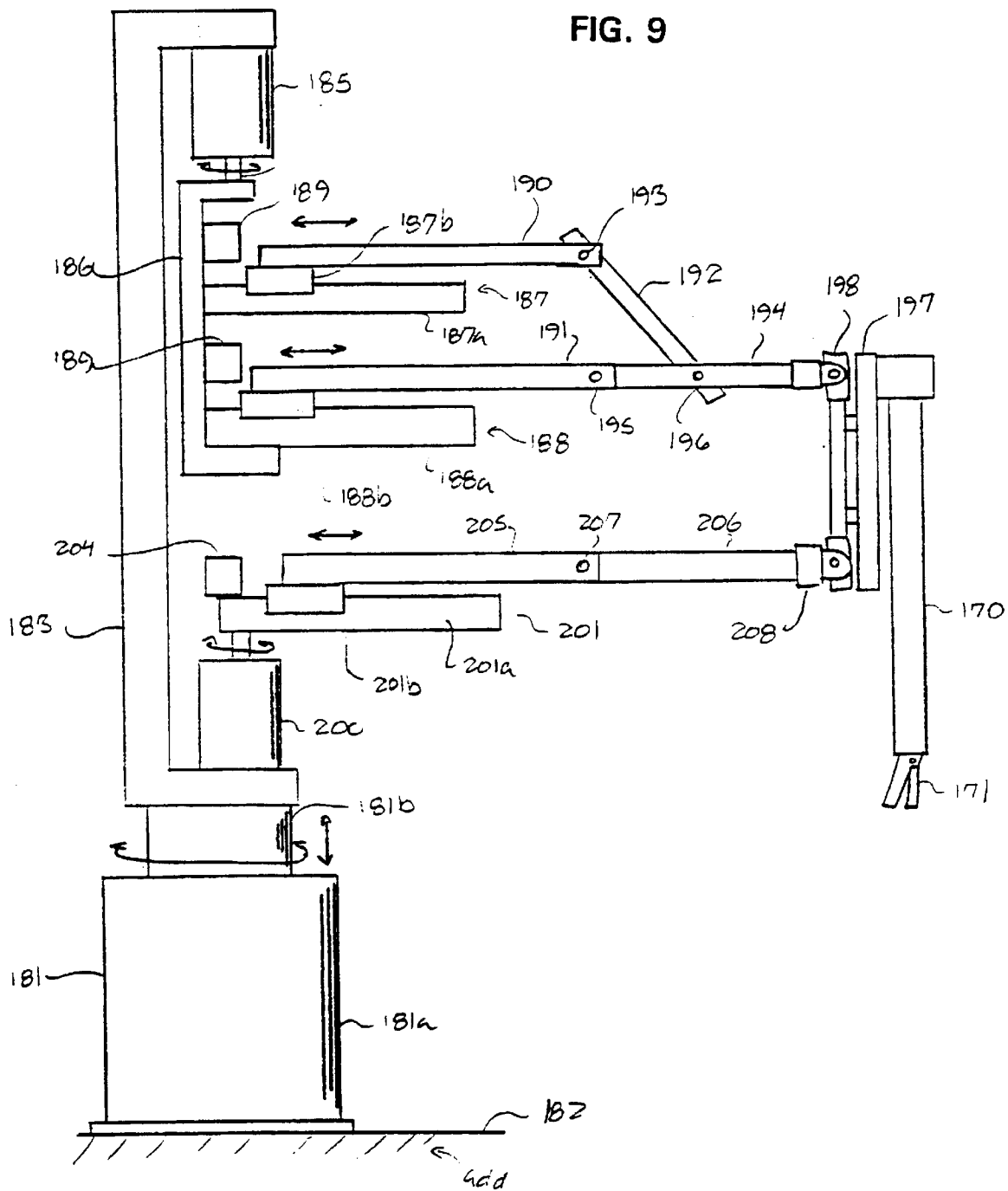
FIG. 9 is a schematic elevation of an embodiment of a manipulator according to the present invention having the geometry illustrated in FIG. 7.

FIG. 9 schematically illustrates an embodiment of a manipulator according to the present invention having the geometry illustrated in FIG. 7 and which can move two joints in three-dimensional space. The manipulator includes a tool support shaft 170 having a surgical tool 171 mounted at one end, and a shaft support structure 180 which supports the tool support shaft 170 and is capable of manipulating the tool support shaft 170 with multiple degrees of freedom.

The shaft support structure 180 includes a support base 181 which is shown sitting on a floor 182. The base 181 may be equipped with rollers or similar members to give it mobility, or it may be a stationary member. A support frame 183 is mounted on the base 181. To increase the range of motion of the tool support shaft 170, the base 181 may be equipped with a mechanism for raising and lowering or otherwise moving the support frame. For example, it may include a stationary lower portion 181a and an upper portion 181b which can be raised and lowered and/or rotated about a vertical axis with respect to the lower portion 181a. The upper portion 181b can be raised and lowered by any suitable arrangement, such as hydraulic cylinders, pneumatic cylinders, or an electric motor drivingly connected to the upper portion 181b, such as through a pinion engaging a rack formed on the upper portion 181b. When the upper portion 181b is rotatable with respect to the lower portion 181a, it may be rotated by a drive mechanism, such as a motor, or it may be manually rotatable. A mechanical lock may be provided to releasably prevent the upper portion 181b from rotating when desired.

The frame 183 supports first and second arms having first and second rotary actuators 185, 200 comprising brushless DC motors having rotational axes which are aligned with each other. Each rotary actuator may be equipped with an unillustrated encoder or other type of rotational position sensor for sensing the rotational position of its output shaft. It may also be equipped with a torque sensor to sense the output torque of the actuator.

The output shaft of the first rotary actuator 185 is connected to a frame 186 on which first and second linear actuators 187, 188 are mounted. The first linear actuator 187 can translate a first link 190 in the lengthwise direction of the first link 190, and the second linear actuator 188 can translate a second link 191 in the lengthwise direction of the second link 191. Both linear actuators 187, 188 act in a direction perpendicular to the rotational axis of the first rotary actuator 185. One end of the first link 190 is pivotably connected to a first end of a third link 192 by a joint 193, and one end of the second link 191 is pivotably connected to the first end of a fourth link 194 by a joint 195. The second end of the fourth link 194 is pivotably connected to a support frame 197 by a joint 198, and the second end of the third link 192 is pivotably connected to the fourth link 194 between its two ends by a joint 196.

The second rotary actuator 200 rotates a third linear actuator 201 about the rotational axis of the second rotary actuator 200. The third linear actuator 201 can translate a fifth link 205 in a direction perpendicular to the rotational axis of the second rotary actuator 200. One end of the fifth link 205 is pivotably connected to the first end of a sixth link 206 by a joint 207. The second end of the sixth link 206 is pivotably connected to the support frame 197 by a joint 208.

Each of the linear actuators 187, 188, 201 is a brushless linear DC motor having an elongated magnet track 187a, 188a, 201a and a coil unit 187b, 188b, 201b which can translate along the magnet track, although as stated above, the coil units may be stationary and the magnet tracks may translate with respect to the coil units. Each coil unit may be directly supported by the corresponding magnet track or by a bearing incorporated into the linear motor, or it may be supported by a member formed separately from the linear motor, such as a linear bearing extending parallel to the magnet track. A ball slide or recirculating linear slide is particularly suitable as a linear bearing because it can have an extremely low coefficient of friction. Examples of suitable ball slides are those available from THK Co. Ltd. of Japan and Deltron Precision, Inc. of Bethel, Conn. A low coefficient of friction for a linear guide is highly advantageous because it enables the linear motors (and therefore the joints for the tool support shaft) to be moved in extremely fine increments, resulting in the orientation of the tool support shaft being controllable with a high degree of precision and being passively backdrivable. Low friction also enhances the ability of a control system to control the forces applied to the tool support shaft 170. Each of the first, second, and fifth links is schematically shown being cantilever supported by one of the coil units, but the links may be supported in any other suitable manner. For example, each link may be supported by the moving portion of a linear bearing in the same way as the coil units may be.

Each of joints 198 and 208 provides at least two rotational degrees of freedom of the support frame 197 with respect to the fourth and seventh links 194, 206 so that the support frame 197 can pitch and yaw with respect to these links. In addition, one of the joints 198, 208 may provide three rotational degrees of freedom so that the support frame 197 can roll with respect to one of links 194 and 206. For example, one of the joints can be a gimbals joint or its equivalent while the other joint is a spherical joint or its equivalent. Alternatively, both joints 198, 208 can have two rotational degrees of freedom, and a roll joint can be incorporated into the support frame 197 two permit two sections of the support frame 197 to rotate with respect to each other about the longitudinal axis of the support frame 197.

The tool support shaft 170 is shown as being stationary with respect to the support frame 197, but it may instead be movable. As described in further detail below, it may be advantageous if the tool support shaft 170 is readily detachable from the support frame 197 to enable the tool support shaft 170 to be easily replaced or sterilized. The longitudinal axis of the tool support shaft 170 is shown as being offset from a line connecting the centers of joints 198 and 208, but it could be coincident with this line.

To simplify the structure and the kinematics of the manipulator, all of the links are straight members and the first, second, and fifth links 190, 191, and 205 are moved by the corresponding linear actuators in parallel planes perpendicular to the plane of the drawing. However, the shape of the links is arbitrary, and the first, second, and fifth links may move in non-parallel planes.

If the rotational axes of the rotary actuators 185, 200 are coaxial with each other, the tool support shaft 170 can be swung about these axes without changing the positions of the links with respect to each other, either by simultaneous operation of the rotary actuators 185, 200 in the same direction or by hand with the rotary actuators turned off. Locking members may be provided to prevent the movement of the links with respect to each other when the tool support shaft 170 is being swung in this manner. For example, the coil units 187*b*, 188*b*, 201*b* of the linear motors could be equipped with locking mechanisms to enable them to be releasably immobilized with respect to the corresponding magnet tracks. If the rotary actuators 185, 200 have nonaligned axes, it may be desirable to make the upper portion 181*b* of the base 181 rotatable about a vertical axis with respect to the lower portion, in which case the tool support shaft 170 can be rotated about a vertical axis by rotating the upper portion 181*b* of the base 181 and all the members supported by it.

Linear actuators 187, 188 may be subjected to some degree of gravity loading from the weight of the tool support shaft 170 and any additional actuators or other components mounted on it. This gravity loading may be supported entirely by the actuators 187 and 188, or a counterbalancing mechanism can be added between the links 190, 191 and the frame 186 to counterbalance this load. Any known counterbalancing mechanism can be employed for this purpose, including constant force springs, low friction air cylinders, and similar devices.

Figure 23:
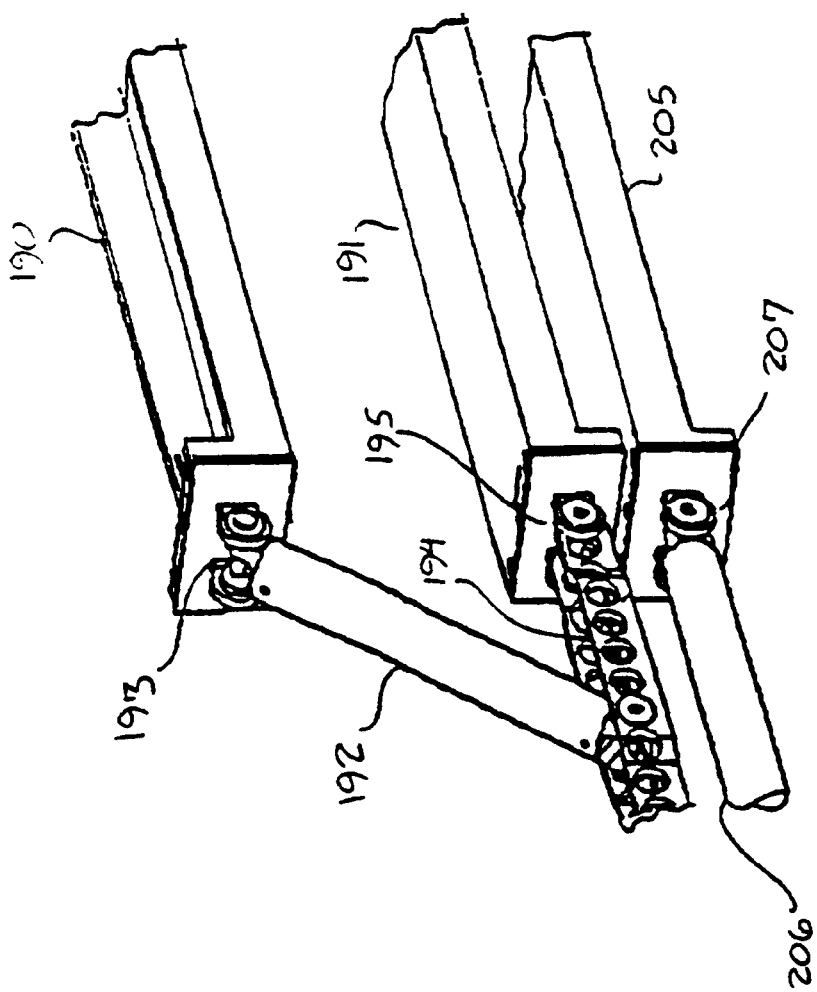
FIG. 23 is an isometric view of a portion of the embodiment of FIG. 9.
Figure 24:
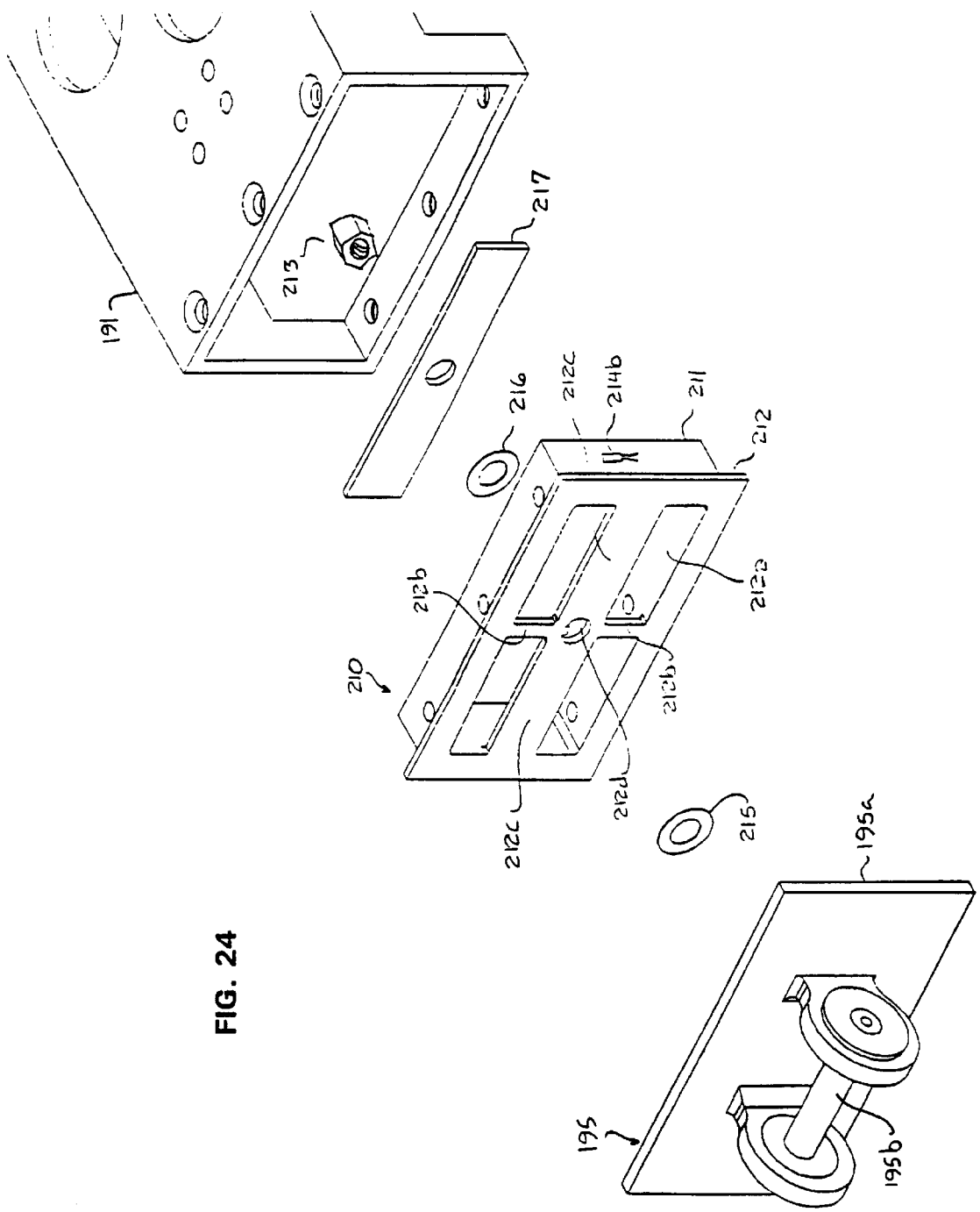
FIG. 24 is an exploded isometric view of one of the links of the portion shown in FIG. 23.
Figure 25:
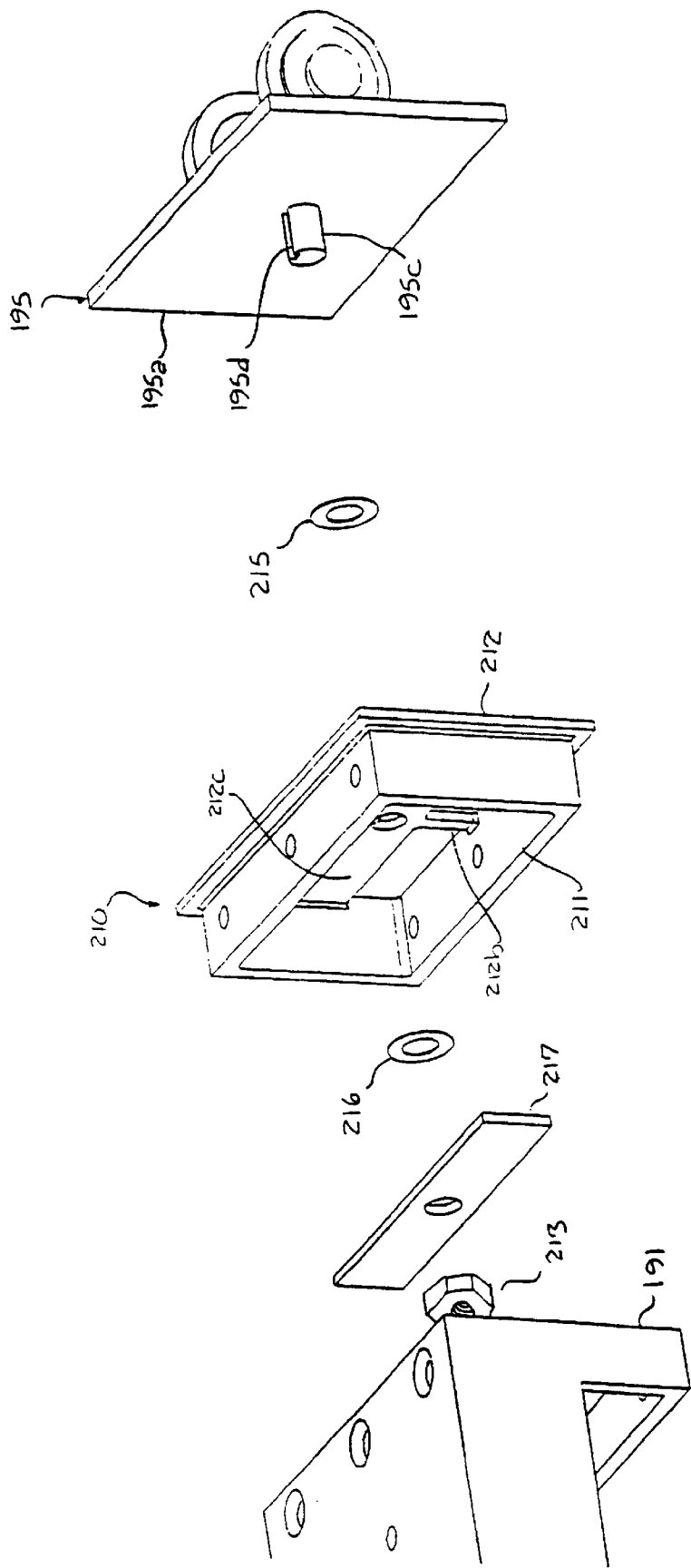
FIG. 25 is an exploded isometric view from a different angle of the portion shown in FIG. 23.
Figure 26:
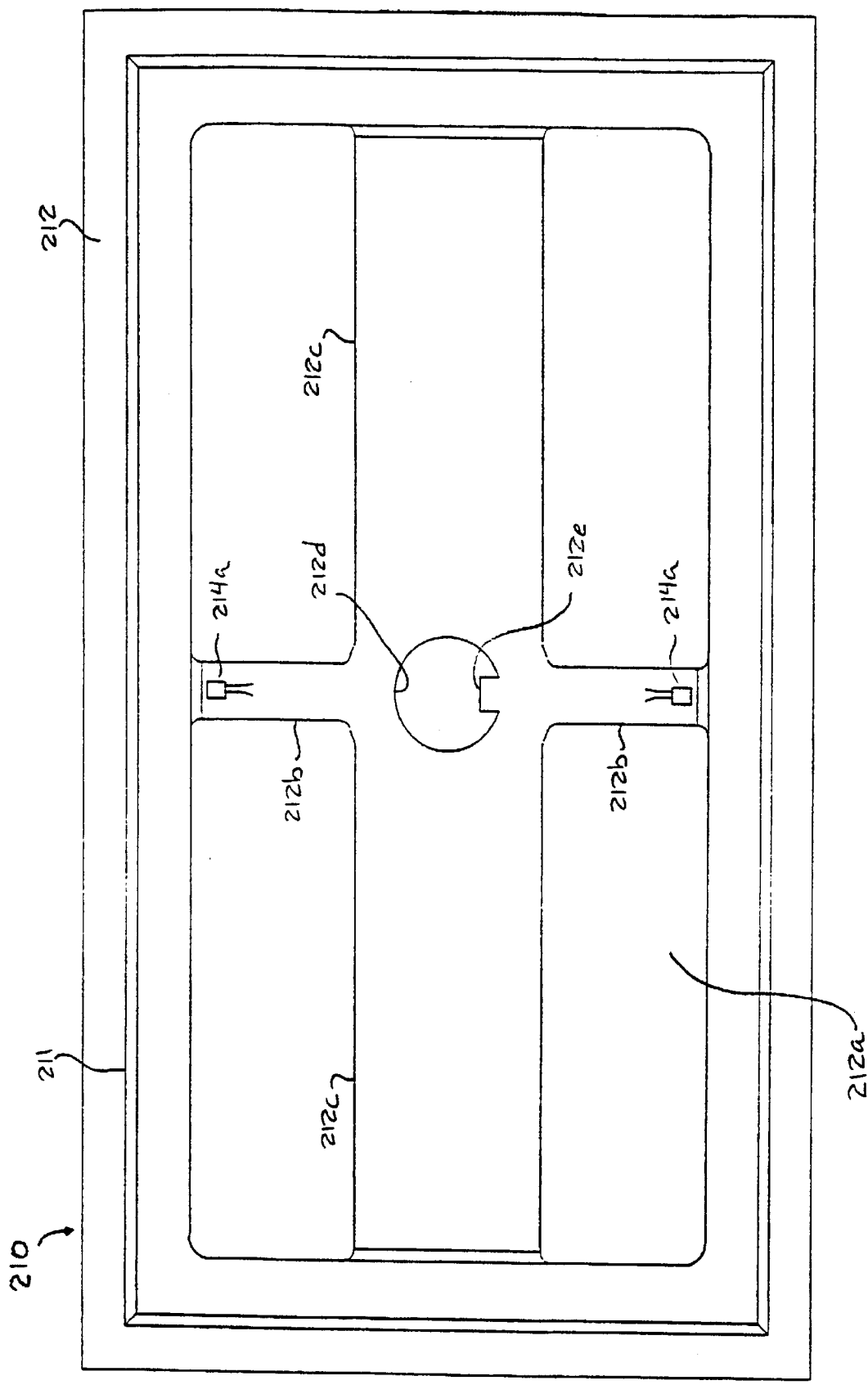
FIG. 26 is a rear elevation showing the location of strain gages on the frame of the portion shown in FIG. 23.

Force sensors may be installed in various locations to sense the forces exerted by the actuators or the forces acting on various portions of the manipulator. In the present embodiment, each of joints 193, 195, and 207 is equipped with a force sensor for sensing the axially force exerted by each of the linear actuators 187, 188, and 201. FIG. 23 is an isometric view of a portion of the links connected to joints 193, 195, and 207, and FIGS. 24–26 are views of various portions of the force sensor for joint 195. The force sensors for joints 193 and 207 may be of similar structure. As shown in these figures, joint 195 includes a plate 195*a* having a shaft 195*b* supported on one side thereof for rotatably engaging bearings mounted on the end of link 194. Joint 195 is supported by link 191 through a frame 210 upon which one or more strain gages are mounted for sensing strains resulting from axial forces applied to link 191. The frame 210 has an outer rectangular rim 211 which is secured to link 191 by bolts, welding, or other suitable means. The frame 210 also includes a plate 212 which is secured to the rim 211 (for example, the rim 211 and the plate 212 may be integrally formed with each other or separate members) and has a plurality of openings 212*a* which define a plurality of legs. The illustrated plate 212 has two vertical legs 212*b* and two horizontal legs 212*c* which intersect the vertical legs 212*b* in the shape of a cross. The joint 195 is connected to the frame 210 such that forces applied to the joint 195 can be resisted by the legs. For example, the illustrated joint 195 has a shaft 195*c* which extends from the side of the plate 195*a* opposite from shaft 195*b* and passes though an opening 212*d* in the center of plate 212 of the frame 210. Shaft 195*c* can be secured to the plate 212 by a nut 213 or other fastener, by bonding, or other desired method which enables forces applied to the joint 195 to be transmitted to the frame 210. The shaft 195*c* may have a portion which interfits with the opening 212*d* in the frame 210 to ensure proper alignment of the joint 195 with respect to the frame 210. For example, the illustrated shaft 195*c* has a slot 195*d* which engages with a projection formed in the opening 212*d*.

Any desired number of strain gages can be mounted on the frame 210 for use in measuring applied loads. In the present embodiment, two strain gages 214*a* for sensing strains due to applied forces (which will be referred to as load sensing strain gages) are mounted on the rear surface (the surface facing link 191) of the vertical legs 212*b* as shown in FIG. 26, and two more strain gages 214*b* (only one of which is shown) for temperature compensation are mounted on portions of the frame 210 which are substantially stress free during operation of the manipulator, such as on the vertical side surfaces of the outer rim 211 of the frame 210. The other temperature compensation strain gage 214*b* may be mounted on the vertical side surface on the opposite side of the rim 211, for example. The four strain gages 214*a*, 214*b* can be connected to each other to form a Wheatstone bridge, with each of the strain gages 214*a* on the vertical legs 212*b* connected electrically in series with one of the temperature compensation strain gages 214*b*. A voltage can be applied to the Wheatstone bridge in a conventional manner, and the output signal of the Wheatstone bridge will be indicative of the strains experienced by the strain gage.

When a force is applied to the center of the frame 210 in the longitudinal direction of link 191, each of the load sensing strain gages 214*a* will be put equally into tension or compression, and the output of the Wheatstone bridge will be proportional to the applied force. If a force is applied to the center of the frame 210 in the direction of the axis of the vertical legs 212*b*, one of the load sensing strain gages 214*a* will be in tension while the other will be in compression. The signals from the two load sensing strain gages 214*a* will cancel each other out, and the output of the Wheatstone bridge will be substantially zero. If a bending moment about the axis of the horizontal leg is applied to the frame 210, the load sensing strain gages 214*a* will be strained equally and oppositely, so in this case as well the output of the Wheatstone bridge will be substantially zero. A torque applied about the longitudinal axis of link 191, a torque applied about the axis of the vertical legs 212*b*, or a force acting along the axis of the horizontal legs 212*c* will not produce any substantial deformation of the load sensing strain gages 214*a*, so substantially will not effect the output of the Wheatstone bridge. Thus, the illustrated arrangement can sense forces in the axial direction of link 191, which are the forces exerted by linear actuator 181, and can ignore all other forces acting on link 191 or joint 195.

The frame 210 is not restricted to any particular shape, and it need not be formed with openings 212a or legs 212b, 212c. However, the illustrated configuration, with two vertical legs 212b and two horizontal legs 212c, is a convenient one because, due to its geometric simplicity, axial loads acting on the joint 195 can be calculated in a straightforward manner from the strains measured by the load sensing strain gages 214a.

In the range of strains capable of being safely measured by the load sensing strain gages 214a, it is preferable for the load applied to the frame 210 by the joint 195 to be localized at the center of the frame 210 so that the load will be resisted substantially entirely by the legs of the frame 210 rather than by the periphery of the frame 210, since it is easier to calculate the relationship between the measured strains and the applied load in this case. However, if the deformation of the frame 210 by the applied load becomes too large, the load sensing strain gages 214a on the legs 212b or the frame 210 itself may be damaged.

The illustrated force sensor is constructed such that the portion of the frame 210 to which loads are applied increases in area as the magnitude of deformation increases to prevent such damage. As shown in FIGS. 24 and 25, which are exploded isometric views of the force sensor, two spacers 215 and 216, such as washers, are disposed around the shaft 195c of the joint 195 on opposite sides of the plate 212 of the frame 210, and a member having a larger surface area than the inner spacer 216, such as a plate 217, is mounted on the shaft 195c adjoining the inner spacer 216. When no loads are acting the joint 195, the two spacers 215, 216 keep the plate 195a of joint 195 and the plate 217 spaced from the plate 212 of the frame 210. When a load below a certain level is applied to the joint 195 in either axial direction of link 191, the plate 195a of joint 195 and the plate 217 do not contact the frame 210, so loads are applied to the frame 210 only in the region near opening 212d, and loads are resisted substantially entirely by the legs of the frame 210. When an axial load on the frame 210 reaches a higher level, which is selected to be lower than a level which will cause damage to the strains gages 212b or the frame 210, the plate 195a of joint 195 will contact the plate 212 of the frame 210 and the axial load will be distributed over a larger region of the frame 210, including, for example, the periphery of the plate 212 surrounding the legs, thereby preventing deformation of the frame 210 from reaching a level resulting in damage. Similarly, when a load on the frame 210 in the opposite axial direction reaches a certain level which is selected to be lower than a level which will cause damage to the strain gages 212b or the frame 210, the plate 217 will contact the inner side of the plate 212 (such as the horizontal legs 212c and/or the periphery of the plate 212) and distribute the axial load over a larger portion of the plate 212 to prevent damage to the strain gages 212b or the frame 210.

Many other arrangements can be used to sense forces acting on or applied by the manipulator. For example, strain gages or other force sensors can be mounted directly on the actuators or links of the manipulator.

Figure 10:
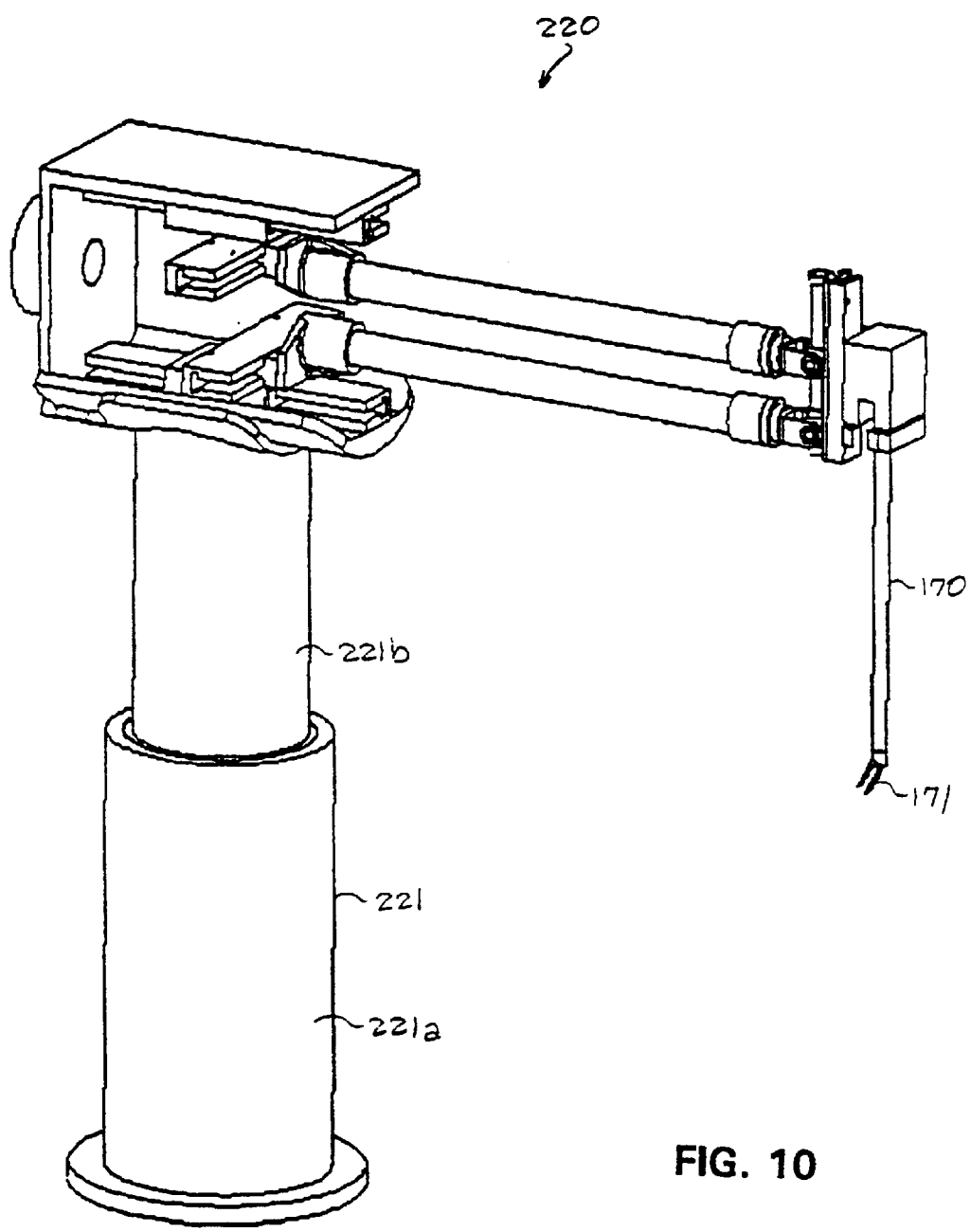
FIG. 10 is an isometric view of another embodiment of a manipulator according to the present invention having the geometry illustrated in FIG. 5.
Figure 11:
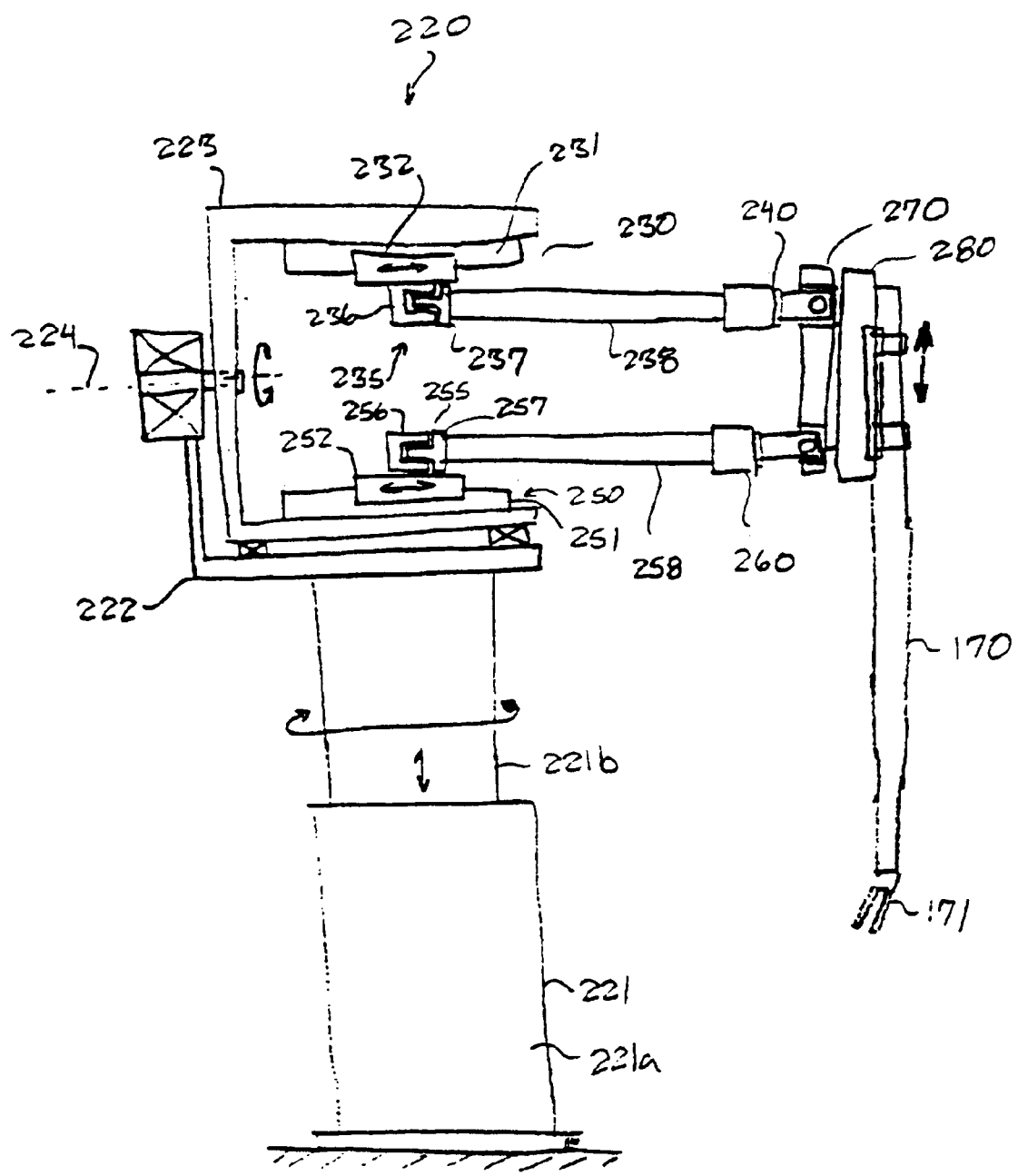
FIG. 11 is a schematic side elevation of the embodiment of FIG. 10.
Figure 12:
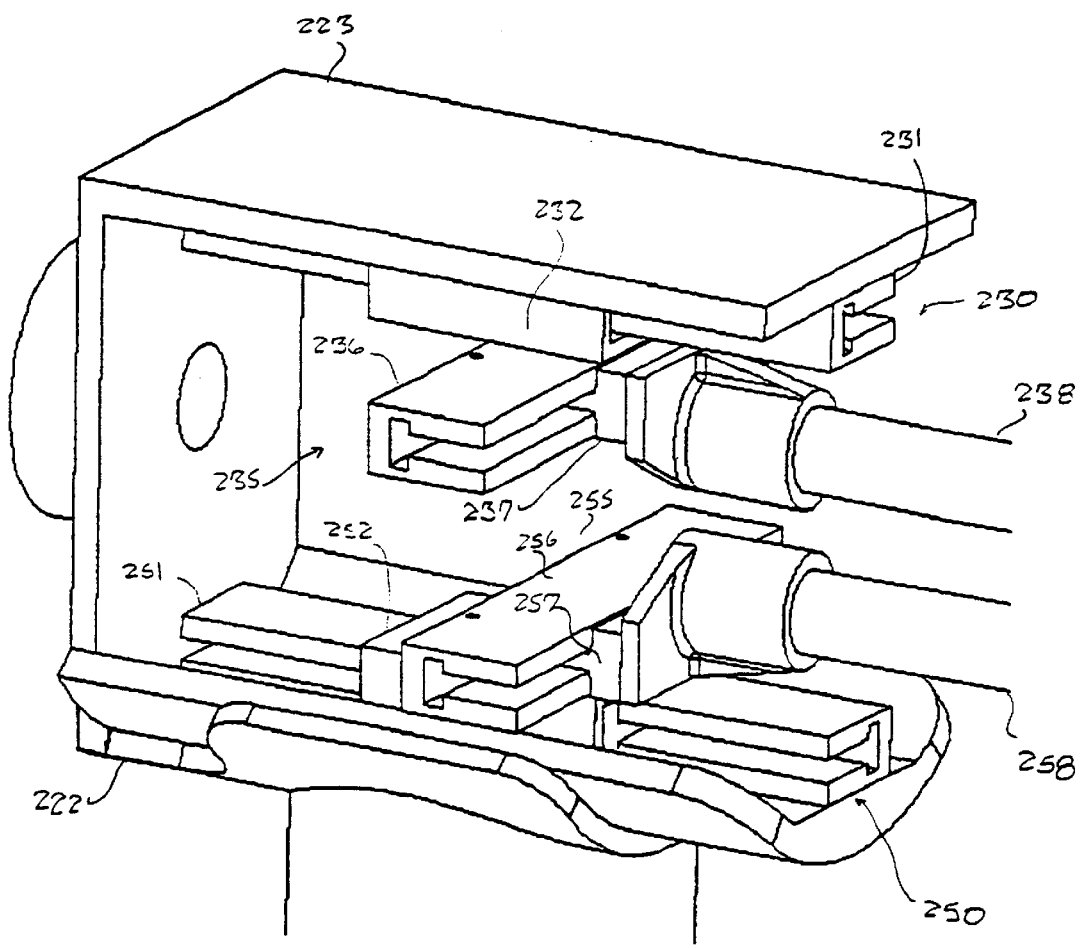
FIG. 12 is an enlarged view of the linear actuators of the embodiment of FIG. 10.
Figure 13:
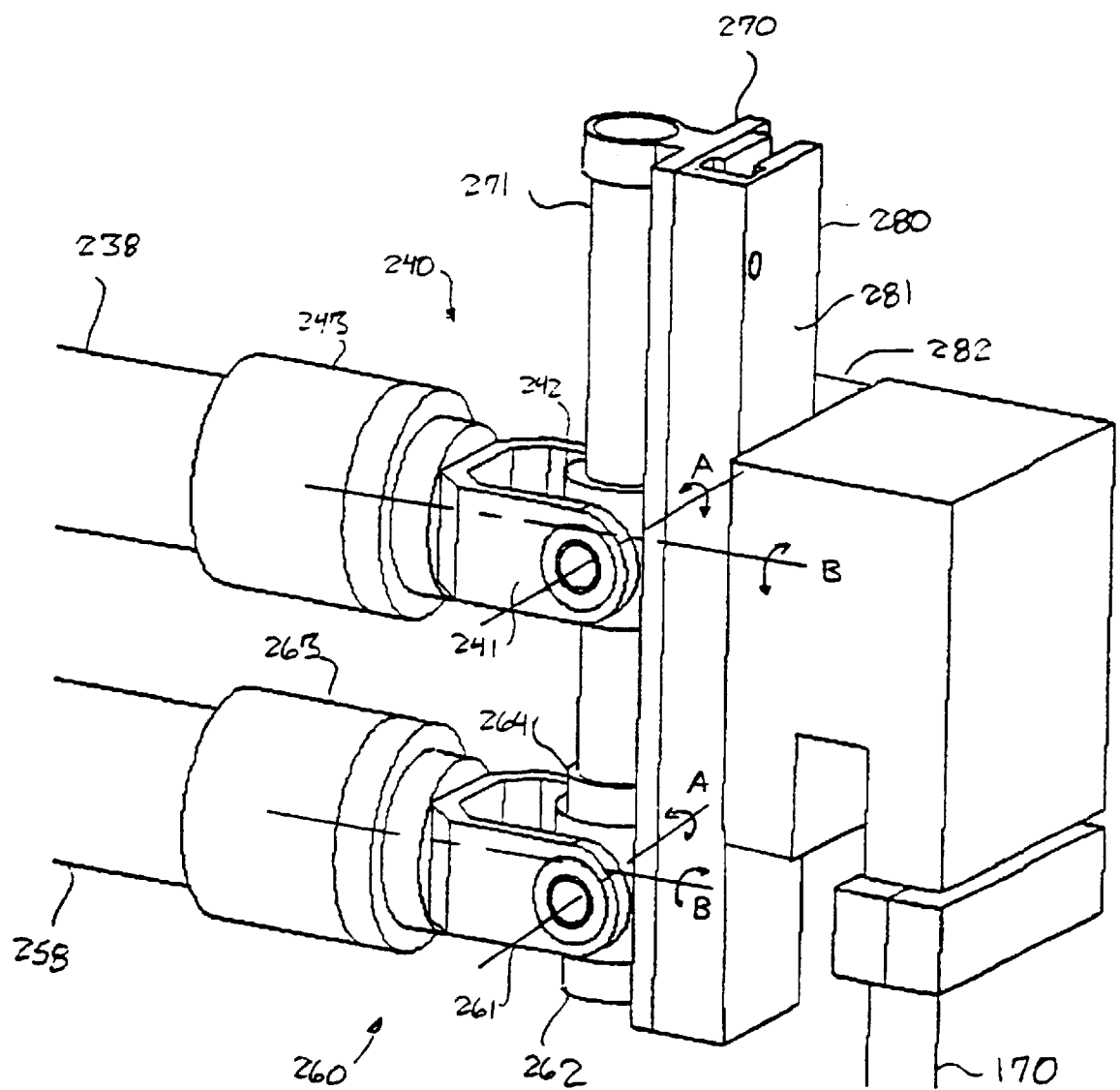
FIG. 13 is an enlarged isometric view of the shaft insertion actuator of the embodiment of FIG. 10.

FIGS. 10–13 illustrate an embodiment of a manipulator according to the present invention having a geometry like that illustrated in FIG. 5. FIG. 10 is an isometric view of this embodiment, FIG. 11 is a side elevation, FIG. 12 is an enlarged view of the portion of the manipulator in the vicinity of the linear actuators, and FIG. 13 is an enlarged view of the portion of the manipulator supporting a tool support shaft. As shown in these figures, the manipulator includes a tool support shaft 170 having a tool 171 mounted at its lower end, and a shaft support structure 220 which supports the tool support shaft 170 for movement. The shaft support structure 220 includes a support base 221 which is disposed on a floor or other support surface. Like the support base 181 of the embodiment of FIG. 9, support base 221 may have movable portions. For example, it may include a stationary lower portion 221a and an upper portion 221b which can be raised and lowered and/or rotated about a vertical axis with respect to the lower portion 221a as described with respect to FIG. 9.

A first frame 222 is mounted atop the upper portion 221b of the base 221, and a second frame 223 is supported by the first frame 222 for rotation about an axis 224 which is horizontal in the figure but may be sloped with respect to a horizontal. The second frame 223 may be rotated either manually or by a motor or other drive mechanism mounted on one of the frames 222, 223. A lock may be provided on one of the frames 222, 223 for releasably locking the second frame 223 against rotation. The second frame 223 supports an upper set of linear actuators 230, 235 of a first arm and a lower set of linear actuators 250, 255 of a second arm by means of which the tool support shaft 170 can be translated and pivoted. The first set of actuators includes a first linear actuator 230 having a movable portion which can move in a straight line in a first direction and a second linear actuator 235 mounted on the movable portion of the first linear actuator and having a movable portion which can move with respect to the first linear actuator 230 in a direction transverse (such as perpendicular) to the first direction. A first link 238 is secured to the movable portion of the second linear actuator 235. Similarly, the second set of actuators includes a third linear actuator 250 having a movable portion which can move in a third direction and a fourth linear actuator 255 mounted on the movable portion of the third linear actuator 250 and having a movable portion which can move with respect to the third linear actuator 250 in a direction transverse (such as perpendicular) to the third direction. A second link 258 is secured to the movable portion of the fourth linear actuator 255. In this figure, the first and second directions are perpendicular to each other, the third and fourth directions are perpendicular to each other, the first direction is parallel to the third direction, and the second direction is parallel to the fourth direction so that the movable portions of the linear actuators all move in parallel planes. However, as described with respect to FIG. 5, the directions can be at other angles with respect to each other. The linear actuators may be of any desired type. In the illustrated embodiment, each linear actuator 230, 235, 250, 255 comprises a brushless linear electric motor having an elongated magnet track 231, 236, 251, 256 and a movable portion comprising a coil unit 232, 237, 252, 257 movable in a straight line along the magnet track. The magnet track 236 of the second linear actuator 235 is secured to the coil unit 232 of the first linear actuator 230, and the magnet track 256 of the fourth linear actuator 255 is secured to the coil unit 252 of the third linear actuator 250. In addition, the first link 238 is secured to the coil unit 237 of the second linear actuator 235, and the second link 258 is secured to the coil unit 257 of the fourth linear actuator 255. Each of the linear actuators may be equipped with an encoder or other position sensor for sensing the position of the coil unit of the actuator with respect to the magnet track. Each linear actuator may also be provided with a force sensor for sensing the output force of the actuator. Each of the coil units is shown as being supported solely by the magnet track of the corresponding motor, and the links 238, 258 are shown being supported solely by the coil units of the second and fourth linear actuators 235, 255. However, each of these members may be supported by members other than the linear actuators themselves, such as by separate linear bearings.

The ends of the first and second links 238, 258 remote from the linear actuators are connected to a support frame 270 by first and second joints 240 and 260, respectively, each of which can provide two rotational degrees of freedom of the support frame 270 with respect to the corresponding link. One of the joints 240, 260 may be capable of providing three rotational degrees of freedom, but since each link 238, 258 maintains a constant orientation in space, a third rotational degree of freedom is not needed. The distance between joints 240 and 260 is capable of varying. For example, one of the joints 240, 260 may be fixed against translation with respect to the support frame 270 while the other joint is capable of translation with respect to the support frame 270. Alternatively, both joints 240, 260 may be fixed against translation with respect to the support frame 270, and the portion of the support frame 270 connected to the joints 240, 260 may have a telescoping structure. The joints may be similar in structure to those of the embodiment of FIG. 9. In this example, the first joint 240 includes a yoke 241, which is pivotably connected to a sleeve 242 which slidably fits around a rod 271 of the support frame 270 for rotation about an axis A, and a collar 243, which is connected to the yoke 241 and fits over and is secured to an end of the first link 238. The collar 243 includes an internal bearing which rotatably supports the yoke 241 to enable the yoke 241 to rotate about an axis B perpendicular to axis A. The second joint 260 likewise includes a yoke 261 which is pivotably connected to a sleeve 262 and which is rotatably supported by a collar 263 which fits over and is secured to an end of the second link 258. The sleeve 262 is rotatably mounted on a bushing 264, a ball bearing, or similar member secured to the rod 271 of the support frame 270. The sleeve 262 can rotate on the bushing 264 about the longitudinal axis of the rod 271 but is prevented from translating in the lengthwise direction of the rod 271.

The support frame 270 supports a linear actuator 280 for shaft insertion which in turn supports the tool support shaft 170 for movement in a z-axis direction. The linear actuator 280 may be of any of the types described with respect to the preceding embodiments. The illustrated linear actuator 280 is a linear electric motor having an elongated magnet track 281 secured to the support frame 270 and a coil unit 282 movable along the magnet track 281 in the z-axis direction. The tool support shaft 170 is secured to the coil unit so as to be translated by it.

When the lower end of the tool support shaft 170 is inserted into a patient's body, the tool support shaft 170 will typically be manipulated solely by the linear actuators, whereas translation and/or rotation of the upper portion 221b of the base 221 and rotation of the second frame 223 with respect to the first frame 222 will typically used for coarse positioning of the tool support shaft 170 when the latter is not inserted into a patient's body. The ability of the second frame 223 to rotate with respect to the first frame 222 is particularly useful because it enables the tool support shaft 170 to assume any angle with respect to the vertical. For example, the tool support shaft 170 can be moved to a position in which it is horizontal or upside down with the tool 171 positioned higher than the rest of the tool support shaft 170.

Figure 14:
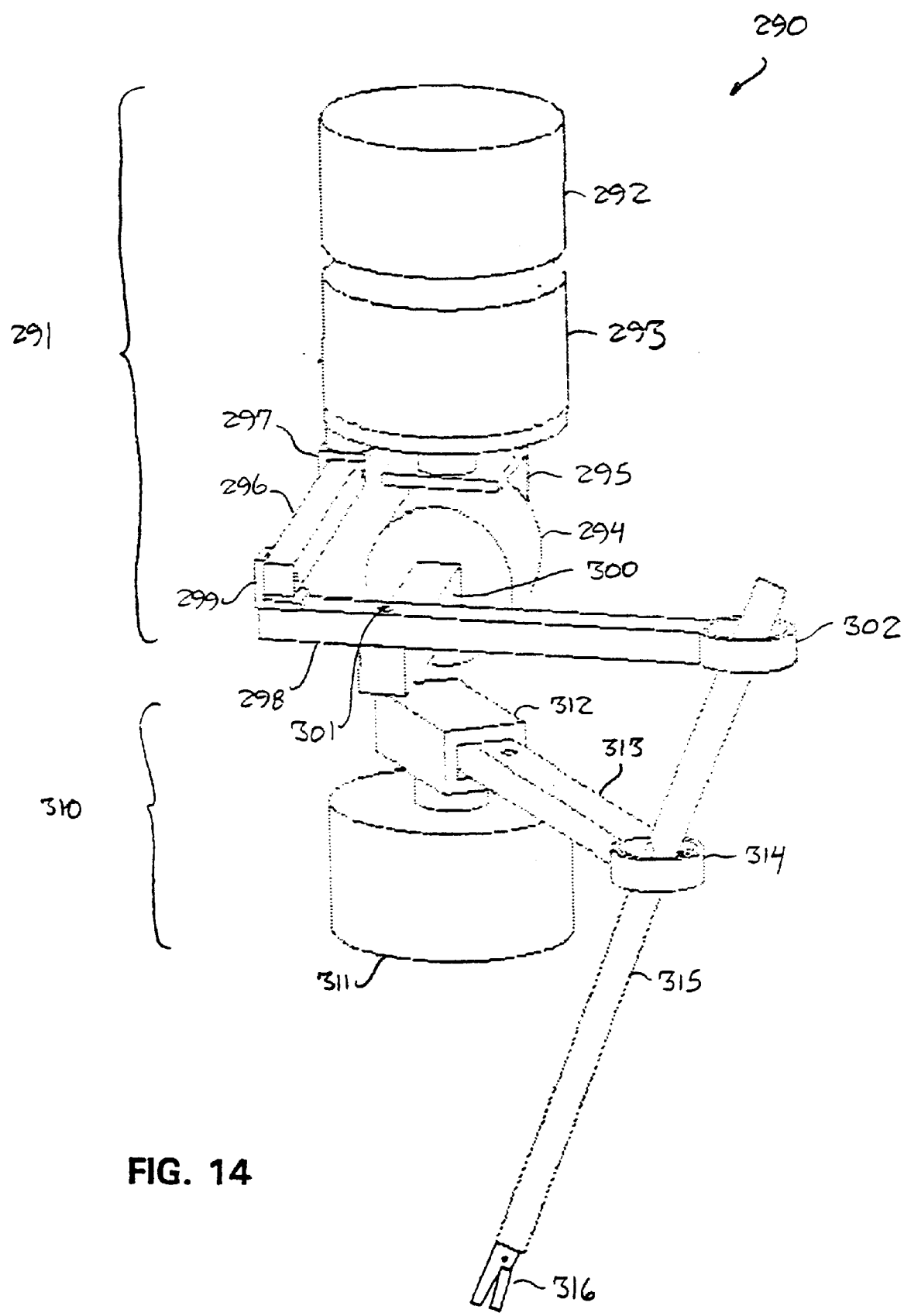
FIG. 14 is an isometric view of another embodiment of a manipulator according to the present invention having the geometry illustrated in FIG. 8.

FIG. 14 illustrates an embodiment of a manipulator according to the present invention having a geometry like that illustrated in FIG. 8. It includes a tool support shaft 315 supporting a tool 316 at its lower end and a shaft support structure 290 which movably supports the tool support shaft 315. The shaft support structure 290 includes an upper portion 291 capable of manipulating a joint for the tool support shaft 315 in three-dimensional space and a lower portion 310 capable of manipulating another joint for the tool support shaft 315 in two-dimensional space. The upper and lower portions 291, 310 are typically mounted on an unillustrated support structure, such as a base like those shown in FIGS. 9 and 10.

The upper portion 291 includes first through third rotary actuators 292, 293, 294 and first through third links 296, 298, 300. The first rotary actuator 292 can rotate a frame 295 supporting the third rotary actuator 294 about an axis. The second rotary actuator 293 is able to position a first end of the first link 296 at any point along an arc of a circle which is concentric with the rotational axis of the second rotary actuator 293. The third rotary actuator 294 can rotate the third link 300 about an axis perpendicular to the axis of the first and second rotary actuators 292, 293 and corresponding to the longitudinal axis of the third link 300. To enable the first and second rotary actuators 292, 293 to be stacked atop each other, the second rotary actuator 293 is preferably hollow so that the output shaft of the first rotary actuator 292 can extend through the second rotary actuator 293. For example, the second rotary actuator 293 can be a conventional hollow core motor having a rotor disposed around the core, while the first rotary actuator 292 can be a motor with a rotor at its center and an output shaft secured to the rotor and extending through the hollow core of the second rotary actuator 293. One end of the first link 296 is pivotably connected to the rotating portion of the second rotary actuator 293 by a joint 297 and the other end of the first link 296 is pivotably connected to one end of the second link 298 by another joint 299. One of the two joints 297, 299 is a spherical joint (such as a ball joint) or its equivalent while the other of the two joints is a universal joint (such as a Hooke's joint) or its equivalent. The outer end of the third link 300 is pivotably connected to the second link 298 between the two ends of the latter by a pin joint 301. The second end of the second link 298 is pivotably connected to the tool support shaft 315 by a joint 302 which is fixed against translation with respect to a tool support shaft 315. The lower portion 310 of the shaft support structure 290 includes a fourth rotary actuator 311 and a linear actuator 312 which can be rotated by the fourth rotary actuator 311 about its rotational axis. For simplicity of kinematics, the rotational axis of the fourth rotary actuator 311 is preferably aligned with the rotational axes of the first and second rotary actuators 292, 293, although it need not be. The linear actuator 312 can translate a fourth link 313 in a direction transverse (such as perpendicular) to the rotational axis of the fourth rotary actuator 311. The linear actuator 312 may be of any suitable type. For example, it may be a linear motor like those shown in FIG. 9 with an elongated magnet track secured to the output shaft of the fourth rotary actuator 311 and a moving coil unit secured to one end of the fourth link 313. The outer end of the fourth link 313 is pivotably connected to the tool support shaft 315 by a second joint 314 which can translate with respect to the tool support shaft 315 in the lengthwise direction of the latter.

Each of the first and second joints 302, 314 permits the tool support shaft 315 to pivot with respect to the second or fourth link 298, 313 with at least two degrees of freedom to permit pitch and yaw motions of the tool support shaft 315, and one of the joints 302, 314 may permit the tool support shaft 315 to pivot with respect to the corresponding link with three degrees of freedom to permit rolling motion of the tool support shaft 315. For example, one of the joints 302, 314 can be a gimbals joint or its equivalent while the other joint can be a spherical joint, such as a ball joint, or its equivalent. Alternatively, both joints 302 and 314 may have two rotational degrees of freedom, and a roll joint may be incorporated into the tool support shaft 315. The distance between joints 302 and 314 is capable of varying as the joints are moved in space. For example, joint 314 may permit the tool support shaft 315 to move in its lengthwise direction with respect to joint 314, and/or the tool support shaft 315 may have a telescoping structure.

Figure 15:
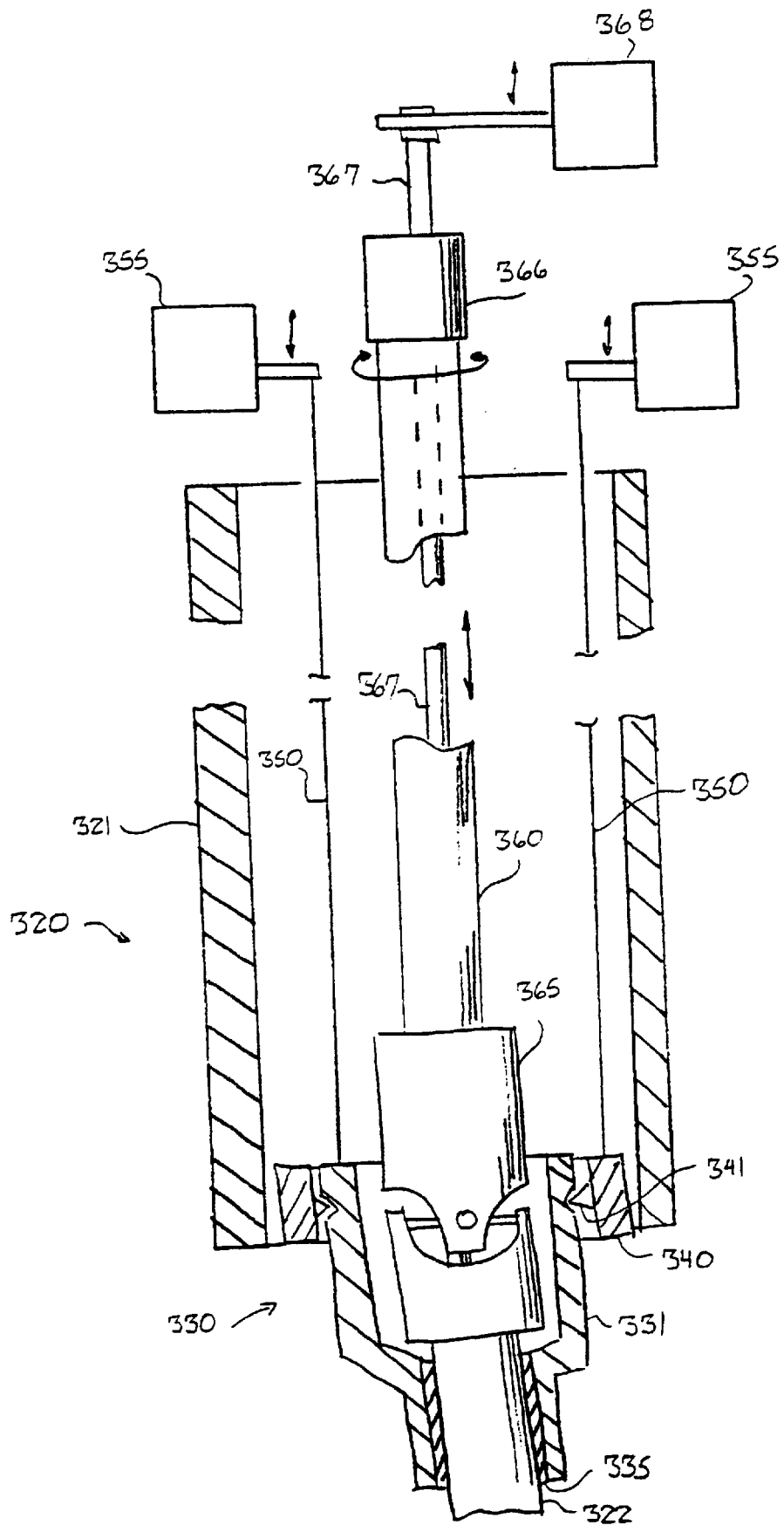
FIG. 15 is a schematic cross-sectional elevation of a tool support shaft for use in a manipulator according to the present invention.
Figure 16:
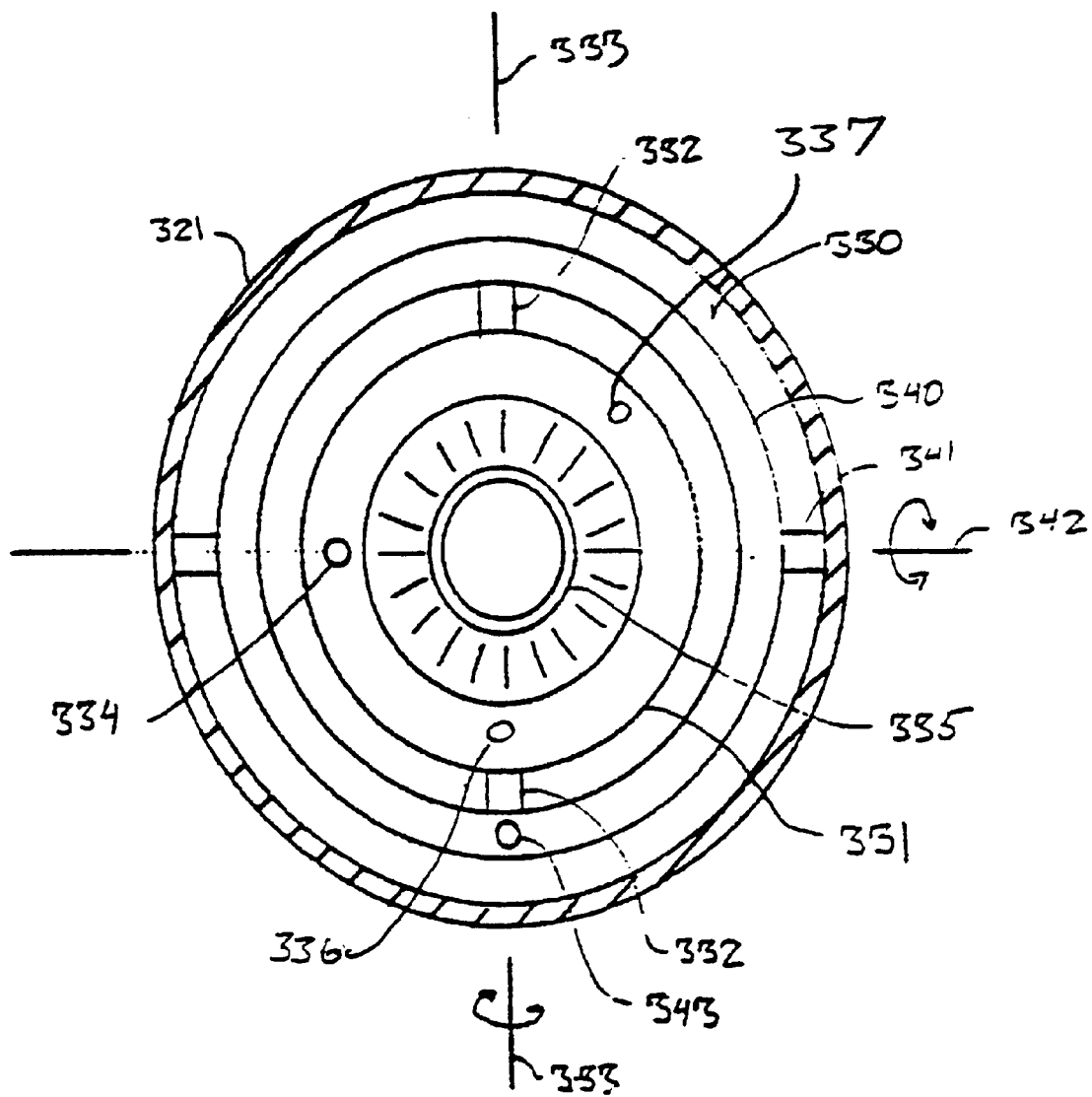
FIG. 16 is a transverse cross-sectional view of the tool support shaft of FIG. 15 looking down on the wrist mechanism with the tool and the tool roll shaft removed.

In a manipulator according to the present invention, the tool may be mounted on the tool support shaft in a fixed position with respect to the tool support shaft so that the tool is manipulated by moving the tool support shaft as a whole. Alternatively, the tool may be connected to the tool support shaft in a manner such that its orientation with respect to the tool support shaft can be adjusted by remote control with one or more degrees of freedom. For example, the tool support shaft may include a wrist mechanism which supports the tool and enables the tool to pivot with respect to the tool support shaft to perform one or more of pitch, yaw, and roll motions. A wide variety of wrist mechanisms exist in the art, and any type capable of permitting the desired motions of the tool can be employed. FIG. 15 is a schematic cross-sectional elevation of an embodiment of a tool support shaft 320 which employs a simple, light-weight wrist mechanism 330 having a gimbals-like structure, and FIG. 16 is a top view of the wrist mechanism as installed in the tool support shaft. As shown in these figures, the tool support shaft 320 comprises a hollow elongated tube 321 of any desired transverse cross-sectional shape, such as circular. At its lower end, the tube 321 supports a wrist mechanism 330 which includes a support tube 331 for supporting a tool 322 and a ring 340 which surrounds the support tube 331. The support tube 331 is pivotably supported by the ring 340 for pivoting about a first axis 333, and the ring 340 is pivotably supported by the tube 321 of the tool support shaft 320 for pivoting with respect to the tube 321 about a second axis 342 transverse to the first axis 333. For simplicity of kinematics and to reduce moments, the first and second axes 333, 342 are preferably perpendicular to each other and intersecting, although they need not be either perpendicular or intersecting.

The support tube 331 can be pivoted about the first axis 333 and the ring 340 can be pivoted about the second axis 342 by a plurality of elongated connectors 350 connected between the wrist mechanism 330 and corresponding actuators 355 disposed at the upper end of the tool support shaft 320. The connectors may be designed to act in tension, in compression, or both. Thus, depending upon the types of forces they need to translate, the connectors 350 can be, for example, rods, bars, wires, chains, belts, springs, or similar members. In the present embodiment, each connector 350 is capable of acting in both tension and compression, so only two connectors 350 and two actuators 355 are required to pivot the tool 322 about the first and second axes. If each connector 350 can act in only a single direction, such as only in tension, a larger number of connectors and actuators may be required to pivot the tool 322 about the two axes, e.g., two connectors and two actuators for each of the support tube 331 and the ring 340 for a total of four connectors and four actuators. Alternatively, if the support tube 331 and the ring 340 are equipped with return springs which bias these members in a certain rotational direction, it is possible to use two connectors acting in tension rather than four. As another alternative, the support tube 331 and the ring 340 can be pivoted about the first and second axes 333 and 342 by three connectors attached to the support tube 331 and acting in tension.

Figure 17:
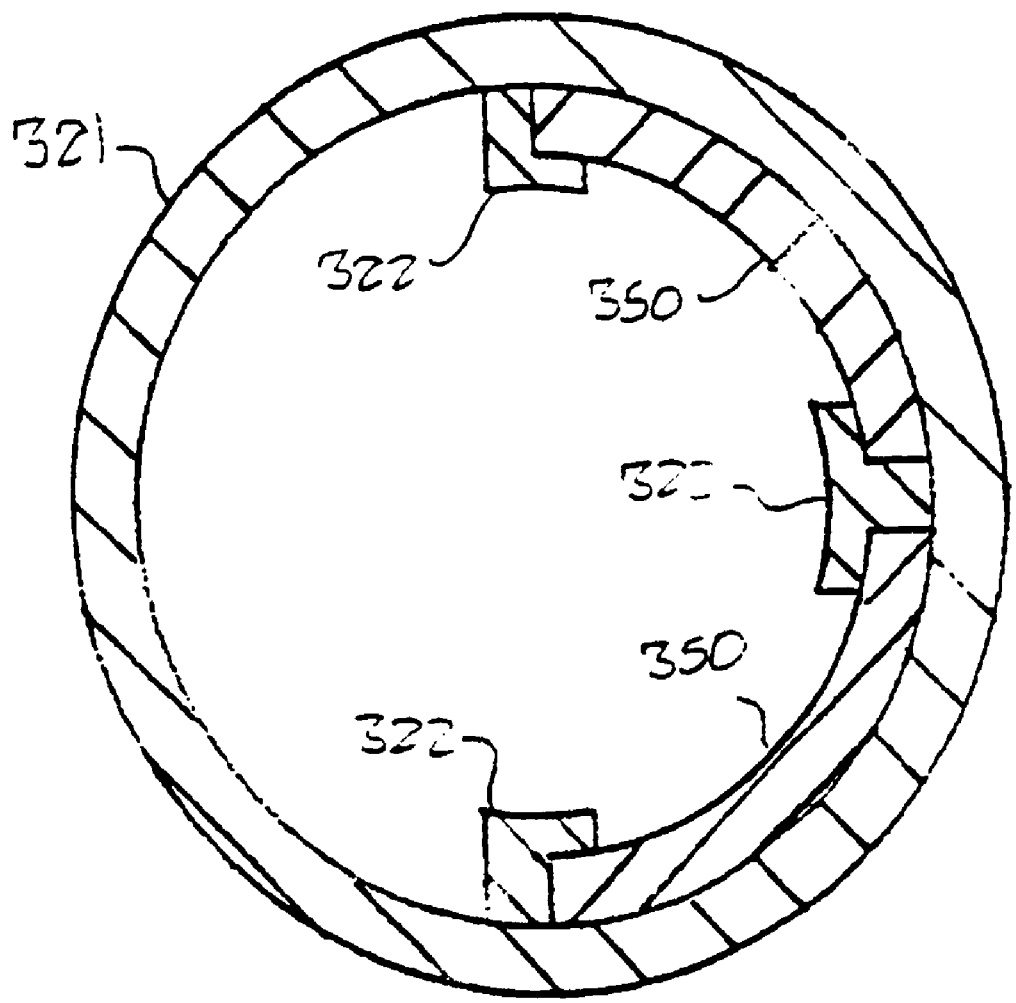
FIG. 17 is a schematic transverse cross-sectional view of the tool support shaft showing connectors located for a wrist mechanism.

In the present embodiment, one of the connectors 350 is connected at its lower end to the support tube 331 at a location 334 spaced from the first axis 333, and the other connector 350 is connected to the ring 340 at a location 343 spaced from the second axis 342. As shown in FIG. 16, in the present embodiment, one connector 350 is connected to the support tube 331 so as to apply force in a location 334 approximately aligned with the second axis 342, and the other connector 350 is connected to the ring 340 so as to apply force at a location 343 approximately aligned with the first axis 333. However, the locations 334 and 343 where the connectors 350 are connected to the tube 331 and the ring 340 need not be aligned with the axes 342 and 333. Each of the connectors 350 is preferably connected to the support tube 331 or the ring 340 by a pivotal connection, since the angle between a connector 350 and the support tube 331 or the ring will vary as the support tube 331 or ring 340 pivots about the first or second axis. The connectors 350 may have any cross-sectional shape which can prevent them from buckling when subjected to axis compression. FIG. 17 is a transverse cross-sectional view of the tool support shaft 320 showing one example of a transverse cross-sectional shape of the connectors 350. In this example, each connector 350 has an arcuate transverse cross-section over at least a portion of its length to give it greater resistance to buckling. Along at least a portion of its length, the widthwise edges of the connectors 350 are received between guides 322 which permit the connectors 350 to slide in the lengthwise direction of the tool support shaft 320 while restraining lateral movement and further increasing the buckling strength of the connectors. At their upper and lower ends, the cross sections of the connectors 350 may differ from an arcuate shape to a shape more convenient for attaching the connectors 350 to the wrist mechanism 330 or the actuators 355.

Instead of one of the connectors 350 being connected to the support tube 331 and another of the connectors 350 being connected to the ring 340, both connectors 350 may be connected to the support tube 331 at different locations. For example, one connector 350 may be connected to the support tube 331 at location 334 in FIG. 16, and another connector 350 may be connected to the support tube 331 at a location such as location 336 in FIG. 16, which is aligned with first axis 333.

In an arrangement in which the support tube 331 and the ring 340 are pivoted about the first and second axes 333 and 342 by three connectors attached to the support tube 331 and acting in tension, the connectors can be attached to the support tube 331 in a variety of locations. For example, one connector can be attached to the support tube 331 in alignment with the second axis 342 (such as at location 334 in FIG. 16), another connector can be attached to the support tube 331 in alignment with the first axis 333 (such as at location 336 in FIG. 16), and a third connector can be attached to the support tube 331 at a location spaced from the first and second axes 333 and 342 (such as at location 337 in FIG. 16).

The actuators 355 for the connectors 350 may be of any type capable of exerting an axial force on the connectors 350, including linear actuators or rotary actuators equipped with mechanisms for converting rotational into linear motion. As is the case with the linear actuators for the shaft support structure, linear motors are particularly suitable. The actuators 355 may be equipped with position sensors and/or force sensors to measure the output portion and/or output force of the actuators 355.

The illustrated wrist mechanism 330 not only permits the tool 322 to pivot about the first and second axes but also permits the tool 322 to perform a rolling motion about a roll axis which is transverse (such as perpendicular) to the first and second axes. The ability of the tool 322 to be rotated about a roll axis makes it easier for the tool 322 to be moved to the most suitable orientation for a given operation and makes the wrist mechanism 300 singularity free within the workspace of the tool 322. Furthermore, depending upon the type of the tool, rotation may be used to enable the tool to exert a torque on a member or to perform a rotary cutting or grinding motion. The tool 322 may be capable of rotating about a roll axis even if its orientation with respect to the tool support shaft 320 is otherwise fixed. In the present embodiment, the tool 322 can be rotated by a tool roll shaft 360 disposed inside the tool support shaft 320 and extending between a rotary actuator 366 at the upper end of the tool support shaft 320 and the tool 322. The tool 322 is rotatably supported by a bearing, such as a bushing 335, mounted in the support tube 331. The tool roll shaft 360 may be rotated by any suitable type of rotary actuator, such as a brushless DC motor or other type of electric motor coupled to the upper end of the tool roll shaft. If the tool 322 is capable of pivoting with respect to the tool support shaft 360 about one or both of the first and second axes, the tool roll shaft 360 is preferably connected to the tool 322 in a manner such that the tool 322 can be rotated by the tool roll shaft 360 when the roll axis is not aligned with the axis of the tool roll shaft 360. For example, in the present embodiment, the lower end of the tool roll shaft 360 is connected to the tool 322 by a universal joint 365. The tool roll shaft 360 may be rotatably supported by the tool support shaft 320 with unillustrated bearings, for example, at one or more locations along its length, to maintain the tool roll shaft 360 at a desired position with respect to the tube 321 of the tool support shaft 320.

In some cases, the tool 322 may have moving parts which are manipulated during surgical use of the tool. Examples of tools with moving parts include forceps, scissors, needle holders, clamps, and staplers. Depending upon the structure of the tool 322, the moving parts can be operated by a variety of mechanisms, such as a cable, a rod, pneumatic or hydraulic tubing, or electrical wires extending from the tool to an upper portion or exterior of the tool support shaft to enable the tool to be remotely operated, mechanically, pneumatically, hydraulically, or electrically. A cable, wire, or other member for operating the tool may extend through a bore in the tool roll shaft 360, or it may extend along the exterior of the tool roll shaft 360.

In the present embodiment, the tool 322 has moving parts which can be actuated by a connector 367 extending through the tool roll shaft 360 and the universal joint 365 between the moving parts and an actuator 368 disposed at the upper end of the tool support shaft 320. The connector 367 may be one which acts in tension and/or compression, depending upon the structure of the tool 322. For example, the tool 322 may be operated by the connector 367 acting in tension against a return spring in the tool 322 which returns the tool to an initial state when the tensile force is released. The connector 367 may rotate the tool roll shaft 360 or it may be supported so as to remain stationary as the tool roll shaft 360 rotates. The connector 367 is preferably capable of operating the tool 322 even when the longitudinal axis of the tool 322 is not aligned with the longitudinal axis of the tool roll shaft 360. For example, the connector 367 can be a flexible member, such as a cable, which can bend when the two axes are not aligned, or it may comprise rigid sections connected together by pivotable joints which enable the connector 367 to exert a force through an angle. Like the actuators 355 for pivoting the support tube 331 and ring 340 of the wrist mechanism 330, the actuator 368 for the connector 367 may be of any suitable type, such as a linear actuator or a rotary actuator coupled to the connector 367 by a mechanism which converts rotary to linear motion.

Figure 18:
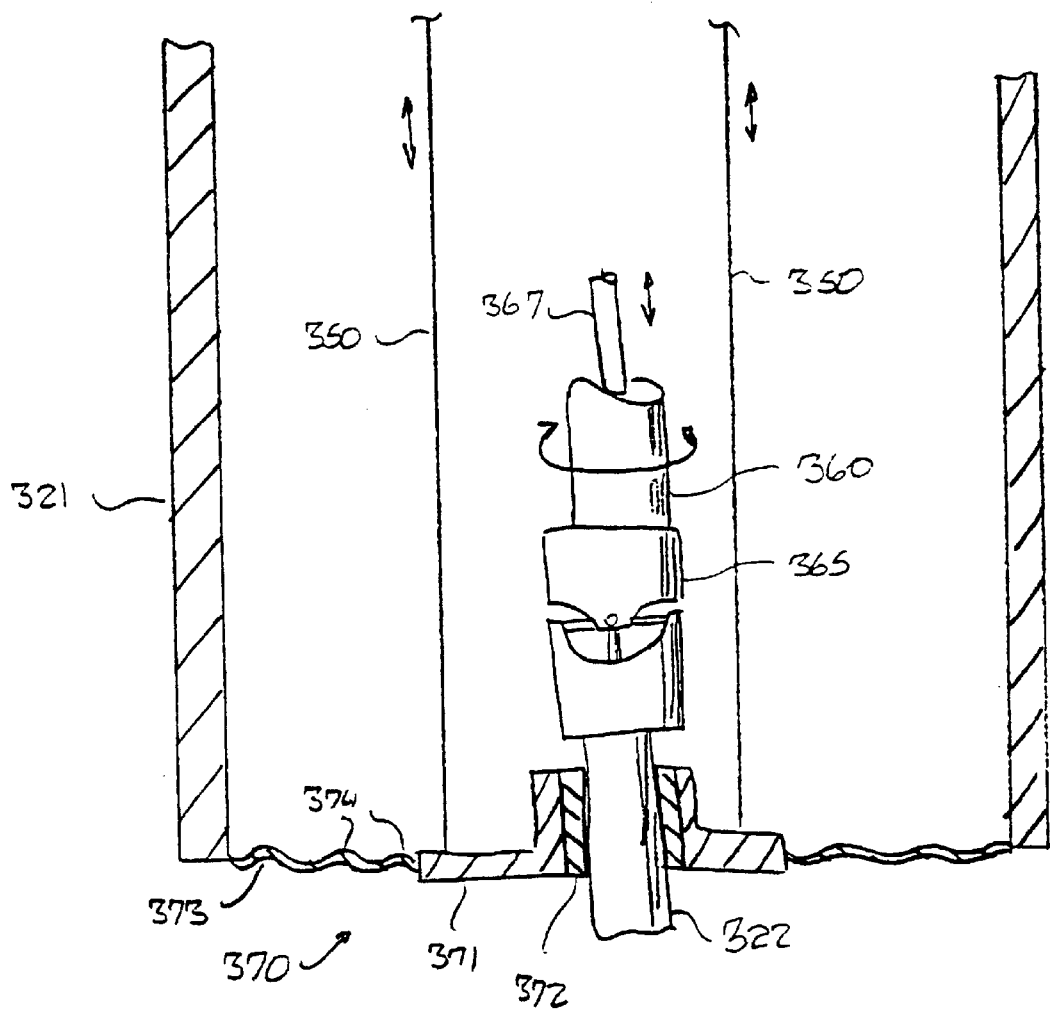
FIG. 18 is a schematic vertical cross-sectional view of another example of a wrist mechanism for use in the present invention.

FIG. 18 is a schematic cross-sectional elevation of another example of a wrist mechanism 370 which can be used in the present invention. This wrist mechanism 370 includes a support tube 371 which rotatably supports a tool 322 through a bushing 372 and an annular diaphragm 373 of plastic, paper, metal, or other suitable material which surrounds the support tube 371. The inner periphery of the diaphragm 373 is secured and preferably sealed in a fluid-tight manner to the support tube 371 around its entire circumference, and the outer periphery of the diaphragm 373 is sealed in a fluid-tight manner to the tube 321 of the tool support shaft 320 around its entire circumference. The diaphragm 373 is sufficiently strong that it can support the weight of the support tube 371 but sufficiently flexible that it can permit the support tube 371 to pivot about first and second axes so that the support tube 371 can pitch and yaw. The illustrated diaphragm 373 is formed with annular corrugations 374 which give it flexibility. The radially outer region of the diaphragm 373 is preferably more flexible than the central region surrounding the support tube 371. Two connectors 350 like those employed in the previous embodiment are connected to the support tube 371 at locations spaced from each other in a circumferential direction by a suitable angle (such as 90°). The upper end of each connector 350 is connected to a corresponding unillustrated actuator which can translate the connector 350 in its lengthwise direction. When one connector 350 is translated in its lengthwise direction, the support tube 371 and the tool 322 are pivoted about the first axis, and when the other connector 350 is translated in its lengthwise direction, the support tube 371 and the tool 322 are pivoted about the second axis. If the diaphragm 373 is sealed to both the support tube 371 and the tube 321 of the tool support shaft 320, the diaphragm 373 can prevent the transfer of contaminants between the interior of the tool support shaft 320 and the interior of a patient's body in either direction. Except for the wrist mechanism 370, the structure of the tool support shaft 320 may be the same as described with respect to FIG. 15.

Figure 19:
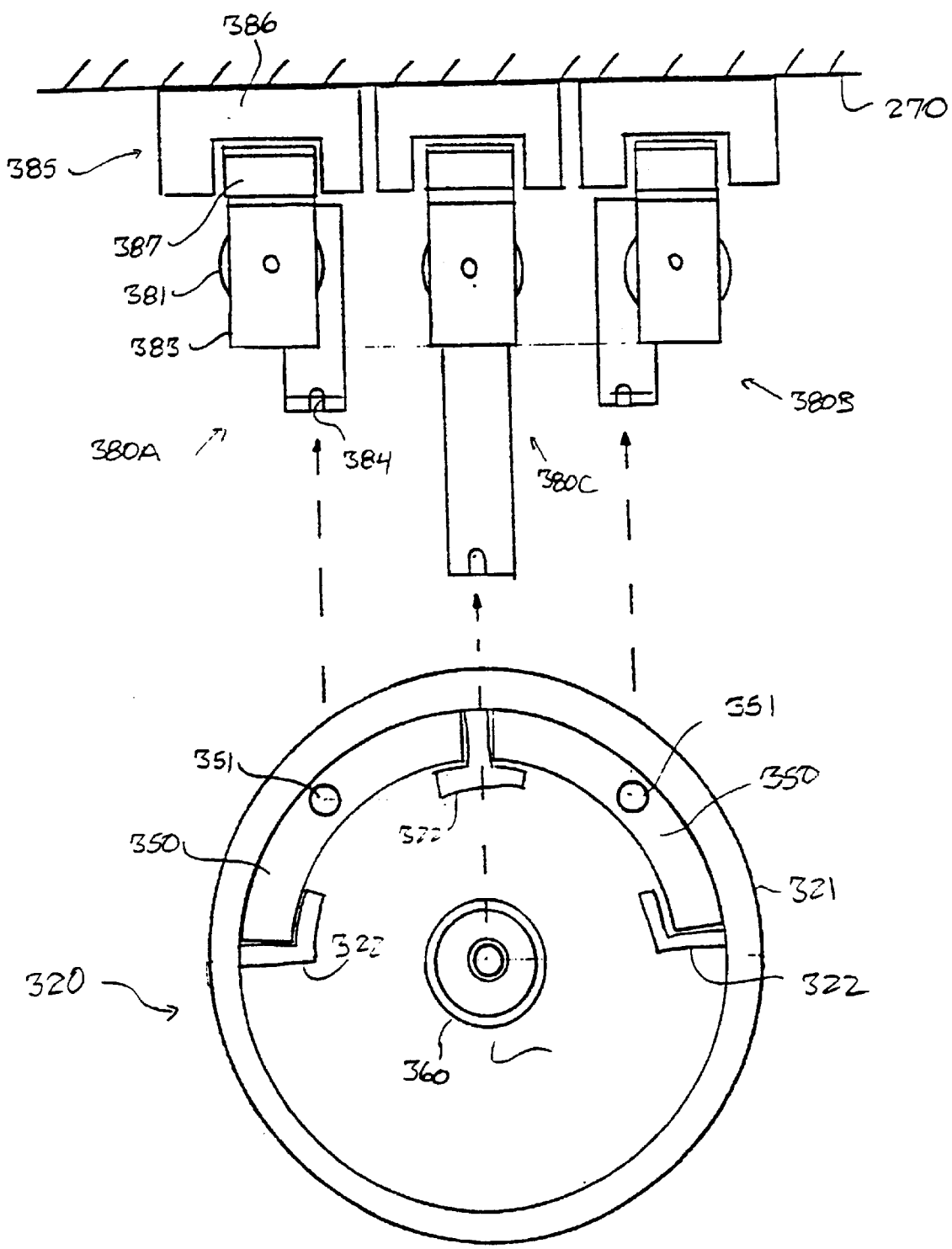
FIG. 19 is a schematic top view of three actuators for use with a detachable tool support shaft.
Figure 20:
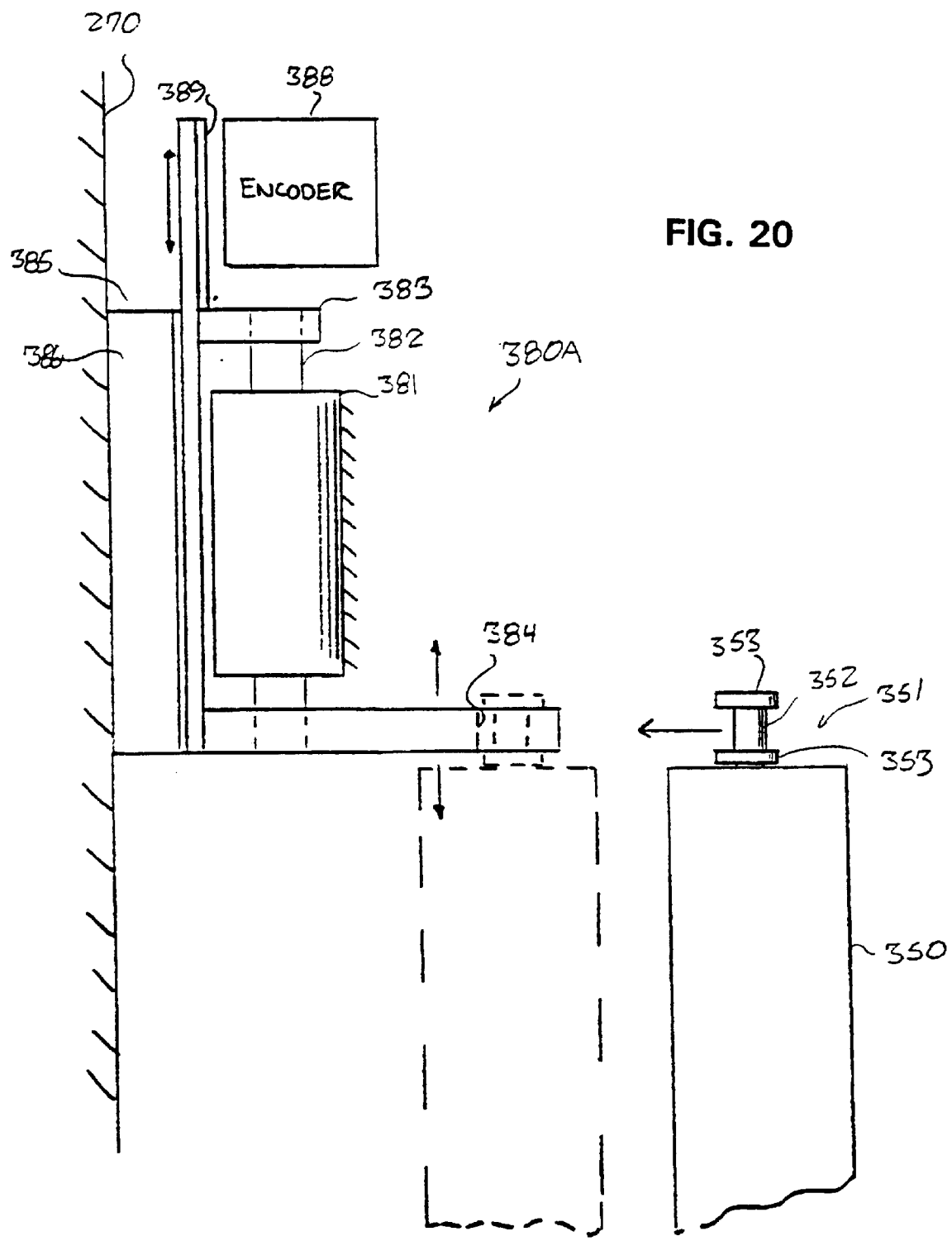
FIG. 20 is a schematic side elevation of one of the actuators of FIG. 19.
Figure 21:
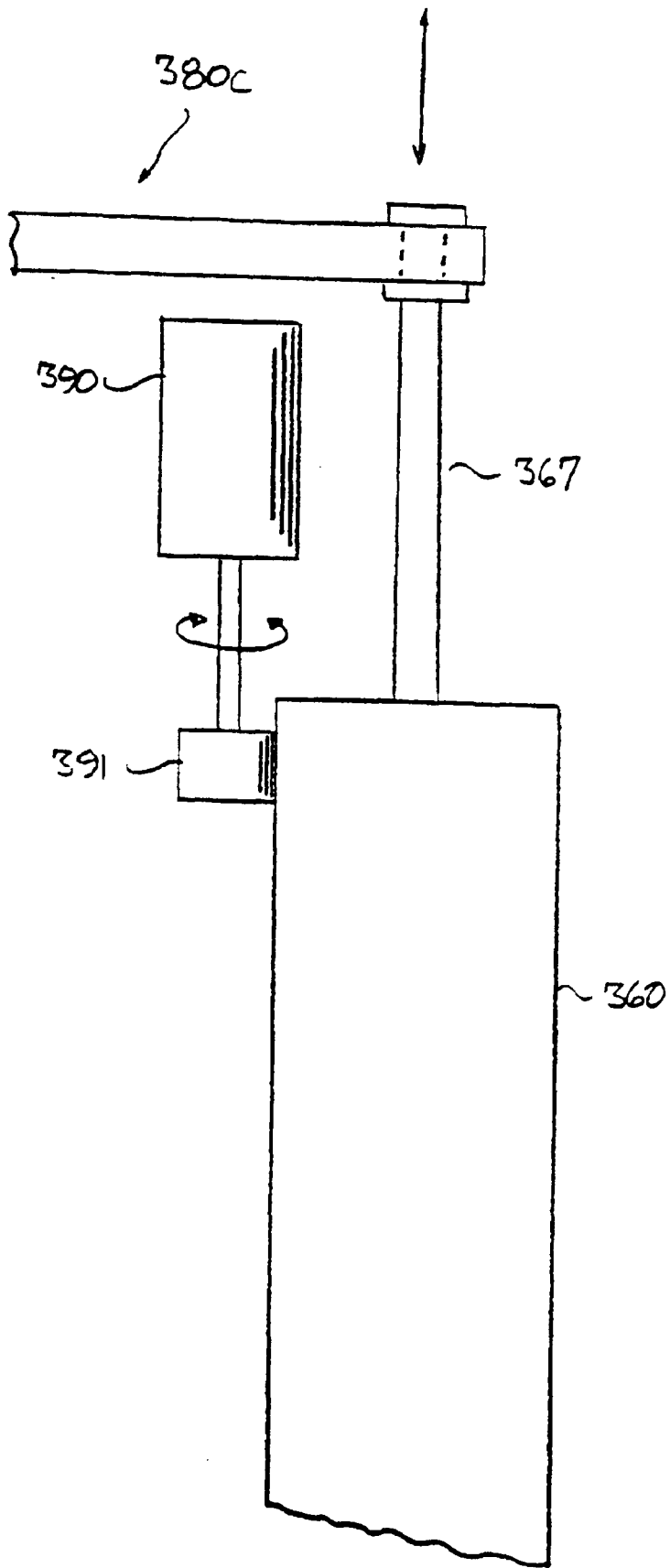
FIG. 21 is a schematic side elevation of an actuator for a tool roll shaft.

At least the lower portion of the tool support shaft in the proximity of the tool will generally need to be sterilized prior to each surgical use of the tool support shaft. In order to make it easier to sterilize the tool support shaft, the entire tool support shaft may be detachable from other portions of the manipulator. FIGS. 19–21 illustrate an arrangement which can detachably support a tool support shaft 320 while operating its moving parts. In this arrangement, the tool support shaft 320 can be detachably secured to a support frame 270 of a shaft support structure, which may have the structure of any of the shaft support structures described above. A plurality of actuators 380A–380C and 390 are mounted on the support frame 270. A first and a second linear actuator 380A and 380B produce linear movement of two connectors 350 which are connected to an unillustrated wrist mechanism like those shown in FIGS. 15 or 18, for example. A third linear actuator 380C produces linear movement of a connector 367 for operating moving parts of an unillustrated tool supported by the wrist mechanism, and a rotary actuator 390 rotates a tool roll shaft 360 connected to the tool. Each of the linear actuators 380A–380C can detachably engage the corresponding connector, while the rotary actuator 390 can detachably engage the tool roll shaft 360. FIG. 20 is a side elevation of the first linear actuator

380A. The other linear actuators 380B and 380C may have a similar structure. Linear actuator 380A comprises a DC linear servo motor having a cylindrical housing 381 and an output shaft 382 movable in either axial direction of the housing 381. While the motor need not be cylindrical, a cylindrical shape is often advantageous from the standpoint of space considerations. Cylindrical linear servo motors of this type are available from a variety of manufacturers, such as Northern Magnetics of Santa Clarita, Calif. The motor may be either a moving magnet or a moving coil type, although a moving magnet type may be advantageous from the standpoint of ease of dissipating heat generated by the coil, since the coil of a moving magnet motor is located exterior of the magnet and can be mounted on a heat sink. To enable the moving portion of the motor to translate more smoothly, the moving portion may be mounted on a sliding portion 387 of a linear bearing 385, with the stationary portion 386 of the bearing 385 being supported by the support frame 270. The output shaft 382 is secured at each end to a frame 383 which is generally U-shaped in profile. The frame has two parallel legs which extend away from the support frame 270. The lower leg has a recess 384 formed in its outer end. The upper end of each connector 350 is shaped so as to be detachably received within the recess 384. For example, in this embodiment, the upper end of each connector 350 has a spool-shaped portion 351 having a mid-portion 352 small enough to fit into the recess 384 on the frame 383 and upper and lower flanges 353 larger in diameter than the recess 384. When the spool-shaped portion 351 is inserted into the recess 384, translation of the frame 383 in the lengthwise direction of the output shaft 382 will bring the flanges 353 into abutment with the frame 383, thereby translating the connector 350 in its lengthwise direction.

The rotary actuator 390 has an output shaft on which a roller 391 is mounted. When the frames 383 of the linear actuators 380A–380C engage the upper ends of the corresponding to connectors 350 and 367 for the wrist mechanism and for operating the tool, the roller 391 is pressed into frictional engagement with the outer surface of the tool roll shaft 360 such that rotation of the roller 391 will cause the tool roll shaft 360 to rotate about its axis. The materials forming the roller 391 and/or the outer surface of the tool roll shaft 360 may be selected for good rolling contact. For example, the roller 391 may be made of a high friction deformable rubber. It is also possible for the roller 391 to be replaced by a pinion and for the tool roll shaft 360 to have gear teeth on its exterior for engagement with the pinion.

After each use, a direct tool support shaft 320 can be detached from the shaft support structure and replaced with a clean one, and the dirty tool support shaft 320 can be either sterilized or discarded. The tool support shaft 320 itself does not require any expensive components, so it can be manufactured sufficiently economically to be disposable after a single use.

The arms of a manipulator according to the present invention are physically capable of moving independently of each other, i.e., they are not linked together in a manner such that movement of one arm forces the other arm to move in a certain manner. Therefore, in order to adjust the orientation of the tool support shaft when the lower end thereof is inserted into the body of a patient while keeping the tool support shaft aligned with a virtual pivot point, it may be necessary to coordinate the operation of two or more of the actuators. For some movements of the tool support shaft, it may be possible for a human operator to manually coordinate the operation of different actuators. However, it is usually easier to employ an automatic control mechanism, such as an electronic controller, which can automatically coordinate the operation of a plurality of actuators based on commands from a human operator indicating the desired movements of the tool support shaft.

Figure 22:
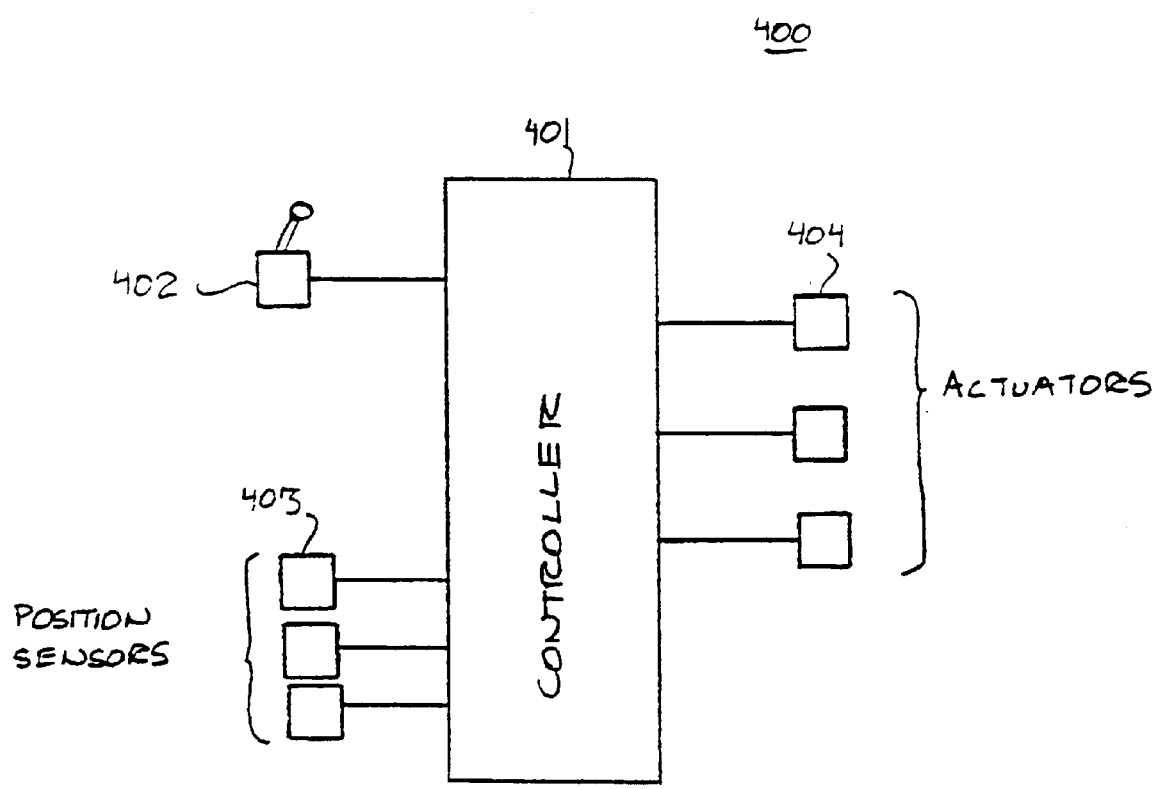
FIG. 22 is a block diagram of a control system for use with a manipulator according to the present invention.

FIG. 22 is a block diagram of an example of a control system 400 which can be employed with a manipulator according to the present invention. The control system 400 includes an electronic controller 401, such as a general purpose or special purpose microcomputer. The controller 401 receives input signals from position sensors 403 and/or force sensors for the various linear and/or rotary actuators 404 of the manipulator. The controller 401 also receives input signals from one or more suitable input devices 402 by means of which the operator can provide the controller 401 with commands indicating the desired movement of and/or force to be applied by the tool support shaft. A wide variety of input devices 402 can be employed, such as a joystick, a haptic interface (an input device which can provide force feedback to the operator), a keyboard, a tape memory or other storage device, a foot pedal, a mouse, a digitizer, a computer glove, or a voice operated controller. One example of a haptic interface which can be employed is a parallel manipulator of the type described in U.S. patent application Ser. No. 60/056,237 entitled "Parallel Mechanism". There may be separate input devices for controlling different types of motions of the manipulator, or for controlling the tool support shaft at different times. For example, one input device may be used when it is desired to pivot the tool support shaft about a virtual pivot point, while another input device may be used when it is desired to translate the tool support shaft in its lengthwise direction without pivoting it. Still another input device may be used for manipulating the tool support shaft when no part of it is inserted into a patient's body. Based on input signals from the input devices and the signals from the position sensors, the controller 401 generates control signals for the actuators 404 so as to drive the tool support shaft in a desired manner.

The input device(s) 402 for controlling the movements of and/or the forces applied by the tool support shaft can also be used to control the actuators 404 for the tool, or one or more separate input devices 402 can be provided for this purpose.

The controller 401 can control the tool support shaft and the tool in a variety of manners, depending upon the requirements of the task which is to be performed by the manipulator. For example, the controller 401 may perform position control, force control, or a combination of position and force control (hybrid position/force control). Examples of these and other suitable control methods capable of use in the present invention and algorithms for their implementation are well known in the field of robotics and described in detail in published literature. Force control or hybrid position/force control methods are highly suitable for the present invention because they can maintain the forces exerted by the tool support shaft and the tool on a patient at suitable levels and enable the manipulator to be safely used for even delicate surgical procedures, including microsurgical operations.

The tool support shaft and the tool may be controlled by the controller 401 so as to move in the same direction that the user moves his hand in operating the input device 402, e.g., so that if the user rotates a joystick or other input device 402 clockwise, the tool support shaft or tool will also rotate clockwise. However, some conventional minimally invasive surgical devices require the user to move his hand in the opposite direction from which a tool is to be moved. For a user accustomed to operating such devices, the controller 401 may be made to control the tool support shaft and the tool so as to move in the opposite direction from the direction that the user moves his hand in operating the input device 402. The controller 401 may be equipped with a switch which enables a user to select either reverse or non-reversed motions of the tool support shaft and the tool with respect to motions of the hand of the user.

The gain of the control system 400 can be adjusted to enhance the dexterity of the user of the manipulator. For example, the gain can be set such that movement of the hand of the user in operating a joystick or other input device results in much smaller movements (either translational or rotational) of the tool support shaft or the tool. Thus, movements by the hand of the user on the order of millimeters could be reduced to motions of the tool support shaft or the tool on the order of micrometers, enabling the user to make controlled movements of the tool much smaller than he could make by hand. The ability of the manipulator to scale down the magnitude of motions of the hand is useful not only in surgery but in other tasks requiring dexterity, such as in assembly of very small parts. On the other hand, when the tool support shaft or the tool needs to make large movements, the gain can be set such that movement of the hand of the user on the input device results in larger translational and/or rotational movements of the tool support shaft or the tool. Scaling up the motions of the hand of the user in this manner permits the user to maintain his hand relatively stationary in the most comfortable position, which again enhances the user's dexterity. When the control system 400 provides force feedback to the input device 402, the gain of the control system 400 may also be adjusted to enhance the operator's sense of touch. For example, the resistance to movement of the input device 402 felt by the hand of the operator may be controlled to be greater than the resistance to movement encountered by the tool so that the operator can clearly sense even low levels of resistance encountered by the tool. Scaling up the resistance felt by the user is helpful when the tool is contacting soft tissue. On the other hand, when the tool is contacting bone or other hard materials, it may be desirable to scale down the resistance felt by the user.

Most individuals experience some level of tremor in their hand motions when performing manual operations. If the control system 400 has a manually operated input device, the control system 400 may be equipped with a filter which filters out components of a signal from the input device 402 having the frequency of the tremor so that the tremor is not reproduced in the motions of the tool support shaft or the tool.

Figure 27:
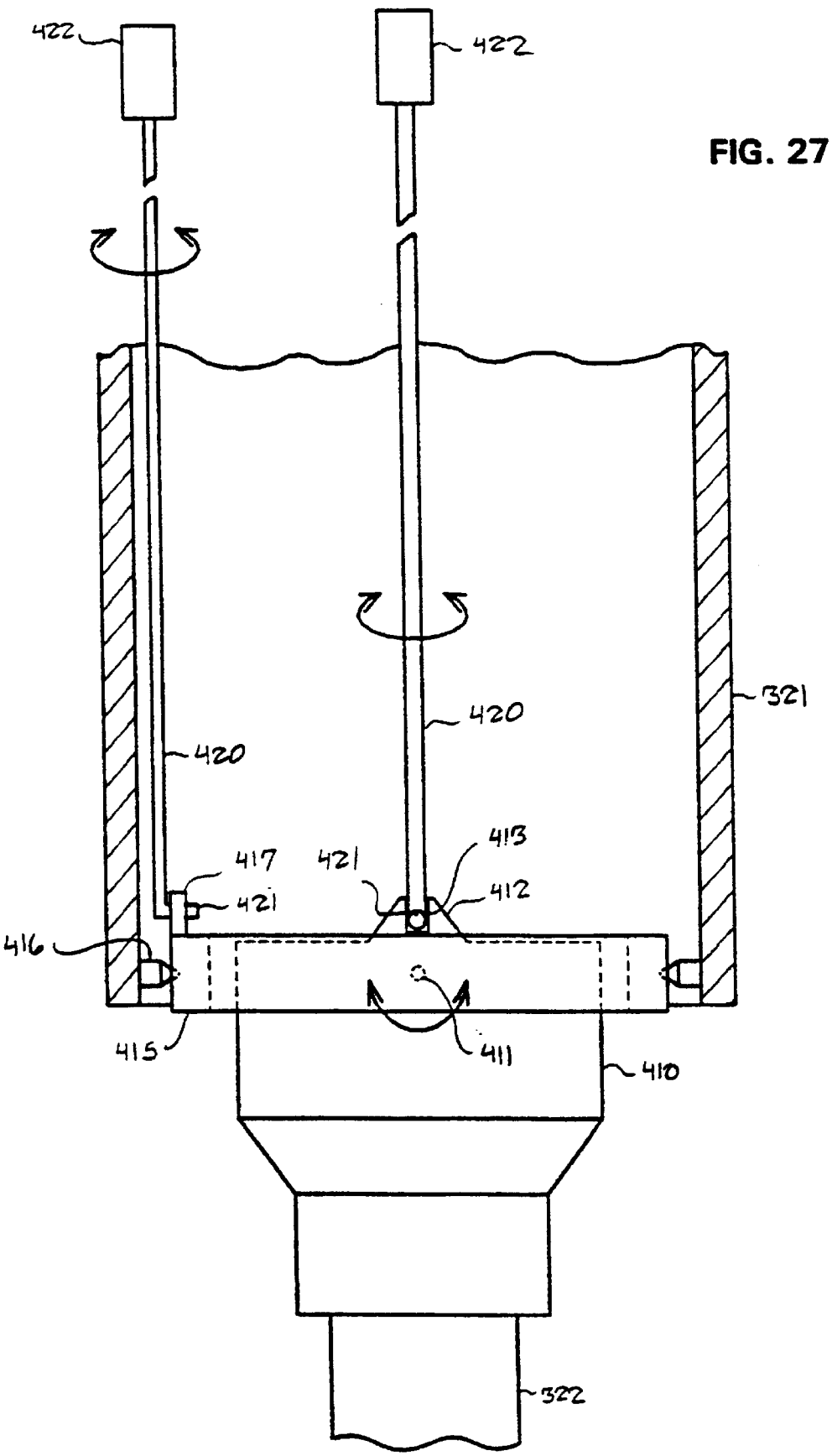
FIGS. 27 and 28 are elevations of another example of a wrist mechanism according to the present invention.
Figure 28:
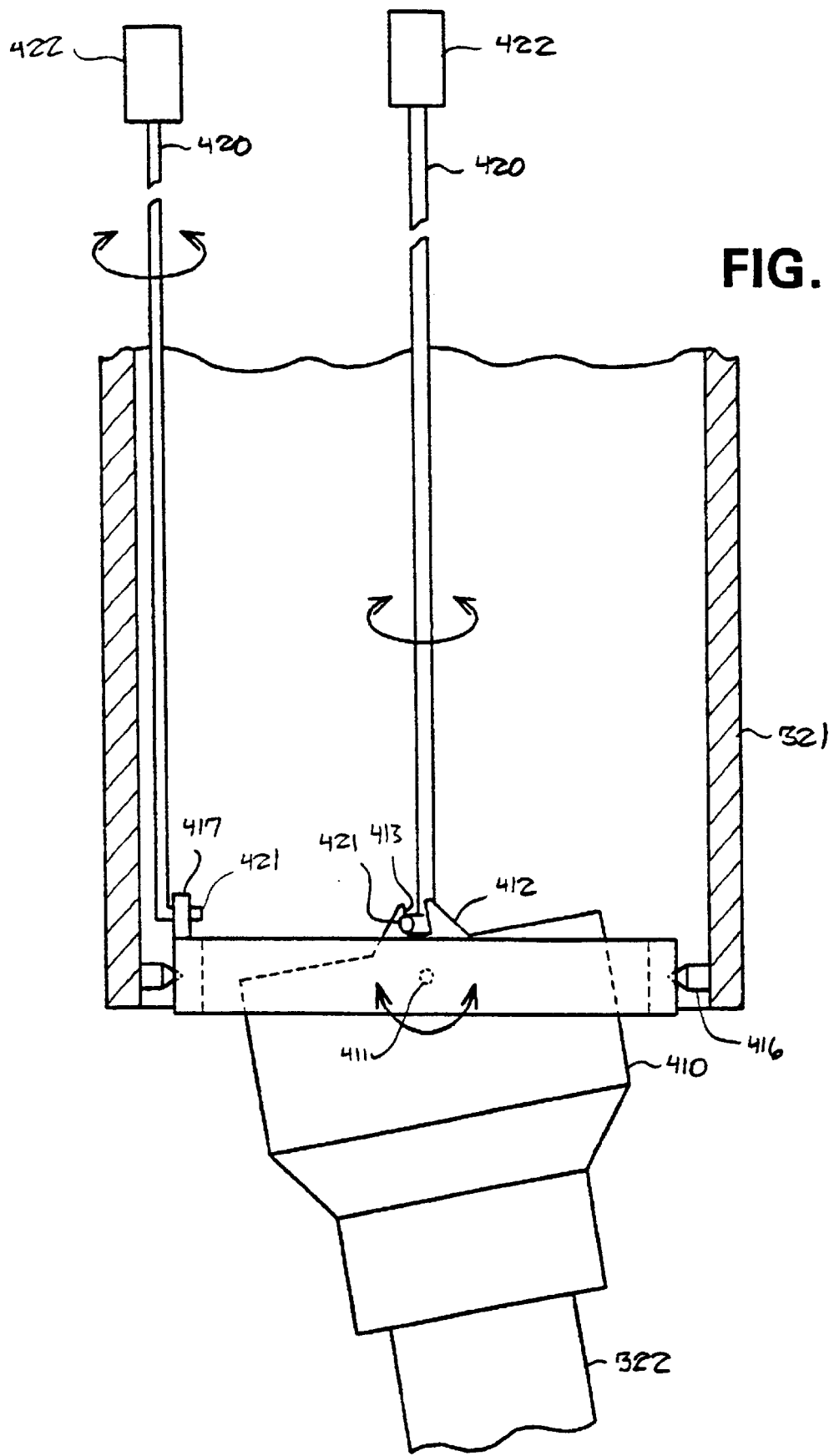

FIGS. 27–34 illustrate other examples of gimbals-type wrist mechanisms for use in the present invention. FIGS. 27 and 28 are front elevations of a wrist mechanism which is operated by connectors acting in torsion rather than in tension or compression. Like the wrist mechanism of FIG. 15, the wrist mechanism of FIGS. 27 and 28 includes a support tube 410 for rotatably supporting a tool 322 and a ring 415 surrounding the support tube 410. The support tube 410 need not have any particular structure. For example, it may be generally similar in structure to the support tube 331 shown in FIG. 15. The tool 322 may be connected to a mechanism for rotating the tool 322 about its axis or operating moving components of the tool 322 in a manner such as that shown in FIG. 15. However, to simplify the drawings, such a mechanism has been omitted from FIGS. 27–34. As in the embodiment of FIG. 15, the support tube 410 is rotatably supported in any suitable manner by the ring 415 for pivoting about a first axis, and the ring 415 is rotatably supported in any suitable manner by a tube 321 or other convenient support member for pivoting about a second axis perpendicular to the first axis. For example, the support tube 410 may be pivotably supported by two bearings 411 (only one of which is shown) secured to the ring 415 in alignment with the first axis, and the ring 415 may be pivotably supported by two bearings 416 secured to the tube 321 in alignment with the second axis. FIG. 27 shows the wrist mechanism in an initial position in which the tool 322 is aligned with the axis of the tube 321, and FIG. 28 shows the wrist mechanism in a position in which the support tube 410 is pivoted about the first axis from its initial position. The support tube 410 and the ring 415 can each be pivoted about the first or second axis, respectively, by a rotatable connector 420 which can be rotated by any suitable actuator, such as a motor 422, connected to its upper end. Each connector 420 has a leg 421 at its lower end extending transversely to the axis of the connector 420. Each leg 421 is connected to the support tube 410 or the ring 415 in a manner such that when the connector 420 is rotated about its axis, movement of the leg 421 about the axis of the connector 420 causes the support tube 410 or the ring 415 to pivot about the first or second axis. For example, in the present embodiment, a projection 412 extends upwards from the support tube 410 in alignment with the first axis, another projection 417 extends upwards from the ring 415 in alignment with the second axis, and the leg 421 of each connector 420 loosely engages a slot or other opening formed in the corresponding projection, such as slot 413 formed in projection 412. When the connector 420 is rotated about its axis, the leg 421 of the connector 420 pushes against one of the sides of the slot to cause the support tube 410 or the ring 415 to pivot about the first or second axis. The slot may be elongated to enable the projection 412, 417 to remain engaged with the leg 421 of the corresponding connector 420 as the attitude of the support tube 410 or ring 415 varies.

Figure 29:
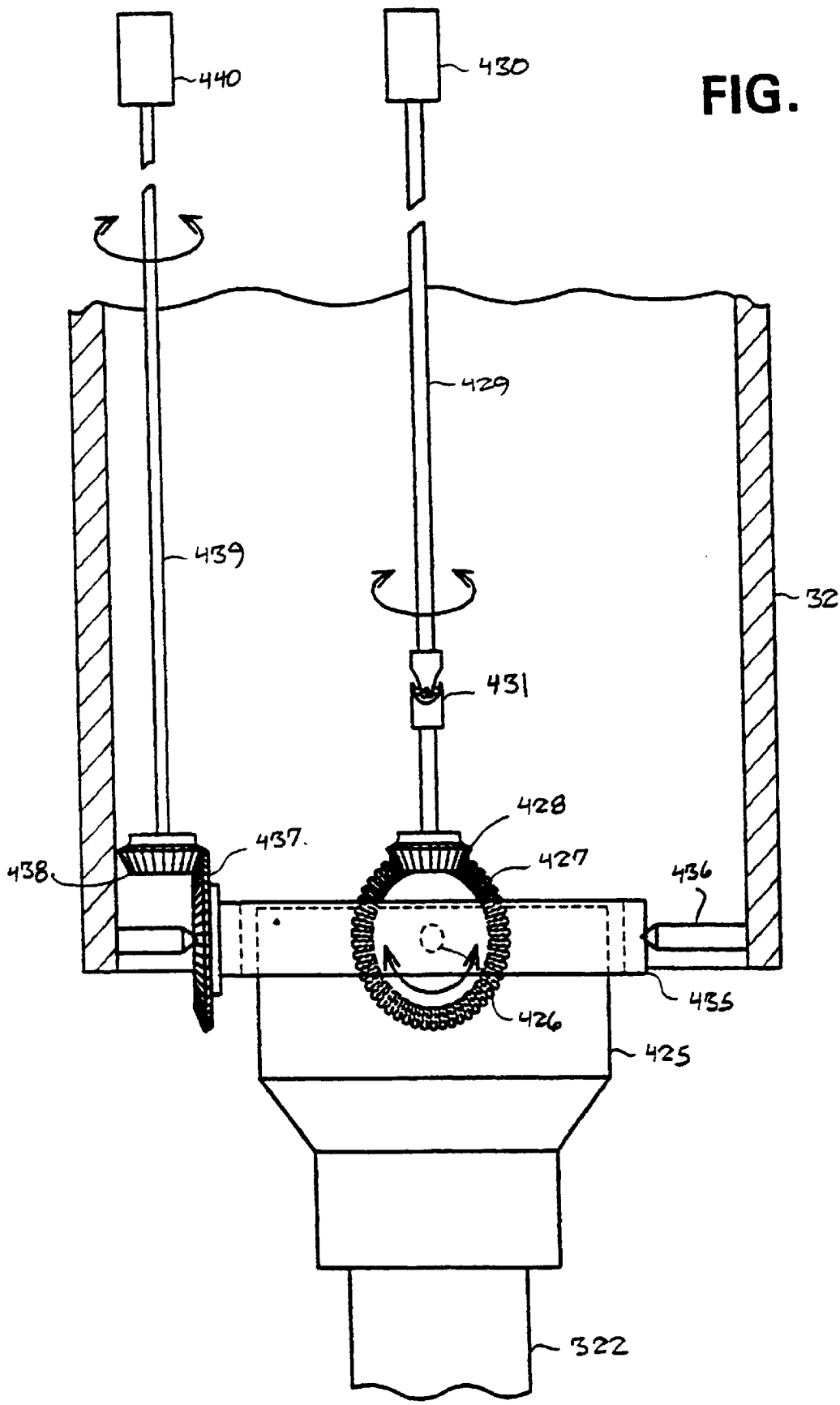
FIGS. 29 and 30 are elevations of two more examples of wrist mechanisms according to the present invention.

FIG. 29 illustrates another example of a gimbals-type wrist mechanism in which a support tube 425 and a ring 435 are made to pivot about respective first and second axes by connectors which act in torsion. The support tube 425 and the ring 435, which may be similar in structure to those of the preceding embodiment, can be pivotably supported in any suitable manner. For example, in FIG. 29, the support tube 425 is pivotably supported by two bearings 426 secured to the ring 435 in alignment with the first axis, and the ring 435 is pivotably supported by two bearings 436 secured to a tube 321 in alignment with the second axis. In this example, the support tube 425 is equipped with a gear 427 secured to it coaxially with the first axis, and the ring 435 is equipped with a gear 437 secured to it coaxially with the second axis. The gear 427 on the support tube 425 meshes with another gear 428 secured to the lower end of a drive shaft 429 which can be rotated about its axis by a motor 430 or other actuator connected to its upper end. Similarly, the gear 437 on the ring 435 meshes with another gear 438 secured to the lower end of a drive shaft 439 which can be rotated about its axis by a motor 440 or other suitable actuator connected to its upper end. The gears 427, 428, 437, 438 can be of any type capable of transmitting torque when the axes of rotation of two meshing gears are not aligned with each other. In FIG. 29, the gears are bevel gears forming two right-angle drives. If any of the gears is expected to rotate by less than 360° about its axis, the gear may be a gear sector (a gear having teeth extending only around a segment of a circle) to decrease its weight. The second axis about which the ring 435 rotates will always maintain a constant angle with respect to the vertical and with respect to the axis of the drive shaft 439 for the ring 435. In contrast, the angle with respect to the vertical of the first axis about which the support tube 425 rotates will vary as the ring 435 is rotated about the second axis. Therefore, the two gears 427, 428 for the support tube 425 may be chosen so as to be capable of transmitting torque to each other when their rotational axes are at a variety of angles to each other. Alternatively, the drive shaft 429 for rotating the support tube 425 may be a flexible shaft, or a universal joint 431 or other joint can be installed in the shaft 429 to enable the lower end of the shaft 429 to be at various angles to the upper end of the shaft 429 and to enable the rotational axes of the two gears 427, 428 for the support tube 425 to maintain a constant angle with respect to each other.

Figure 30:
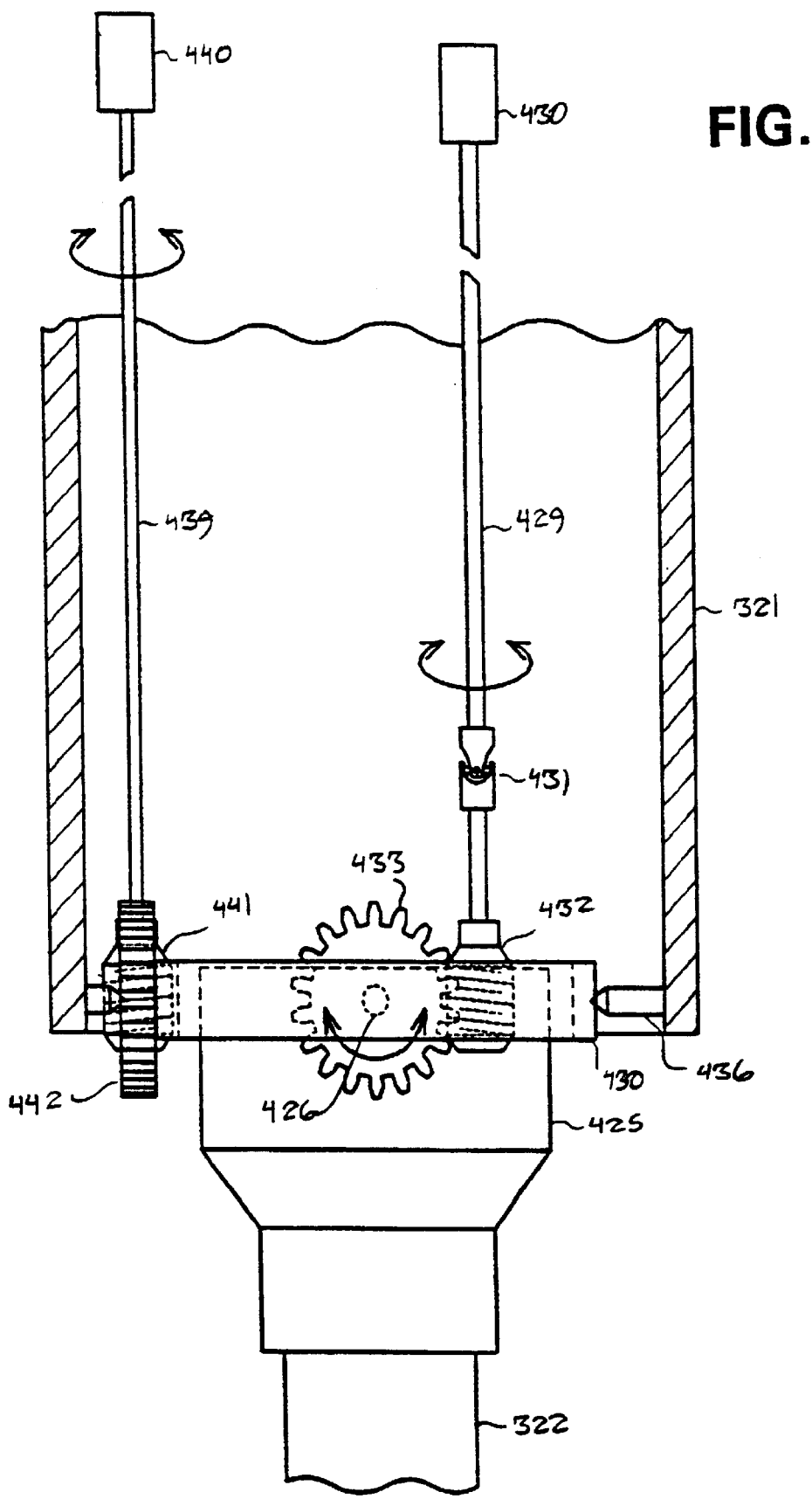

FIG. 30 illustrates a variation of the structure shown in FIG. 29 in which the bevel gear drives of FIG. 29 have been replaced by worm gear drives, each including a worm mounted on the lower end of a rotatable shaft and a worm gear mounted on the support tube 425 or the ring 435 coaxially with the first or second axis, respectively. As shown in FIG. 30, a worm 432 is secured to the lower end of drive shaft 429, and a worm gear 433 which engages with the worm 432 is secured to the support tube 425 in alignment with the first axis.

Similarly, a worm 441 is secured to the lower end of drive shaft 439, and a worm gear 442 which engages with the worm 441 is secured to the ring 435 in alignment with the second axis. Each drive shaft 429, 439 can be rotated about its axis by a motor 430, 440 or other suitable actuator connected to its upper end. As described with respect to FIG. 29, the drive shaft 429 for rotating the support tube 425 may include a universal joint 431 or may be otherwise structured to enable it to transmit torque to worm gear 433 when the axis of worm gear 432 is not vertical due to the ring 435 rotating about the second axis.

Figure 31:
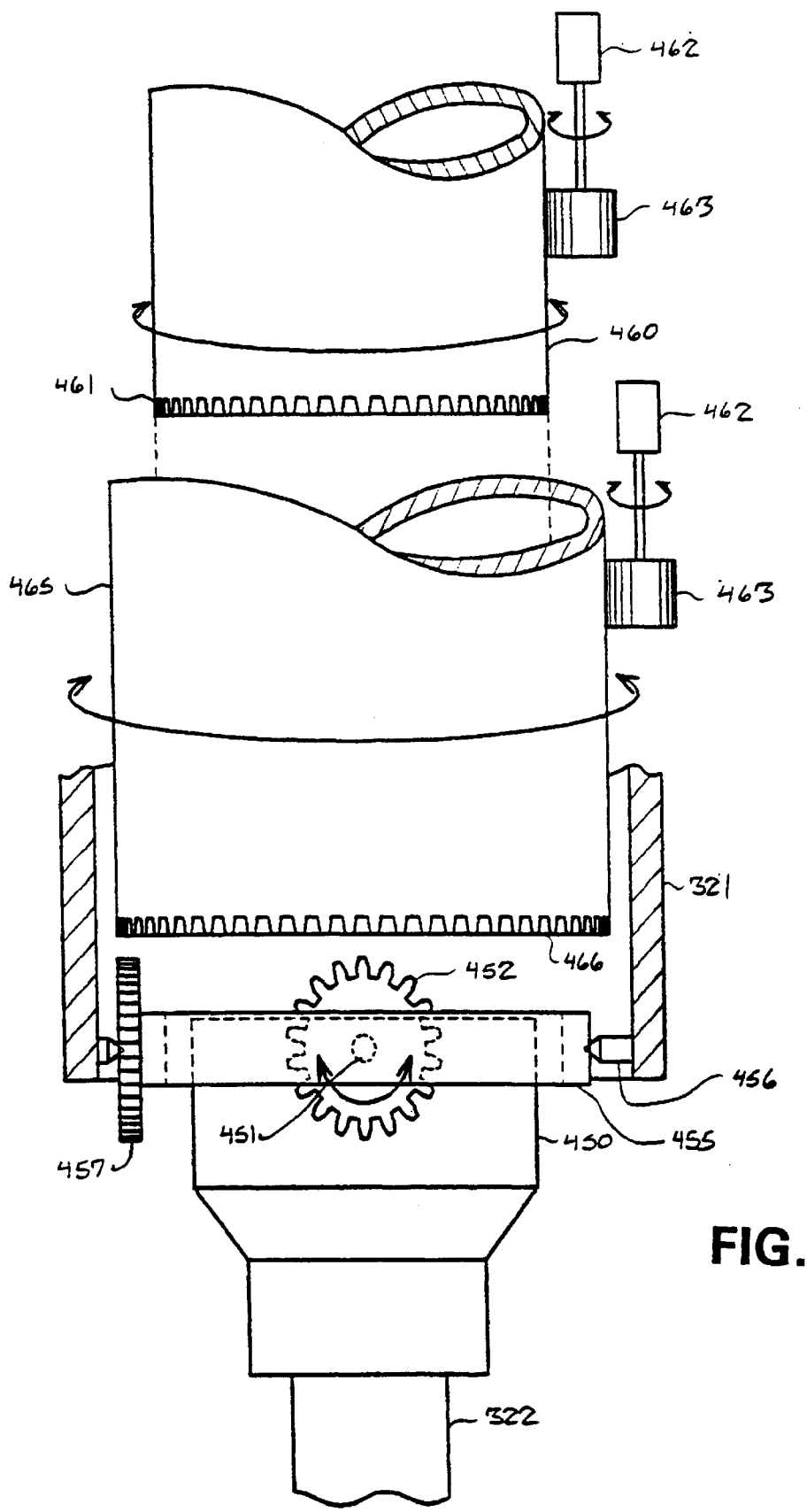
FIG. 31 is an exploded elevation of another example of a wrist mechanism according to the present invention.

FIG. 31 is an exploded elevation of another example of a gimbals-type wrist mechanism for use in the present invention. In this example, a support tube 450 and a ring 455, which may be similar in structure to those of the preceding embodiments, are rotatably supported in any suitable manner for pivoting about a first axis and a second axis, respectively, which is perpendicular to the first axis. For example, the support tube 450 may be pivotably supported by two bearings 451 secured to the ring 455 in alignment with the first axis, and the ring 455 may be pivotably supported by two bearings 456 secured to a tube 321 in alignment with the second axis. The support tube 450 and the ring 455 are equipped with a pinion 452 and 457 mounted on them coaxially with the first axis or the second axis, respectively. The support tube 450 and the ring 455 can be rotated about the first and second axes by first and second coaxial tubes 460 and 465, each engaging with one of the pinions 452 or 457 to rotate the pinion and the support tube 450 or ring 455 about its axis The first tube 460 has gear teeth 461 formed on or mounted on its lower end for engagement with the pinion 452 of the support tube 450, and the second tube 465 has gear teeth 466 formed on or mounted on its lower end for engagement with the pinion 457 of the ring 455. Each of the tubes 460, 465 can be rotated about its longitudinal axis by a motor or other suitable actuator. For example, in FIG. 31, each tube is rotated by a motor 462 through a roller 463 which is secured to the output shaft of the motor 462 and frictionally engages the outer surface of one of the tubes 460, 465. As another example, each motor 462 may drive a pinion which engages with gear teeth extending in the circumferential direction of the corresponding tube 460, 465. The angle of the rotational axis of the pinion 457 for the ring 455 (which corresponds to the second axis) will remain constant with respect to the rotational axis of the second tube 465, but the angle of the rotational axis of the pinion 452 for the support tube 450 (which corresponds to the first axis) will vary with respect to the rotational axis of the first tube 460 when the ring 455 is rotated about its axis. Therefore, the gear teeth 461 on the first tube 460 and the pinion 452 on the support tube 450 are preferably selected to permit the transmission of torque between them at a variety of angles between their axes of rotation.

Instead of employing gears to connect the tubes with the ring 455 and the support tube 450, the pinions 452, 457 may be replaced by rollers, and the gear teeth 461, 466 may be replaced by frictional surfaces at the lower ends of the tubes in rolling contact with the rollers.

Figure 32:
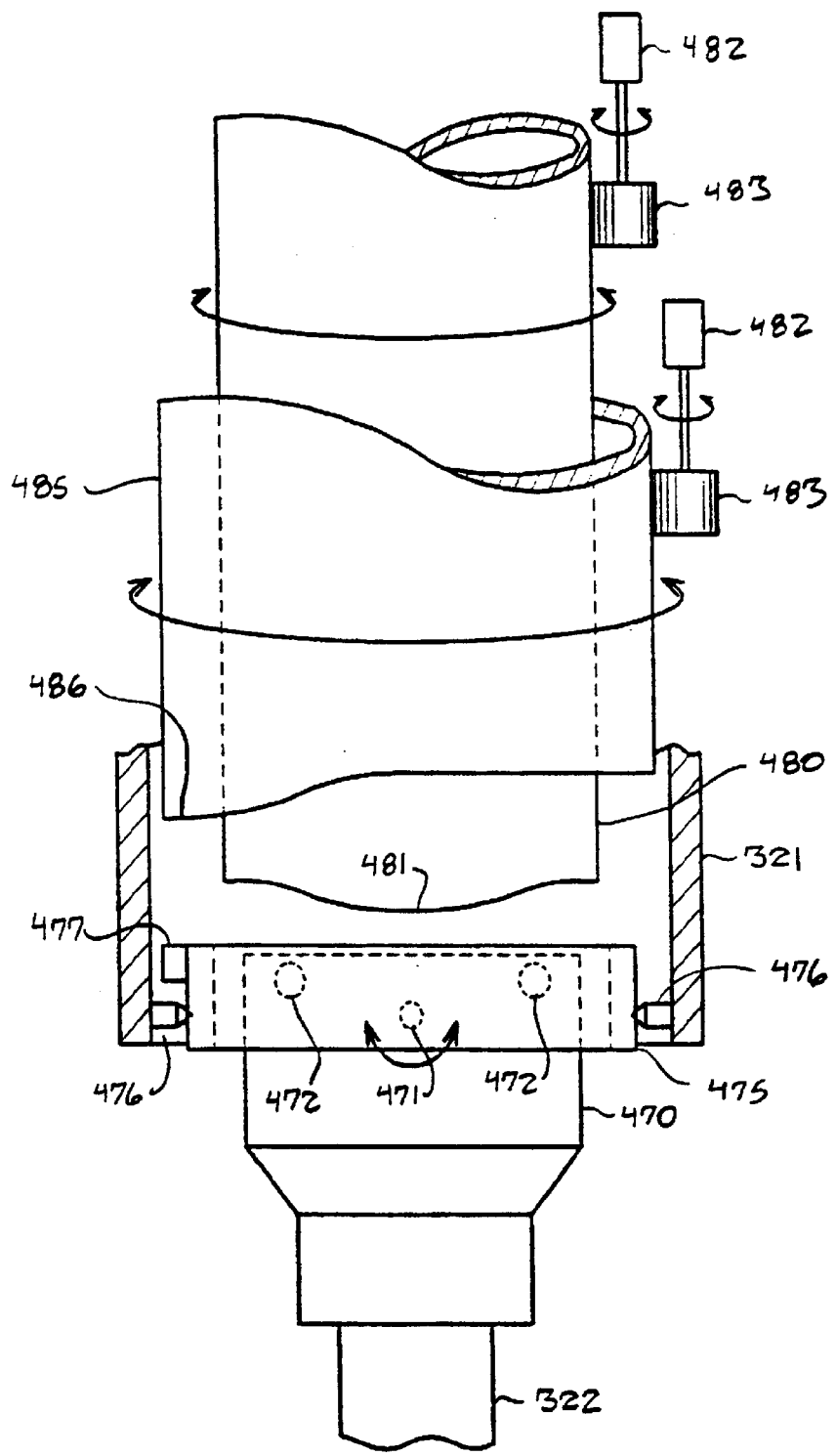
FIG. 32 is an exploded elevation of yet another example of a wrist mechanism according to the present invention.
Figure 33:
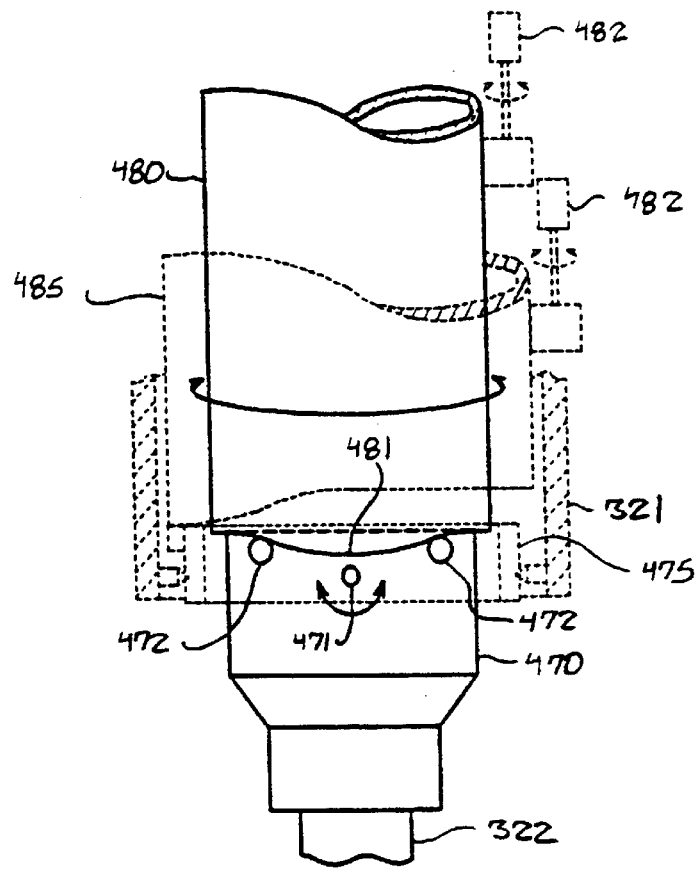
FIGS. 33 and 34 are elevations of the wrist mechanism of FIG. 32 with the support tube in two different rotational positions.
Figure 34:
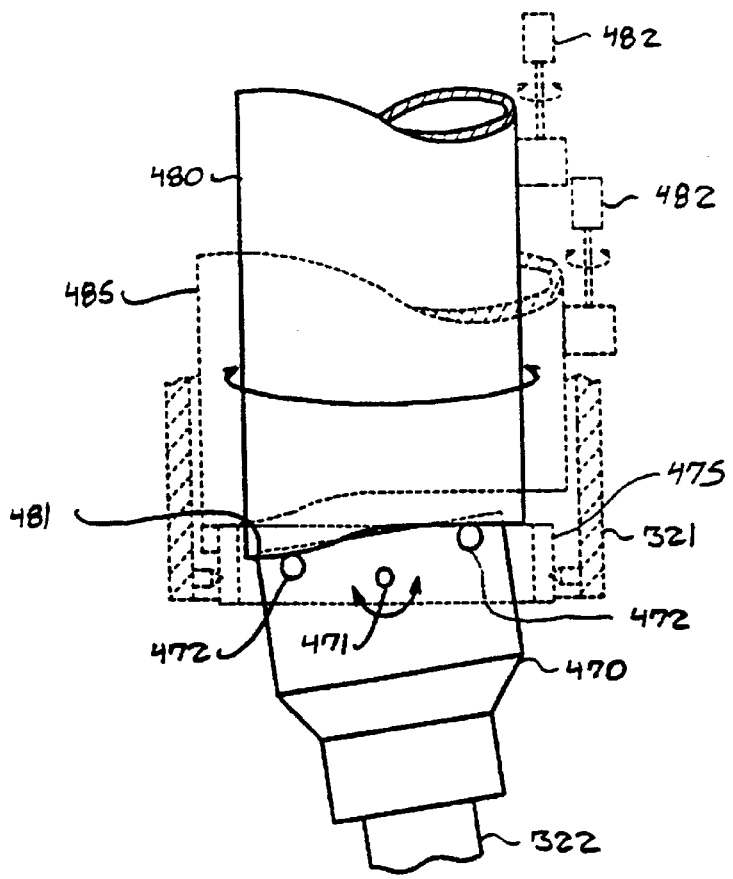

FIGS. 32–34 are views of another example of a gimbals-type wrist mechanism for use in the present invention. FIG. 32 is an exploded elevation of the wrist mechanism, FIG. 33 is an elevation of the wrist mechanism of FIG. 32 when a support tube of the wrist mechanism is in an initial horizontal position, and FIG. 34 is an elevation of the wrist mechanism with the support tube in a sloped position. Like the preceding wrist mechanisms, this mechanism includes a support tube 470 and a ring 475 surrounding the support tube 470 with the support tube 470 pivotably supported by the ring 475 for rotation about a first axis, and with the ring 475 pivotably supported by a suitable member, such as a surrounding tube 321, for pivoting about a second axis perpendicular to the first axis. The support tube 470 and the ring 475 may be pivotably supported in any suitable manner. For example, in FIG. 32, the support tube 470 is pivotably supported by two bearings 471 secured to the ring 475 in alignment with the first axis, and the ring 475 is pivotably supported by two bearings 476 secured to the tube 321 in alignment with the second axis. A rotatable first tube 480 has a cam lobe 481 formed on its lower end which is pressed in the axial direction of the first tube 480 against two cam followers 472 on the support tube 470, and a rotatable second tube 485 coaxial with and surrounding the first tube 480 has a cam lobe 486 formed on its lower end which is pressed in the axial direction of the second tube 485 against two cam followers 477 on the ring 475. The illustrated cam followers 472, 477 comprise pins projecting from the outer peripheral surface of the support tube 470 or the ring 475 on opposite sides of one of bearings 471 or one of bearings 476, but the cam followers can have any structure which enables them to contact the cam lobe or other portion of the lower end of the corresponding tube 480, 485 at various rotational positions of the tubes. Each tube 480, 485 is urged in the axial direction against the corresponding cam followers by gravity and/or by a biasing member, such as a spring. Each tube 480, 485 can be rotated about its longitudinal axis by a motor or other suitable actuator. For example, in FIG. 32, each tube can be rotated by a motor 482 which drives a roller 483 frictionally engaged with the tube. When either tube is rotated, the location of the cam lobe on the tube with respect to the corresponding cam followers changes, and the support tube 470 or the ring 475 pivots to maintain both of its cam followers in contact with the corresponding cam lobe. As an example, FIGS. 33 and 34 show how the rotation of the first tube 480 can pivot the support tube 470 about the first axis. FIG. 33 shows the first tube 480 in an initial rotational position in which the cam lobe 281 is centered with respect to cam followers 472 and the support tube 470 is horizontal. FIG. 34 shows the first tube 480 rotated about its longitudinal axis from its initial position such that the cam lobe 481 is moved to the left from the position in FIG. 33. Since the first tube 480 is always urged in its longitudinal direction against the cam followers 472 on the support tube 470, the support tube 470 pivots counterclockwise in the figure to maintain both cam followers 472 in contact with the cam lobe 481 or other region of the lower end of the first tube 480. The angle of rotation of the support tube 470 with respect to the horizontal position shown in FIG. 33 depends upon the amount of rotation of the first tube 480. If the first tube 480 is rotated about its longitudinal axis in the opposite direction in the figure, the support tube 470 will rotate in the clockwise direction to an angle corresponding to the amount of rotation of the first tube 480. The ring 475 can be rotated about the second axis by the second tube 485 in a similar manner.

The various mechanisms shown in FIGS. 27–34 for pivoting a support tube and a ring of a wrist mechanism about first and second axes can be combined with each other, with one type of mechanism being used to pivot the support tube and another type of mechanism being used to pivot the ring. For example, a gear drive like that shown in FIGS. 29 or 30 can be used to pivot the ring, and an arrangement like that shown in FIG. 27 having a shaft with a leg 421 engaging a projection can be used to pivot the support tube about the first axis.

What is claimed is:

1. A manipulator for use in medical procedures comprising:

first and second arms; and a medical tool pivotably supported by the first and second arms, the arms being movable independently of each other to manipulate the tool with at least one degree of freedom wherein each of the arms comprises first and second links connected to each other by a linear actuator for translating the second link with respect to the first link in a lengthwise direction of the second link.

2. A manipulator for use in medical procedures comprising:

first and second arms;

a medical tool pivotably supported by the first and second arms, and a linear actuator pivotably supported by the arms and supporting the medical tool for movement along a linear path transverse to the arms;

the arms being movable independently of each other to manipulate the tool with at least one degree of freedom.

3. A manipulator for use in medical procedures comprising:

first and second arms; and a medical tool pivotably supported by the first and second arms;

the arms being movable independently of each other to manipulate the tool with at least one degree of freedom wherein one of the arms has a first end and a second end capable of movement in three dimensions with respect to the first end.

4. A method of performing a medical procedure comprising:

pivotably supporting an elongated tool support having a tool mounted thereon by first and second independently movable arms;

inserting the tool support into an opening in a body wall of a patient; and moving the arms so as to pivot the tool support about a virtual pivot point located in the body wall.

5. A method as claimed in claim 4 wherein the virtual pivot point is located approximately midway through a thickness of the body wall.

6. A method as claimed in claim 4 wherein each arm has a first end and a second end, including moving the second end of each arm in a plane with respect to its first end.

7. A method as claimed in claim 4 wherein each arm has a first end and a second end, including moving the second end of one of the arms in three dimensions with respect to its first end.

8. A method as claimed in claim 7, including moving the second end of the other arm in two dimensions with respect to its first end.

9. A method as claimed in claim 4 wherein each of the arms has a first end and a second end, including moving the second end of each of the arms in three dimensions with respect to its first end.

10. An apparatus for manipulating a medical tool within a patient's body comprising:

a tube capable of insertion into a patient's body;

a gimbals joint supported by the tube and having first and second axes of rotation;

a tool supported by the gimbals joint for pivoting about the first and second axes;

first and second elongated connectors extending through the tube to the gimbals joint; and first and second actuators operatively connected to the first and second connectors, respectively, so as to exert force on the gimbals through the first and second connectors to pivot the tool about at least one of the first and second axes and wherein at least one of the first and second connectors can be rotated by the one of the first and second actuators to which it is operatively connected.

11. A manipulator for use in medical procedures comprising:

first and second arms; and a medical tool pivotably supported by the first and second arms with each arm supporting the medical tool at a different location, each arm having an associated first actuator for effecting longitudinal movement of the respective arm and an associated second actuator for effecting pivotal movement of the respective arm such that the arms are movable independently of each other in a longitudinal direction and a pivotal direction to manipulate the tool with at least three degrees of freedom.

12. A manipulator as claimed in claim 11 wherein the second actuator associated with each arm comprises a rotary actuator.

13. A manipulator as claimed in claim 12 wherein each rotary actuator comprises a brushless slotless DC motor.

14. A manipulator as claimed in claim 11 wherein the first arm is pivotable about a first axis and the second arm is pivotable about a second axis and the first and second axes are aligned with each other.

15. A manipulator as claimed in claim 14 wherein the first and second axes are vertical.

16. A manipulator as claimed in claim 14 wherein each arm comprises first and second links connected to each other by the first actuator for translating the second link with respect to the first link in a lengthwise direction of the second link perpendicular to the rotational axis of the arm.

17. A manipulator as claimed in claim 11 wherein each arm comprises a plurality of links connected in series, each link being movable with respect to an adjoining one of the links.

18. A manipulator as claimed in claim 11 wherein each of the arms comprises first and second links connected to each other by the first actuator for translating the second link with respect to the first link in a lengthwise direction of the second link.

19. A manipulator as claimed in claim 18 wherein each first actuator comprises a linear motor.

20. A manipulator as claimed in claim 19 wherein each first actuator comprises a brushless linear DC motor.

21. A manipulator as claimed in claim 11 including a linear actuator pivotably supported by the arms and supporting the medical tool for movement along a linear path transverse to the arms.

22. A manipulator as claimed in claim 21 wherein the linear actuator comprises a brushless linear DC motor.

23. A manipulator as claimed in claim 11 including a tool support on which the tool is mounted and which is capable of being inserted into a patient's body and which is pivotably supported by the arms.

24. A manipulator as claimed in claim 11 including a controller coordinating movement of the arms to maintain the tool support aligned with a virtual pivot point.

25. A manipulator as claimed in claim 24 wherein a location of the virtual pivot point along the tool support can be varied by the controller.

26. A manipulator as claimed in claim 11 wherein each arm has a first end and a second end constrained to movement in a plane with respect to the first end.

27. A manipulator as claimed in claim 11 one of the arms has a first end and a second end capable of movement in three dimensions with respect to the first end.

28. A manipulator as claimed in claim 11 wherein each of the arms has a first end and a second end capable of movement in three dimensions with respect to the first end.

29. A manipulator as claimed in claim 11 wherein the first arm has a first end and a second end capable of movement in three dimensions with respect to the first end, and the second arm has a first end and a second end capable of movement in three dimensions with respect to the first end of the second arm.

30. A manipulator as claimed in claim 11 wherein the first arm comprises first and second linear actuators, a first link movable by the first linear actuator in a lengthwise direction of the first link, a second link movable by the second linear actuator in a lengthwise direction of the second link, a third link pivotably connected to the second link, and a fourth link pivotably connected to the first link and to the third link.

31. A manipulator as claimed in claim 30 wherein the second arm includes a third linear actuator and a fifth link connected to the third linear actuator for translation in a lengthwise direction of the fifth link.

32. A manipulator as claimed in claim 31 wherein the second arm includes a sixth link pivotably connected to the fifth link.

33. An apparatus for manipulating a medical tool within a patient's body comprising:

a tube capable of insertion into a patient's body;

a gimbals joint supported by the tube and having first and second axes of rotation;

a tool supported by the gimbals joint for pivoting about the first and second axes;

first and second elongated connectors extending through the tube to the gimbals joint; and first and second actuators operatively connected to the first and second connectors, respectively, so as to exert force on the gimbals through the first and second connectors to pivot the tool about at least one of the first and second axes and wherein the first and second connectors are capable of acting in compression and tension.

34. An apparatus as claimed in claim 33 wherein the first and second actuators translate the first and second connectors in a lengthwise direction of the connectors.

35. An apparatus as claimed in claim 33 wherein the first and second axes are perpendicular to each other.

36. An apparatus as claimed in claim 33 wherein each of the first and second connectors has an arcuate transverse cross section.

37. An apparatus as claimed in claim 33 wherein the gimbals joint includes an outer portion rotatably supported by the tube and an inner portion which supports the tool and which is disposed inside and rotatably supported by the outer portion.

38. An apparatus as claimed in claim 37 wherein one of the connectors is connected to the inner portion and the other connector is connected to the outer portion of the gimbals joint.

39. An apparatus as claimed in claim 37 wherein each of the connectors is connected to the inner portion of the gimbals joint.

40. An apparatus as claimed in claim 33 wherein at least one of the first and second connectors can be rotated by the one of e first and second actuators to which it is operatively connected.

41. An apparatus as claimed in claim 33 wherein at least one of the first and second connectors is connected to the gimbals joint through a gear.

42. An apparatus as claimed in claim 33 wherein at least one of the first and second connectors can pivot the tool by exerting a camming force on the gimbals joint.

43. An apparatus as claimed in claim 33 wherein the tool is rotatably supported by the gimbals joint for rotation about a third axis transverse to the first and second axes.

44. An apparatus as claimed in claim 43 wherein the three axes are orthogonal to each other.

45. An apparatus as claimed in claim 43 including a third actuator and a shaft rotated by the third actuator and connected between the third actuator and the tool.

46. An:apparatus as claimed in claim 45 wherein each of the actuators is detachably connected to one of the connectors or the shaft.

* * * * *